United States Patent [19]
Fukami et al.

[11] Patent Number: 6,011,039
[45] Date of Patent: Jan. 4, 2000

[54] AMINOPYRIDINE DERIVATIVES

[75] Inventors: Takehiro Fukami; Toshiaki Mase; Yoshimi Tsuchiya; Akio Kanatani; Takahiro Fukuroda, all of Tsukuba, Japan

[73] Assignee: Banyu Pharmaceutical Co., Ltd., Tokyo, Japan

[21] Appl. No.: 09/142,162

[22] PCT Filed: Mar. 19, 1997

[86] PCT No.: PCT/JP97/00890

§ 371 Date: Oct. 13, 1998

§ 102(e) Date: Oct. 13, 1998

[87] PCT Pub. No.: WO97/34873

PCT Pub. Date: Sep. 25, 1997

[30] Foreign Application Priority Data

Mar. 21, 1996 [JP] Japan ........................................ 8-91968

[51] Int. Cl.[7] ........................ C07D 401/12; A61K 31/44
[52] U.S. Cl. ........................... 514/255; 514/336; 514/338; 514/340; 514/341; 514/343; 514/352; 546/268.7; 546/269.7; 546/270.1; 546/272.7; 546/280.4; 546/283.4; 546/308; 544/333; 544/405
[58] Field of Search ...................... 546/308, 255, 546/268.7, 269.7, 270.1, 272.7, 280.4, 283.4; 514/352, 255, 336, 338, 340, 341, 343; 544/333, 405

[56] References Cited

U.S. PATENT DOCUMENTS 5,446,153   8/1995   Lindstrom et al. ..................... 546/118

*Primary Examiner*—Zinna Northington Davis
*Attorney, Agent, or Firm*—Oblon, Spivak, McClelland, Maier & Neustadt, P.C.

[57] ABSTRACT

A compound represented by the formula (I) or a pharmaceutically acceptable salt thereof, and a pharmaceutical composition for hyperphagia, obesity or diabetes, which comprises such a compound or salt as an active ingredient:

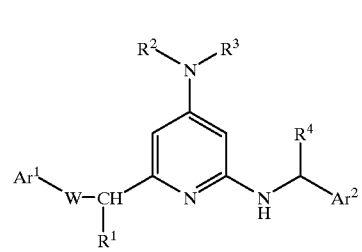

(I)

wherein $Ar^1$, $Ar^2$, $R^1$, $R^2$, $R^3$, $R^4$ and W are as defined.

17 Claims, No Drawings

AMINOPYRIDINE DERIVATIVES

This application is a 371 of PCT/JP97/00890, filed Mar. 19, 1997.

TECHNICAL FIELD

This invention is useful in the pharmaceutical field. More particularly, novel aminopyridine derivatives of the present invention are useful as neuro peptide Y receptor antagonists for various treating agents for e.g. circulatory diseases, central nervous diseases or metabolic diseases.

BACKGROUND ART

Neuropeptide Y (hereinafter referred to as NPY) is a peptide composed of 36 amino acid residues and was first isolated from porcine brain by Tatemoto et al. [Nature, vol. 296, 659 (1982)]. NPY is widely distributed in the central nervous system and the peripheral nervous system and regulates various functions in vivo as one of the most abundant peptides in the nervous systems. Namely, NPY functions as an orexigenic substance in the brain and is also related to control of emotion or a function of a central autonomic nervous system. Further, at the periphery, NPY coexists with norepinephrine at the symphathetic nerve terminal and is related to tonicity of the symphathetic nervous system. It is known that the peripheral administration of NPY results in vasoconstriction and increases the effect of other vasopressor substances including norepinephrine.

The functions of NPY are produced by its binding to NPY receptors present in the central or peripheral nervous system. Accordingly, it is possible to prevent the action of NPY by inhibiting the binding of NPY and its receptors. Consequently, substances that antagonize the binding of NPY to its receptors, are expected to be useful for prevention or treatment of various diseases associated with NPY, for example, diseases in the circulatory system, such as hypertension, renal diseases, cardiac diseases or vasospasm, central diseases, such as hyperphagia, depression, epilepsy or dementia, metabolic diseases, such as obesity, diabetes or hormone unbalance, or glaucoma [Trends in Pharmacological Sciences, vol. 15, 153 (1994)].

European Patent No. 355794, Danish Patent No. 3811193 and J. Med. Chem., vol. 37, 811 (1994), etc. disclose that some related derivatives of NPY bind to NPY receptors to antagonize the activity of NPY. In addition, recently, it appeared that certain peptides inhibit the binding of NPY to its receptors (see International Publication WO94/00486 or JP-A-6-116284).

However, these peptidic compounds have substantial problems when they are developed as pharmaceuticals. Namely, such high molecular weight peptides are generally unstable and short-lasting in vivo. Further, these compounds belong to a group of compounds whereby no substantial oral absorption or brain penetration can usually be expected.

On the other hand, recently, it appeared that certain non-peptide compounds inhibit the binding of NPY to NPY receptors and thus antagonize the activities of NPY (see JP-A-6-293794 or German Patent DE4301452-A1).

However, these non-peptide NPY antagonists are structurally totally different from the compounds of the present invention and suggest nothing about the present invention.

DISCLOSURE OF THE INVENTION

The object of the present invention is to provide a low molecular weight non-peptide compound which has a NPY antagonistic activity and is excellent in the stability and persistence in vivo and which is orally available.

The present inventors have found that a compound represented by the general formula (I):

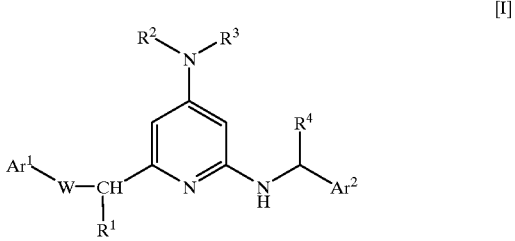

[wherein $Ar^1$ is an aryl group or an aromatic heterocyclic group, which may be substituted by a group selected from the group consisting of a lower alkyl group, a lower hydroxyalkyl group, a lower alkylene group and a group represented by —$NR^aR^b$; each of $R^a$ and $R^b$ which are the same or different, is a hydrogen atom or a lower alkyl group; $R^1$ is a hydrogen atom or a lower alkyl group; each of $R^2$ and $R^3$ which are the same or different, is a lower alkyl group, or both of $R^2$ and $R^3$ are bonded to each other to form an alkylene group which may have an oxygen atom or a sulfur atom interposed, said alkylene group being a group which may be substituted by one or two lower alkyl groups; $R^4$ is a hydrogen atom, or a lower alkyl group which may be substituted by a group selected from the group consisting of a hydroxyl group, an amino group, a carbamoyl group and a lower alkoxycarbonyl group; $Ar^2$ is an aryl group or an aromatic heterocyclic group, which may be substituted by a group selected from the group consisting of a halogen atom, a hydroxyl group, a lower alkyl group, a lower haloalkyl group, a lower alkoxy group, a lower alkylthio group, a lower hydroxyalkyl group, a lower alkoxy-lower alkyl group, a group represented by —$NR^cR^d$ and a group represented by —$NR^e$—CO—$NR^fR^g$; $R^c$ is a hydrogen atom or a lower alkyl group; $R^d$ is a hydrogen atom, a lower alkyl group, a group represented by —CO—$R^h$ or —$SO_2$—$R^i$, or a heterocyclic group which may be substituted by a group selected from the group consisting of a halogen atom, a hydroxyl group, a lower alkyl group and a lower alkoxy group; each of $R^e$ and $R^f$ which are the same or different, is a hydrogen atom or a lower alkyl group; $R^g$ is a hydrogen atom, a lower alkyl group, a lower alkenyl group, or an aryl group or an aromatic heterocyclic group, which may be substituted by a group selected from the group consisting of a halogen atom, a hydroxyl group, a lower alkyl group and a lower alkoxy group; $R^h$ is a lower alkyl group, a lower alkoxy group, a lower alkoxy-lower alkyloxy group, a lower alkenyloxy group, a lower alkynyloxy group, or a group represented by —O—$(CH_2)_n$—Het; $R^i$ is a lower alkyl group, or a lower alkenyl group; Het is a heterocyclic group; n is an integer of from 1 to 3; W is an oxygen atom, a sulfur atom, or a group represented by —$CHR^j$— or —$NR^k$—; and each of $R^j$ and $R^k$ which are the same or different, is a hydrogen atom, or a lower alkyl group], has NPY antagonistic activities, and they have accomplished the present invention.

The compound (I) of the present invention has NPY antagonistic activities and accordingly is useful as a treating agent for various diseases associated with NPY, for example, cardiovascular diseases, such as hypertension, renal diseases, cardiac diseases or vasospasm, central diseases, such as hyperphagia, depression, epilepsy or dementia, metabolic diseases, such as obesity, diabetes or hormone unbalance, or glaucoma.

Particularly, the compound (I) of the present invention is useful as a treating agent for e.g. hyperphagia, obesity or diabetes.

The present invention relates to the compound represented by the general formula (I) or a pharmaceutically acceptable salt thereof, and use thereof.

Symbols and terms used in this specification will be explained.

The lower alkyl group means a $C_{1-7}$ linear, branched or cyclic alkyl group and may, for example, be a methyl group, an ethyl group, a propyl group, an isopropyl group, a butyl group, an isobutyl group, a sec-butyl group a tert-butyl group, a pentyl group, an isopentyl group, a neopentyl group, a tert-pentyl group, a 1-methylbutyl group, a 2-methylbutyl group, a 1,2-dimethylpropyl group, a 1-ethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-2-methylpropyl group, a 1-ethyl-1-methylpropyl group, a cyclopropyl group, a cyclobutyl group, a cyclopentyl group, a cyclohexyl group, a cycloheptyl group, a cyclopropylmethyl group, a 1-cyclopropylethyl group, a 2-cyclopropylethyl group, a 1-cyclopropylpropyl group, a 2-cyclopropylpropyl group, a 3-cyclopropylpropyl group, a cyclopentylmethyl group, a 2-cyclopentylethyl group or a cyclohexylmethyl group.

The lower hydroxylalkyl group means the above-mentioned lower alkyl group having a hydroxyl group and may, for example, be a hydroxymethyl group, a 1-hydroxyethyl group, a 2-hydroxyethyl group, a 1-hydroxypropyl group, a 2-hydroxypropyl group or a 3-hydroxypropyl group.

The lower alkylene group means a $C_{2-6}$ alkylene group and may, for example, be an ethylene group, a trimethylene group, a tetramethylene group, a pentamethylene group or a hexamethylene group The aryl group means a phenyl group, a naphthyl group or an anthryl group, and a phenyl group or a naphthyl group is preferred.

The aromatic heterocyclic group means a 5-membered or 6-membered monocyclic aromatic heterocyclic group containing one or more, preferably one to three, hetero atoms, which are the same or different, selected from the group consisting of an oxygen atom, a nitrogen atom and a sulfur atom, or a fused aromatic heterocyclic group having such a monocyclic aromatic heterocyclic group fused with the above-mentioned aryl group or having the same or different such monocyclic aromatic heterocyclic groups fused with each other, and it may, for example, be a pyrrolyl group, a furyl group, a thienyl group, an imidazolyl group, a pyrazolyl group, a thiazolyl group, an isothiazolyl group, an oxazolyl group, an isoxazolyl group, a thiazolyl group, an oxadiazolyl group, a thiadiazolyl group, a pyridyl group, a pyrazinyl group, a pyrimidinyl group, a pyridazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group.

The alkylene group which may have an oxygen atom or a sulfur atom interposed, means a $C_{2-6}$ alkylene group which may have an oxygen atom or a sulfur atom interposed, and such an alkylene group forms, together with the adjacent nitrogen atom, for example, a pyrrolidinyl group, an oxazolydinyl group, an isoxazolydinyl group, a thiazolydinyl group, an isothiazolydinyl group, a piperidino group, a morpholino group, a thiomorpholino group or a hexahydro-1H-azepinyl group.

The halogen atom means a fluorine atom, a chlorine atom, a bromine atom or an iodine atom.

The lower haloalkyl group means the above-mentioned lower alkyl group having the above-mentioned halogen atom, and it may, for example, be a fluoromethyl group, a difluoromethyl group, a trifluoromethyl group, a 1-fluoroethyl group, a 2-fluoroethyl group, a 2,2,2-trifluoroethyl group, a pentafluoroethyl group, a chloromethyl group, a dichloromethyl group, a trichloromethyl group, a 1-chloroethyl group or a 2-chloroethyl group.

The lower alkoxy group means an alkoxy group having the above-mentioned lower alkyl group i.e. a $C_{1-7}$ alkoxy group, and it may, for example, be a methoxy group, an ethoxy group, a propyloxy group, an isopropyloxy group, a butoxy group, an isobutyloxy group, a tert-butoxy group, a pentyloxy group, a cyclopropyloxy group, a cyclobutyloxy group, a cyclopentyloxy group, a cyclohexyloxy group, a cycloheptyloxy group, a cyclopropylmethyloxy group, a 1-cyclopropylethyloxy group, a 2-cyclopropylethyloxy group, a 1-cyclopropylpropyloxy group, a 2-cyclopropylpropyloxy group, a 3-cyclopropylpropyloxy group, a cyclopentylmethyloxy group, a 2-cyclopentylethyloxy group or a cyclohexylmethyloxy group.

The lower alkoxycarbonyl group means an alkoxycarbonyl group having the above-mentioned lower alkoxy group i.e. a $C_{2-8}$ alkoxycarbonyl group, and it may, for example, be a methoxycarbonyl group, an ethoxycarbonyl group, a propyloxycarbonyl group, an isopropyloxycarbonyl group, a butoxycarbonyl group, an isobutyloxycarbonyl group, a tert-butoxycarbonyl group, a pentyloxycarbonyl group, a cyclopropyloxycarbonyl group, a cyclobutyloxycarbonyl group, a cyclopentyloxycarbonyl group, a cyclohexyloxycarbonyl group, a cycloheptyloxycarbonyl group, a cyclopropylmethyloxycarbonyl group, a 1-cyclopropylethyloxycarbonyl group, a 2-cyclopropylethyloxycarbonyl group, a 1-cyclopropylpropyloxycarbonyl group, a 2-cyclopropylpropyloxycarbonyl group, a 3-cyclopropylpropyloxycarbonyl group, a cyclopentylmethyloxycarbonyl group, a 2-cyclopentylethyloxycarbonyl group or a cyclohexylmethyloxycarbonyl group.

The lower alkylthio group means an alkylthio group having the above-mentioned lower alkyl group i.e. a $C_{1-7}$ alkylthio group, and it may, for example, be a methylthio group, an ethylthio group, a propylthio group, an isopropylthio group, a butylthio group, an isobutylthio group, a tert-butylthio group, a pentylthio group, a cyclopropylthio group, a cyclobutylthio group, a cyclopentylthio group, a cyclohexylthio group, a cycloheptylthio group, a cyclopropylmethylthio group, a 1-cyclopropylethylthio group, a 2-cyclopropylethylthio group, a 1-cyclopropylpropylthio group, a 2-cyclopropylpropylthio group, a 3-cyclopropylpropylthio group, a cyclopentylmethylthio group, a 2-cyclopentylethylthio group or a cyclohexylmethylthio group.

The lower alkoxy-lower alkyl group means the above-mentioned alkyl group having the above-mentioned lower alkoxy group, and it may, for example, be a methoxymethyl group, an ethoxymethyl group, a propyloxymethyl group, an isopropyloxymethyl group, cyclopropyloxymethyl group, a cyclopropylmethyloxymethyl group, a 1-methoxyethyl group, a 2-methoxyethyl group, a 1-ethoxyethyl group, a 2-ethoxyethyl group, a 2-propyloxyethyl group, a 2-isopropyloxyethyl group, a 2-cyclopropyloxyethyl group, a 2-cyclopropylmethyloxyethyl group or a 3-methoxypropyl group.

The lower alkoxy-lower alkyloxy group means an alkoxyalkyloxy group having the above-mentioned lower alkyl group substituted by the above-mentioned lower alkoxy group, and it may, for example, be a methoxymethyloxy group, an ethoxymethyloxy group, a propyloxymethyloxy group, an isopropyloxymethyloxy group, a cyclopropyloxymethyloxy group, a cyclopropylmethyloxymethyloxy group, a 1-methoxyethyloxy group, a 2-methoxyethyloxy group, a 1-ethoxyethyloxy group, a 2-ethoxyethyloxy group, a 2-propyloxyethyloxy group, a 2-isopropyloxyethyloxy group, a 2-cyclopropyloxyethyloxy group, a 2-cyclopropylmethyloxyethyloxy group or a 3-methoxypropyloxy group.

The heterocyclic group means the above-mentioned aromatic heterocyclic group, or an aliphatic heterocyclic group having the above-mentioned aromatic heterocyclic group hydrolyzed completely or incompletely, and it may, for example, be a pyrrolyl group, a pyrrolidinyl group, a furyl group, a tetrahydrofuranyl group, a thienyl group, an imidazolyl group, a pyrazolyl group, a thiazolyl group, a thiazolinyl group, an isothiazolyl group, an oxazolyl group, an isoxazolyl group, a triazolyl group, an oxadiazolyl group, a thiadiazolyl group, a pyridyl group, a piperidyl group, a pyrazinyl group, a pyrimidinyl group, a pyridazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group.

The lower alkenyl group means a $C_{2-7}$ linear or branched alkenyl group, and it may, for example, be a vinyl group, a 2-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group or a 4-pentenyl group.

The lower alkenyloxy group means an alkenyloxy group having the above-mentioned lower alkenyl group i.e. a $C_{2-7}$ alkenyloxy group, and it may, for example, be a 2-propenyloxy group, a 2-methyl-2-propenyloxy group, a 2-butenyloxy group, a 3-butenyloxy group, a 2-pentenyloxy group, a 3-methyl-2-butenyloxy group, a 3-methyl-3-butenyloxy group or a 2-hexenyloxy group.

The lower alkynyloxy group means an alkynyloxy group having a $C_{2-7}$ linear or branched alkynyl group, and it may, for example, be a 2-propynyloxy group, a 1-methyl-2-propynyloxy group, a 2-butynyloxy group, a 1-methyl-2-butynyloxy group or a 2-pentynyloxy group.

The pharmaceutically acceptable salt of the compound represented by the general formula (I) means one commonly used in the pharmaceutically field, such as a salt of an acid-addition salt based on a basic heterocyclic group such as a pyridine ring or a basic group such as an amino substituent, in the formula (I).

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonate such as a methanesulfonate, an isethionate, a benzenesulfonate or a p-toluenesulfonate.

In order to more specifically describe the compound of the present invention represented by the above general formula (I), various symbols used in the formula (I) will be explained in further detail with reference to their preferred specific examples.

$Ar^1$ means an aryl group or an aromatic heterocyclic group, which may be substituted by a group selected from the group consisting of a lower alkyl group, a lower hydroxyalkyl group, a lower alkylene group and a group represented by $-NR^aR^b$.

The aryl group or the aromatic heterocyclic group, which may be substituted by a group selected from the group consisting of a lower alkyl group, a lower hydroxyalkyl group, a lower alkylene group and a group represented by $-NR^aR^b$, means an unsubstituted above-mentioned aryl or above-mentioned aromatic heterocyclic group, or the above-mentioned aryl or above-mentioned aromatic heterocyclic group having substituent(s) at optional position(s) for substitution, and the substituent(s) may be one or more, preferably one or two, which are the same or different, selected from the group consisting of a lower alkyl group, a lower hydroxyalkyl group, a lower alkylene group and a group represented by $-NR^aR^b$.

The lower alkyl group for the substituent is preferably, for example, a methyl group, an ethyl group, a propyl group, an isopropyl group, a cyclopropyl group, a butyl group, an isobutyl group, a sec-butyl group, a tert-butyl group or a pentyl group, more preferably, a methyl group, an ethyl group, a propyl group, an isopropyl group or a cyclopropyl group. The lower hydroxyalkyl group for the substituent, is preferably, for example, a hydroxymethyl group, a 1-hydroxyethyl group or a 2-hydroxyethyl group, more preferably, a hydroxymethyl group or a 1-hydroxyethyl group.

The lower alkylene group for the substituent is preferably, for example, an ethylene group, a trimethylene group or a tetramethylene group, more preferably, a trimethylene group or a tetramethylene group.

In the group represented by $-NR^aR^b$ for the substituent, each of $R^a$ and $R^b$ which are the same or different, is a hydrogen atom or a lower alkyl group. As the lower alkyl group for $R^a$ or $R^b$, a methyl group or an ethyl group is, for example, preferred. Accordingly, as the group represented by $-NR^aR^b$, preferred is a group wherein each of for $R^a$ and $R^b$ which are different, is a hydrogen atom or a methyl group, or a hydrogen atom or an ethyl group, or a group wherein each of $R^a$ and $R^b$ which are the same, is a methyl group.

As the substituent, a lower alkyl group or a lower alkylene group is preferred.

The aryl group for $Ar^1$ may, for example, be a phenyl group or a naphthyl group.

The aromatic heterocyclic group for $Ar^1$ is preferably, for example, a furyl group, a thienyl group, an imidazolyl group, a thiazolyl group, an oxazolyl group, a triazolyl group, an oxadiazolyl group, a thiadiazolyl group, a pyridyl group, a pyrimidinyl group, a pyridazinyl group or a benzothiazolyl group, more preferably a thiazolyl group, an oxazolyl group or a thiadiazolyl group.

Accordingly, $Ar^1$ may, for example, be a 5-methylphenyl group, a 5-indanyl group, a 5-ethyl-2-furyl group, a 5-ethyl-2-thienyl group, a 4-methyl-2-thiazolyl group, a 4-ethyl-2-thiazolyl group, a 4-propyl-2-thiazolyl group, a 4-isopropyl-2-thiazolyl group, a 5-isopropyl-2-thiazolyl group, a 5-methyl-2-thiazolyl group, a 5-ethyl-2-thiazolyl group, a 5-propyl-2-thiazolyl group, a 5-butyl-2-thiazolyl group, a 4,5-dimethyl-2-thiazolyl group, a 4-ethyl-5-methyl-2-thiazolyl group, a 5-ethyl-4-methyl-2-thiazolyl group, a 4,5-diethyl-2-thiazolyl group, a 4-methyl-5-propyl-2-thiazolyl group, a 5-methyl-4-propyl-2-thiazolyl group, a 2-cyclohexeno[d]thiazolyl group, a 2-cyclopenteno[d]thiazolyl group, a 4-hydroxymethyl-2-thiazolyl group, a 5-(1-hydroxyethyl)-2-thiazolyl group, a 4-ethyl-2-oxazolyl group, a 5-ethyl-2-oxazolyl group, a 5-propyl-2-oxazolyl group, a 5-ethyl-4-methyl-2-oxazolyl group, a 5-ethyl-1,2,4-triazol-3-yl group, a 5-propyl-1,2,4-triazol-3-yl group, a 4-methyl-1,2,4-triazol-3-yl group, a 5-ethyl-4-methyl-1,2,4-triazol-3-yl group, a 4-methyl-5-propyl-1,2,4-triazol-3-yl group, a 5-butyl-4-methyl-1,2,4-triazol-3-yl group, a 4,5-diethyl-1,2,4-triazol-3-yl group, a 5-ethyl-1,3,4-oxadiazol-2-yl group, a 5-ethyl-1,3,4-thiadiazol-2-yl group, a 5-methylamino-1,3,4-thiadiazol-2-yl group, a 5-dimethylamino-1,3,4 -thiadiazol-2-yl group, a 5-ethylamino-1,3,4-thiadiazol-2-yl group, a 5-propyl-1,3,4-thiadiazol-2-yl group, a 5-isopropyl-1,3,4-thiadiazol-2-yl group, a 2-pyridyl group, a 2-pyrimidinyl group or a 2-benzothiazolyl group, and among them, a 4-methyl-2-thiazolyl group, a 4-ethyl-2-thiazolyl group, a 5-ethyl-2-thiazolyl group, a 4,5-dimethyl-2-thiazolyl group, a 4-ethyl-5-methyl-2-thiazolyl group, a 5-ethyl-4-methyl-2-thiazolyl group, a 4,5-diethyl-2-thiazolyl group, a 4-methyl-5-propyl-2-thiazolyl group, a 5-methyl-4-propyl-2-thiazolyl group, a 2-cyclohexeno[d]thiazolyl group, a 2-cyclopenteno[d]thiazolyl group, a 5-(1-hydroxyethyl)-2-thiazolyl group, a 4-ethyl-2-oxazolyl group, a 5-ethyl-2-oxazolyl group, a 5-propyl-2-oxazolyl group, a 5-ethyl-4-methyl-2-oxazolyl group, or a 5-ethyl-1,3,4-thiadiazol-2-yl, is, for example, preferred.

$R^1$ means a hydrogen atom or a lower alkyl group.

$R^1$ is preferably, for example, a hydrogen atom, a methyl group, an ethyl group, a propyl group or an isopropyl group, more preferably a hydrogen atom.

Each of $R^2$ and $R^3$ which are the same or different, is a lower alkyl group, or both of $R^2$ and $R^3$ are bonded to each other to form an alkylene group which may have an oxygen atom or a sulfur atom interposed, said alkylene group being a group which may be substituted by one or two lower alkyl groups.

The lower alkyl group for $R^2$ and $R^3$ is preferably, for example, a methyl group or an ethyl group.

The alkylene group which may have an oxygen atom or a sulfur atom interposed, said alkylene group being a group which may be substituted by one or two lower alkyl groups, means an unsubstituted above-mentioned alkylene group which may have an oxygen atom or a sulfur atom interposed, or a group having one or two above-mentioned lower alkyl groups, which are the same or different, at optional position (s) for substitution on the above-mentioned alkylene group which may have an oxygen atom or a sulfur atom interposed, and said lower alkyl group is preferably, for example, a methyl group, an ethyl group, a propyl group or an isopropyl group, more preferably a methyl group.

The alkylene group which may have an oxygen atom or a sulfur atom interposed is preferably a group which forms, together with the adjacent nitrogen atom, for example, a piperidino group, a morpholino group or a thiomorpholino group, more preferably a morpholino group.

$R^2$ and $R^3$ are preferably such that both of $R^2$ and $R^3$ are bonded to each other to form an alkylene group which may have an oxygen atom or a sulfur atom interposed, said alkylene group being a group which may be substituted by one or two lower alkyl groups.

$R^4$ is a hydrogen atom or a lower alkyl group which may be substituted by a group selected from the group consisting of a hydroxyl group, an amino group, a carbamoyl group and a lower alkoxycarbonyl group.

The lower alkyl group which may be substituted by a group selected from the group consisting of a hydroxyl group, an amino group, a carbamoyl group and a lower alkoxycarbonyl group, means an unsubstituted above-mentioned lower alkyl group or a lower alkyl group having substituent(s) at optional position(s) for substitution, and said substituent(s) may be one or more, preferably one or two, which are the same or different, selected from the group consisting of a hydroxyl group, an amino group, a carbamoyl group and a lower alkoxycarbonyl group.

The lower alkyl group for $R^4$ is preferably, for example, a methyl group, an ethyl group, a propyl group or an isopropyl group.

Accordingly, $R^4$ may, for example, be a hydrogen atom, a methyl group, an ethyl group, a propyl group, an isopropyl group, a hydroxymethyl group, a 1-hydroxyethyl group, a 2-hydroxyethyl group, a 3-hydroxypropyl group, an aminomethyl group, a 1-aminoethyl group, a 2-aminoethyl group, a 3-aminopropyl group, a carbamoylmethyl group, a 1-carbamoylethyl group, a 2-carbamoylethyl group, a 3-carbamoylpropyl group, a methoxycarbonylmethyl group, a 1-methoxycarbonylethyl group, a 2-methoxycarbonylethyl group, a 3-methoxycarbonylpropyl group, an ethoxycarbonylmethyl group, a 1-ethoxycarbonylethyl group, a 2 -ethoxycarbonylethyl group or a 3-ethoxycarbonylpropyl group, and among them, a hydrogen atom, a methyl group, an ethyl group or a 3-aminopropyl group is, for example, preferred.

$Ar^2$ is an aryl group or an aromatic heterocyclic group, which may be substituted by a group selected from the group consisting of a halogen atom, a hydroxyl group, a lower alkyl group, a lower haloalkyl group, a lower alkoxy group, a lower alkylthio group, a lower hydroxyalkyl group, a lower alkoxy-lower alkyl group, a group represented by —$NR^cR^d$ and a group represented by —$NR^e$—CO—$NR^fR^g$.

The aryl group or the aromatic heterocyclic group, which may be substituted by a group selected from the group consisting of a halogen atom, a hydroxyl group, a lower alkyl group, a lower haloalkyl group, a lower alkoxy group, a lower alkylthio group, a lower hydroxyalkyl group, a lower alkoxy-lower alkyl group, a group represented by —$NR^cR^d$ and a group represented by —$NR^eCO$—$NR^fR^g$, means an unsubstituted above-mentioned aryl or above-mentioned aromatic heterocyclic group, or the above-mentioned aryl or above-mentioned aromatic heterocyclic group having substituent(s) at optional position(s) for substitution, said substituent(s) may be one or more, preferably one or two, which are the same or different, selected from the group consisting of a halogen atom, a hydroxyl group, a lower alkyl group, a lower haloalkyl group, a lower alkoxy group, a lower alkylthio group, a lower hydroxyalkyl group, a lower alkoxy-lower alkyl group, a group represented by —$NR^cR^d$ and a group represented by —$NR^3$—CO—$NR^fR^6$.

As the halogen atom for the substituent, a fluorine atom or a chlorine atom is, for example, preferred.

As the lower alkyl group for the substituent, a methyl group, an ethyl group, a propyl group, an isopropyl group, a butyl group is, for example, preferred, and more preferred is, for example, a methyl group or an ethyl group.

As the lower haloalkyl group for the substituent, a fluoromethyl group or trifluoromethyl group is, for example, preferred.

As the lower alkoxy group for the substituent, a methoxy group, an ethoxy group or a propyloxy group is, for example, preferred, and more preferred is, for example, a methoxy group.

As the lower alkylthio group for the substituent, a methylthio group, an ethylthio group or a propylthio group is, for example, preferred, and more preferred is, for example, a methylthio group.

As the lower hydroxyalkyl group for the substituent, a hydroxymethyl group, a 1-hydroxyethyl group, a 2-hydroxyethyl group, a 3-hydroxypropyl group is, for example, preferred, and more preferred is, for example, a hydroxymethyl group.

As the lower alkoxy-lower alkyl group for the substituent, a methoxymethyl group, a 1-methoxyethyl group, a 2-methoxyethyl group, a 3-methoxypropyl group, an ethoxymethyl group, a 1-ethoxyethyl group, a 2-ethoxyethyl group, a 3-ethoxypropyl group or a propyloxymethyl group is, for example, preferred, and more preferred is, for example, a methoxymethyl group.

In the group represented by $—NR^cR^d$ for the substituent, $R^c$ is a hydrogen atom or a lower alkyl group; $R^d$ is a hydrogen atom, a lower alkyl group, a group represented by $—CO—R^h$ or $—SO_2—R^i$, or a heterocyclic group which may be substituted by a group selected from the group consisting of a halogen atom, a hydroxyl group, a lower alkyl group and a lower alkoxy group.

In the group represented by $—NR^e—CO—NR^fR^g$ for the substituent, each of $R^e$ and $R^f$ which are the same or different, is a hydrogen atom or a lower alkyl group; $R^g$ is a hydrogen atom, a lower alkyl group, a lower alkenyl group, or an aryl group or an aromatic heterocyclic group, which may be substituted by a group selected from the group consisting of a halogen atom, a hydroxyl group, a lower alkyl group and a lower alkoxy group.

The substituent is preferably a group selected from the group consisting of a halogen atom, a lower alkyl group, a lower haloalkyl group, a lower alkoxy group, a lower alkylthio group, a lower hydroxyalkyl group, a lower alkoxy-lower alkyl group, a group represented by $—NR^cR^d$ and a group represented by $—NR^e—CO—NR^fR^g$.

As $R^c$, a hydrogen atom, a methyl group, an ethyl group, a propyl group or an isopropyl group is, for example, preferred, and more preferred is, for example, a hydrogen atom.

As the lower alkyl group for $R^d$, a methyl group, an ethyl group, a propyl group, an isopropyl group or a butyl group is, for example, preferred, and more preferred is, for example, a methyl group.

In the group represented by $—CO—R^h$ for $R^d$, $R^h$ is a lower alkyl group, a lower alkoxy group, a lower alkoxy-lower alkyloxy group, a lower alkenyloxy group, a lower alkynyloxy group, or a group represented by $—O—(CH_2)_n—Het$.

In the group represented by $—SO_2—R$ for $R^d$, $R^i$ is a lower alkyl group, or a lower alkenyl group.

The heterocyclic group which may be substituted by a group selected from the group consisting of a halogen atom, a hydroxyl group, a lower alkyl group and a lower alkoxy group, for $R^d$, means an unsubstituted above-mentioned heterocyclic group or the above-mentioned heterocyclic group having substituent(s) at optional position(s) for substitution, and said substituent(s) may be one or more, preferably one or two, which are the same or different, selected from the group consisting of a halogen atom, a hydroxyl group, a lower alkyl group and a lower alkoxy group.

As the halogen atom for the substituent, a fluorine atom or a chlorine atom is, for example, preferred.

As the lower alkyl group for the substituent, a methyl group, an ethyl group, a propyl group, an isopropyl group or a butyl group is, for example, preferred, and more preferred is, for example, a methyl group.

As the lower alkoxy group for the substituent, a methoxy group, an ethoxy group or a propyloxy group is, for example, preferred, and more preferred is, for example, a methoxy group.

As said substituent(s), a lower alkyl group is preferred.

As the heterocyclic group for $R^d$, an oxazolyl group or a thiazolinyl group is, for example, preferred.

Accordingly, as the heterocyclic group which may be substituted by a group selected from the group consisting of a halogen atom, a hydroxyl group, a lower alkyl group and a lower alkoxy group, a 4-methyl-2-oxazolyl group or a 5-methyl-2-thiazolin-2-yl group is, for example, preferred.

As $R^d$, a group represented by $—CO—R^h$, or a heterocyclic group which may be substituted by a group selected from the group consisting of a halogen atom, a hydroxyl group, a lower alkyl group and a lower alkoxy group, is preferred.

Accordingly, as the group represented by $—NR^cR^d$, a group wherein $R^c$ is a hydrogen atom, and $R^d$ is a group represented by $—CO—R^h$, or a group wherein $R^c$ is a hydrogen atom, and the heterocyclic group for $R^d$ is an oxazolyl group or a thiazolinyl group, is preferred.

As the lower alkyl group for $R^e$ and $R^f$, a methyl group, an ethyl group, a propyl group, an isopropyl group or a butyl group is, for example, preferred, and more preferred is, for example, a methyl group.

As $R^e$ and $R^f$, a hydrogen atom is, for example, preferred.

As the lower alkyl group for $R^g$, a methyl group, an ethyl group, a propyl group, an isopropyl group, a butyl group or a cyclopropyl group is, for example, preferred, and more preferred is, for example, a cyclopropyl group.

As the lower alkenyl group for $R^g$, a 2-propenyl group, an isopropenyl group, a 2-butenyl group or a 3-methyl-2-butenyl group is, for example, preferred, and more preferred is, for example, a 2-propenyl group.

The aryl group or the aromatic heterocyclic group, which may be substituted by a group selected from the group consisting of a halogen atom, a hydroxyl group, a lower alkyl group, and a lower alkoxy group, for $R^g$, means an unsubstituted above-mentioned aryl or above-mentioned aromatic heterocyclic group, or the above-mentioned aryl or above-mentioned aromatic heterocyclic group having substituent(s) at optional position(s) for substitution, and said substituent(s) may be one or more, preferably one or two, which are the same or different, selected from the group consisting of a halogen atom, a hydroxyl group, a lower alkyl group and a lower alkoxy group.

As the halogen atom for the substituent, a fluorine atom or a chlorine atom is, for example, preferred.

As the lower alkyl group for the substituent, a methyl group, an ethyl group, a propyl group, an isopropyl group or a butyl group is, for example, preferred, and more preferred is, for example, a methyl group.

As the lower alkoxy group for the substituent, a methoxy group, an ethoxy group or a propyloxy group is, for example, preferred, and more preferred is, for example, a methoxy group.

As said substituent, a hydroxyl group is preferred.

As the aryl group for $R^g$, a phenyl group is, for example, preferred.

As $R^g$, a lower alkyl group or a lower alkenyl group is preferred, and more preferred is a lower alkenyl group.

Accordingly, as the group represented by —NR$^e$—CO—NR$^f$R$^g$, a group wherein R$^e$ and R$^f$ are the same and hydrogen atoms, and R$^g$ is a lower alkenyl group, is preferred.

As the lower alkyl group for R$^h$, a methyl group, an ethyl group, a propyl group, an isopropyl group or a butyl group is, for example, preferred, and more preferred is, for example, a methyl group.

As the lower alkoxy group for R$^h$, a methoxy group, an ethoxy group, a propyloxy group, an isopropyloxy group, an isobutyloxy group, a pentyloxy group or a cyclopropylmethyloxy group is, for example, preferred, and more preferred is, for example, a propyloxy group, an isobutyloxy group or a cyclopropylmethyloxy group.

As the lower alkoxy-lower alkyloxy group for R$^h$, a methoxymethyloxy group, a propyloxymethyloxy group, a cyclopropyloxymethyloxy group, a cyclopropylmethyloxymethyloxy group, a 2-methoxyethyloxy group, a 2-ethoxyethyloxy group, a 2-cyclopropyloxyethyloxy group or a 2-cyclopropylmethyloxyethyloxy group is, for example, preferred.

As the lower alkenyloxy group for R$^h$, a 2-propenyloxy group or a 3-methyl-2-butenyloxy group is, for example, preferred.

As the lower alkynyloxy group for R$^h$, a 2-propynyloxy group is, for example, preferred.

In the group represented by —O—(CH$_2$)$_n$—Het for R$^h$, Het is a heterocyclic group; and n is an integer of from 1 to 3.

As Het, a furyl group, a thienyl group or a tetrahydrofuranyl group is, for example, preferred, and as n, 1 is preferred.

As R$^h$, a lower alkoxy group, a lower alkenyloxy group or a lower alkynyloxy group is preferred.

As the lower alkyl group for R$^i$, a methyl group, an ethyl group, a propyl group, an isopropyl group or a butyl group is, for example, preferred, and more preferred is, for example, a methyl group.

As the lower alkenyl group for R$^i$, a 2-propenyl group is, for example, preferred.

As R$^i$, a lower alkyl group is preferred.

As the aryl group for Ar$^2$, a phenyl group is, for example, preferred.

As the aromatic heterocyclic group for Ar$^2$, a thienyl group or a pyridyl group is, for example, preferred.

Accordingly, Ar$^2$ may, for example, be a phenyl group, a 3-hydroxyphenyl group, a 3-methylphenyl group, a 3-methoxyphenyl group, a 3-aminophenyl group, a 3-methylsulfonylaminophenyl group, a 3-(2-propenyloxycarbonylamino)phenyl group, a 3-(2-propenylaminocarbonylamino)phenyl group, a 3-propyloxycarbonylaminophenyl group, a 3-methoxycarbonylaminophenyl group, a 3-isopropyloxycarbonylaminophenyl group, a 3-pentyloxycarbonylaminophenyl group, a 3-(3-methyl-2-butenyloxycarbonylamino)phenyl group, a 2-acetamidophenyl group, a 3-cyclopropylmethyloxycarbonylaminophenyl group, a 3-(2-furylmethyloxycarbonylamino)phenyl group, a 3-(2-thienylmethyloxycarbonylamino)phenyl group, a 3-(cyclopropylaminocarbonylamino)phenyl group, a 3-(3-furylmethyloxycarbonylamino)phenyl group, a 3-(5-methyl-2-thiazolin-2-yl amino)phenyl group, a 3-ethoxycarbonylaminophenyl group, a 3-isobutyloxycarbonylaminophenyl group, a 3-(4-methyl-2-oxazolylamino)phenyl group, a 2-methyl-3-(2-propenyloxycarbonylamino)phenyl group, a 3-methoxy-5-(2-propenyloxycarbonylamino)phenyl group, a 3-ethoxy-5-(2-propenyloxycarbonylamino)phenyl group, a 3-amino-5-(2-propenyloxycarbonylamino)phenyl group, a 2-fluoro-5-(2-propenyloxycarbonylamino)phenyl group, a 2-chloro-5-(2-propenyloxycarbonylamino)phenyl group, a 4-fluoro-3-(2-propenyloxycarbonylamino)phenyl group, a 4-chloro-3-(2-propenyloxycarbonylamino)phenyl group, a 3-fluoro-5-(2-propenyloxycarbonylamino)phenyl group, a 3-dimethylamino-5-(2-propenyloxycarbonylamino)phenyl group, a 3-chloro-5-(2-propenyloxycarbonylamino)phenyl group, a 3-(2-propenyloxycarbonylamino)-5-trifluoromethylphenyl group, a 3-methyl-5-(2-propenyloxycarbonylamino) phenyl group, a 3-ethyl-5-(2-propenyloxycarbonylamino)phenyl group, a 3-(2-propenyloxycarbonylamino)-5-propylphenyl group, a 3-isopropyl-5-(2-propenyloxycarbonylamino)phenyl group, a 3-cyclopropyl-5-(2-propenyloxycarbonylamino)phenyl group, a 3-isobutyl-5-(2-propenyloxycarbonylamino)phenyl group, a 3-(2-propenyloxycarbonylamino)-5-propyloxyphenyl group, a 3-isopropyloxy-5-(2-propenyloxycarbonylamino )phenyl group, a 3-cyclopropyloxy-5-(2 -propenyloxycarbonylamino)phenyl group, a 3-methylthio-5-(2-propenyloxycarbonylamino)phenyl group, a 3-hydroxymethyl-5-(2-propenyloxycarbonylamino)phenyl group, a 3-methoxymethyl-5-(2-propenyloxycarbonylamino)phenyl group, a 3-chloro-5-cyclopropylmethyloxycarbonylaminophenyl group, a 3-cyclopropylmethyloxycarbonylamino-5-methylphenyl group, a 3-cyclopropylmethyloxycarbonylamino-5-ethylphenyl group, a 3-cyclopropylmethyloxycarbonylamino-5-propylphenyl group, a 3-cyclopropylmethyloxycarbonylamino-5-isopropylphenyl group, a 3-cyclopropylmethyloxycarbonylamino-5-trifluoromethylphenyl group, a 3-cyclopropylmethyloxycarbonylamino-5-methoxyphenyl group, a 3-cyclopropylmethyloxycarbonylamino-5-ethoxyphenyl group, a 3-cyclopropylmethyloxycarbonylamino-5-hydroxymethylphenyl group, a 3-chloro-5-isobutyloxycarbonylaminophenyl group, a 3-isobutyloxycarbonylamino-5-methylphenyl group, a 3-ethyl-5-isobutyloxycarbonylaminophenyl group, a 3-isobutyloxycarbonylamino-5-propylphenyl group, a 3-isobutyloxycarbonylamino-5-isopropylphenyl group, a 3-isobutyloxycarbonylamino-5-trifluoromethylphenyl group, a 3-isobutyloxycarbonylamino-5-methoxyphenyl group, a 3-ethoxy-5-isobutyloxycarbonylaminophenyl group, a 5-(2-propenyloxycarbonylamino)-2-thienyl group, a 6-(2-propenyloxycarbonylamino)-2-pyridyl group, a 2-(2-propenyloxycarbonylamino)-4-pyridyl group, a 3-chloro-5 -(3-methyl-2-butenyloxycarbonylamino)phenyl group, a 3-methoxy-5-(3-methyl-2-butenyloxycarbonylamino)phenyl group, a 3-methyl-5-(3-methyl-2-butenyloxycarbonylamino)phenyl group, or a 3-(3-methyl-2-butenyloxycarbonylamino)-5-trifluoromethylphenyl group, and among them, preferred is a 3-(2-propenyloxycarbonylamino)phenyl group, a 3-(2-propenylaminocarbonylamino)phenyl group, a 3-propyloxycarbonylaminophenyl group, a 3-(3-methyl-2-butenyloxycarbonylamino)phenyl group, a 3-cyclopropylmethyloxycarbonylaminophenyl group, a 3-isobutyloxycarbonylaminophenyl group, a 3-methoxy-5-(2-propenyloxycarbonylamino)phenyl group, a 3-ethoxy-5-(2-propenyloxycarbonylamino)phenyl group, a 4-fluoro-3-(2-propenyloxycarbonylamino)phenyl group, a 3-fluoro-5-

(2-propenyloxycarbonylamino)phenyl group, a 3-chloro-5-(2-propenyloxycarbonylamino)phenyl group, a 3-methyl-5-(2-propenyloxycarbonylamino)phenyl group, a 3-ethyl-5-(2-propenyloxycarbonylamino)phenyl group, a 3-(2-propenyloxycarbonylamino)-5-propylphenyl group, a 3-isopropyl-5-(2-propenyloxycarbonylamino)phenyl group, a 3-(2-propenyloxycarbonylamino)-5-trifluoromethylphenyl group, a 3-methylthio-5-(2-propenyloxycarbonylamino) phenyl group, a 3-hydroxymethyl-5-(2-propenyloxycarbonylamino)phenyl group, a 3-methoxymethyl-5-(2-propenyloxycarbonylamino)phenyl group, a 3-chloro-5-cyclopropylmethyloxycarboylaminophenyl group, a 3-cyclopropylmethyloxycarbonylamino-5-methylphenyl group, a 3-cyclopropylmethyloxycarbonylamino-5-ethylphenyl group, a 3-cyclopropylmethyloxycarbonylamino-5-propylphenyl group, a 3-cyclopropylmethyloxycarbonylamino-5-isopropylphenyl group, a 3-cyclopropylmethyloxycarbonylamino-5-trifluormethylphenyl group, a 3-cyclopropylmethyloxycarbonylamino-5-methoxyphenyl group, a 3-cyclopropylmethyloxycarbonylamino-5-ethoxyphenyl group, a 3-cyclopropylmethyloxycarbonylamino-5-hydroxymethylphenyl group, a 3-chloro-5-isobutyloxycarbonylaminophenyl group, a 3-isobutyloxycarbonylamino-5-methylphenyl group, a 3-ethyl-5-isobutyloxycarbonylaminophenyl group, a 3-isobutyloxycarbonylamino-5-propylphenyl group, a 3-isobutyloxycarbonylamino-5-isopropylphenyl group, a 3-isobutyloxycarbonylamino-5-trifluoromethylphenyl group, a 3-isobutyloxycarbonylamino-5-methoxyphenyl group, a 3-ethoxy-5-isobutyloxycarbonylaminophenyl group, a 3-chloro-5-(3-methyl-2-butenyloxycarbonylamino) phenyl group, a 3-methoxy-5-(3-methyl-2-butenyloxycarbonylamino)phenyl group, a 3-methyl-5-(3-methyl-2-butenyloxycarbonylamino)phenyl group, or a 3-(3-methyl-2-butenyloxycarbonylamino)-5-trifluoromethylphenyl group.

W is an oxygen atom, a sulfur atom, or a group represented by —CHR$^j$— or —NR$^k$—.

A compound wherein W is a sulfur atom or a group represented by —CHR$^j$—, is preferred.

Each of R$^j$ and R$^k$ which are the same or different, is a hydrogen atom or a lower alkyl group.

As R$^j$ and R$^k$, a hydrogen atom, a methyl group, an ethyl group, a propyl group, an isopropyl group or a butyl group is, for example, preferred, and more preferred is, for example, a hydrogen atom.

A compound represented by the general formula (I-a):

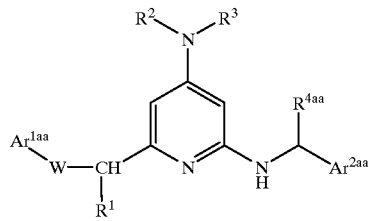

[I-a]

[wherein Ar$^{1aa}$ is an aryl group or an aromatic heterocyclic group, which may be substituted by a group selected from the group consisting of a lower alkyl group and a group represented by —NR$^a$R$^b$; each of R$^a$ and R$^b$ which are the same or different, is a hydrogen atom or a lower alkyl group; each of R$^1$ and R$^{4aa}$ which are the same or different, is a hydrogen atom or a lower alkyl group; each of R$^2$ and R$^3$ which are the same or different, is a lower alkyl group, or both of R$^2$ and R$^3$ are bonded to each other to form an alkylene group which may have an oxygen atom or a sulfur atom interposed, said alkylene group being a group which may be substituted by one or two lower alkyl groups; Ar$^{2aa}$ is an aryl group or an aromatic heterocyclic group, which may be substituted by a group selected from the group consisting of a halogen atom, a hydroxyl group, a lower alkyl group, a lower haloalkyl group, a lower alkoxy group, a group represented by —NR$^c$R$^d$ and a group represented by —NR$^e$—CO—NR$^f$R$^g$; R$^c$ is a hydrogen atom or a lower alkyl group; R$^d$ is a hydrogen atom, a lower alkyl group, a group represented by —CO—R$^h$ or —SO$_2$—R$^i$, or a heterocyclic group which may be substituted by a group selected from the group consisting of a halogen atom, a hydroxyl group, a lower alkyl group and a lower alkoxy group; each of R$^e$ and R$^f$ which are the same or different, is a hydrogen atom or a lower alkyl group; R$^g$ is a hydrogen atom, a lower alkyl group, a lower alkenyl group, or an aryl group or an aromatic heterocyclic group, which may be substituted by a group selected from the group consisting of a halogen atom, a hydroxyl group, a lower alkyl group and a lower alkoxy group; R$^h$ is a lower alkyl group, a lower alkoxy group, a lower alkoxy-lower alkyloxy group, a lower alkenyloxy group, a lower alkynyloxy group, or a group represented by —O—(CH$_2$)$_n$—Het; R$^u$ is a lower alkyl group, or a lower alkenyl group; Het is a heterocyclic group; n is an integer of from 1 to 3; W is an oxygen atom, a sulfur atom, or a group represented by —CHR$^j$— or —NR$^k$—; and each of R$^j$ and R$^k$ which are the same or different, is a hydrogen atom, or a lower alkyl group], is included in the compound represented by the general formula (I).

Further, the compound of the present invention may have stereoisomers such as optical isomers, diastereomers or geometrical isomers, depending upon the form of its substituents. The compound of the present invention includes all of such stereoisomers and their mixtures.

Now, processes for producing compounds of the present invention will be described.

The compound (I) of the present invention can be produced, for example, by the following processes or methods shown in Examples. However, the process for producing the compound (I) of the present invention is not limited to such reaction examples.

Process 1

A compound represented by the general formula (I) can be produced by reacting a compound represented by the general formula (II):

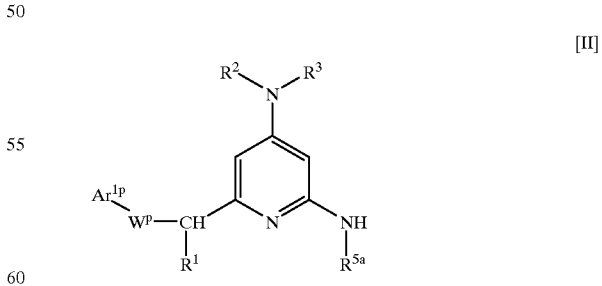

[II]

[wherein Ar$^{1p}$ is an aryl group or an aromatic heterocyclic group, which may be substituted by a group selected from the group consisting of a lower alkyl group, a lower hydroxyalkyl group which may be protected, a lower alkylene group and a group represented by —NR$^{ap}$R$^{bp}$; each of R$^{ap}$ and R$^{bp}$ which are the same or different, is a protecting group for an amino group, a hydrogen atom or a lower alkyl group; $R^{5a}$ is a hydrogen atom, a lower alkanoyl group, a trifluoroacetyl group or a lower alkoxycarbonyl group; $W^p$ is an oxygen atom, a sulfur atom, or a group represented by —CHR$^j$— or —NR$^{kp}$—; $R^{kp}$ is a protecting group for an amino group, a hydrogen atom or a lower alkyl group; and $R^1$, $R^2$, $R^3$ and $R^j$ are as defined above] with a compound represented by the general formula (III):

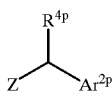

[III]

[wherein $R^{4p}$ is a hydrogen atom, or a lower alkyl group which may be substituted by a group selected from the group consisting of a lower alkoxycarbonyl group and a group selected from the group consisting of a hydroxyl group, an amino group and a carbamoyl group, which may be protected; $Ar^{2p}$ is an aryl group or an aromatic heterocyclic group, which may be substituted by a group selected from the group consisting of a halogen atom, a lower alkyl group, a lower haloalkyl group, a lower alkoxy group, a lower alkylthio group, a lower alkoxy-lower alkyl group, a group represented by —NR$^{cp}$R$^{dp}$ and a group represented by —NR$^{ep}$—CO—NR$^{fp}$R$^{gp}$, as well as a hydroxyl group and a lower hydroxyalkyl group, which may be protected; $R^{cp}$ is a protecting group for an amino group, a hydrogen atom, or a lower alkyl group; $R^{dp}$ is a protecting group for an amino group, a hydrogen atom, a lower alkyl group, a group represented by —CO—R$^h$ or —SO$_2$—R$^i$, or a heterocyclic group which may be substituted by a group selected from the group consisting of a halogen atom, a hydroxyl group which may be protected, a lower alkyl group and a lower alkoxy group; each of $R^{ep}$ and $R^{fp}$ which are the same or different, is a protecting group for an amino group, a hydrogen atom or a lower alkyl group; $R^{gp}$ is a protecting group for an amino group, a hydrogen atom, a lower alkyl group, a lower alkenyl group, or an aryl group or an aromatic heterocyclic group, which may be substituted by a group selected from the group consisting of a halogen atom, a hydroxyl group which may be protected, a lower alkyl group and a lower alkoxy group; Z is a leaving group; and $R^h$ and $R^i$ are as defined above] to obtain a compound represented by the general formula (IV):

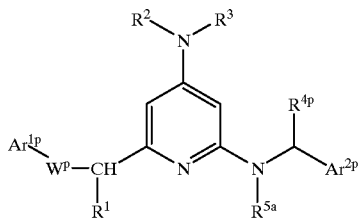

[IV]

[wherein $Ar^{1p}$, $Ar^{2p}$, $R^1$, $R^2$, $R^3$, $R^{4p}$, $R^{5a}$ and $W^p$ are as defined above], and if necessary, removing any protecting group.

As the leaving group represented by Z, a halogen atom such as a chlorine atom, a bromine atom or an iodine atom, an organic sulfonyl group such as a methanesulfonyl group, an ethanesulfonyl group or a benzenesulfonyl group, or an organic sulfonyloxy group such as a methanesulfonyloxy group, a trifluoromethanesulfonyloxy group or a p-toluenesulfonyloxy group, may, for example, be mentioned.

In the above reaction, when an amino group (or an imino group), a hydroxyl group or the like, which is not involved in the reaction, is present in the reactants, it is preferred that such an amino group (or an imino group) or a hydroxyl group, may suitably be protected by a protecting group for an amino group or by a protecting group for a hydroxyl group, then, the reaction is carried out, and such a protecting group is removed after the reaction.

Further, it is particularly preferred to use a compound wherein $R^{5a}$ is a lower alkanoyl group, a trifluoroacetyl group or a lower alkoxycarbonyl group for the reaction and to remove such a protecting group after the reaction.

As the protecting group for an amino group, an aralkyl group such as a benzyl group, a p-methoxybenzyl group, a 3,4-dimethoxybenzyl group, an o-nitrobenzyl group, a p-nitrobenzyl group, a benzhydryl group or a trityl group; a lower alkanoyl group such as a formyl group, an acetyl group, a propionyl group, a butyryl group or a pivaloyl group; a benzoyl group; an arylalkanoyl group such as a phenylacetyl group or a phenoxyacetyl group; a lower alkoxycarbonyl group such as a methoxycarbonyl group, an ethoxycarbonyl group, a propyloxycarbonyl group or a tert-butoxycarbonyl group; an aralkyloxycarbonyl group such as a benzyloxycarbonyl group, a p-nitrobenzyloxycarbonyl group or a phenetyloxycarbonyl group; a lower alkylsilyl group such as a trimethylsilyl group or a tert-butyldimethylsilyl group; a phthaloyl group, for example, having $R^{cp}$ and $R^{dp}$, or $R^{fp}$ and $R^{gp}$, put together; or an aralkylidene group such as a benzylidene group, a p-chlorobenzylidene group or an o-nitrobenzylidene group, may, for example, be mentioned, and an acetyl group, a pivaloyl group, a benzoyl group, an ethoxycarbonyl group or a tert-butoxycarbonyl group is, for example, particularly preferred.

As the protecting group for a hydroxyl group, a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group or a trityl group; or an acyl group such as a formyl group or an acetyl group, may, for example, be mentioned, and a methoxymethyl group, a tetrahydropyranyl group, a trityl group, a trimethylsilylethoxymethyl group, a tert-butyldimethylsilyl group or an acetyl group is, for example, particularly preferred.

The reaction of the compound represented by the general formula (II) with the compound represented by the general formula (III) is conducted usually by using both of the compounds (II) and (III) in equimolar amounts or either one of them in a small excess molar amount and usually in an inert solvent which does not adversely affect the reaction.

As such an inert solvent, an ether such as tetrahydrofuran or dioxane, a halogenated hydrocarbon such as methylene chloride or chloroform, or an aprotic polar solvent such as dimethylformamide, N,N-dimethylacetamide or acetonitrile, is, for example, preferred.

Further, the above reaction is preferably carried out in the presence of a base, and as such a base, in a case where $R^{5a}$ is a hydrogen atom, an organic base such as triethylamine, diisopropylethylamine, pyridine or 4-dimethylaminopyridine, or an inorganic base such as sodium hydroxide, sodium carbonate, potassium carbonate or sodium hydrogen carbonate, is, for example, preferred, and in a case where $R^{5a}$ is a lower alkanoyl group, a trifluoroacetyl group or a lower alkoxycarbonyl group, a strong base such as sodium hydride or lithium diisopropylamide, is, for example, preferred.

The amount of the base is 1 mol or an excess molar amount, preferably from 1 to 2 mols, per mol of the compound represented by the general formula (II).

The reaction temperature is usually from −78° C. to 100° C., preferably from 0° C. to 70° C.

The reaction time is usually from 5 minutes to 7 days, preferably from 30 minutes to 24 hours.

After completion of the reaction, conventional treatment is carried out to obtain a crude product of the compound represented by the general formula (IV). The compound represented by the general formula (IV) thus obtained, may or may not be purified in accordance with a conventional method, and if necessary, reactions for removing protecting groups for an amino group and a hydroxyl group as well as protecting groups in a case where $R^{5a}$ is a lower alkanoyl group, a trifluoroacetyl group or a lower alkoxycarbonyl group, may be carried out in a proper combination to obtain a compound of the general formula (I).

Removal of protecting groups may vary depending upon their types, but can be conducted in accordance with the methods disclosed in a literature [Protective Groups in Organic Synthesis, T. W. Greene, John Wiley & Sons (1981)] or methods similar thereto, for example by solvolysis employing an acid or a base, i.e. a method of reacting from 0.01 mol to a large excess amount of an acid, preferably trifluoroacetic acid, formic acid, hydrochloric acid or the like, or from an equimolar amount to a large excess amount of a base, preferably potassium hydroxide, calcium hydroxide or the like; by chemical reduction employing a metal hydride complex or the like, or by catalytic reduction employing a palladium-carbon catalyst, a Raney nickel catalyst or the like.

Process 2

A compound represented by the general formula (I-1):

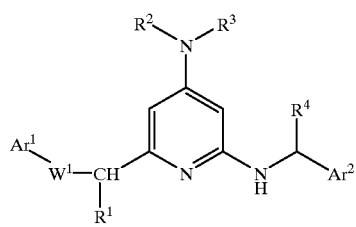

[wherein $W^1$ is an oxygen atom, a sulfur atom or a group represented by —NR—; and $Ar^1, Ar^2, R^1, R^2, R^3, R^4$ and $R^k$ are as defined above] can be produced by reacting a compound represented by the general formula (V):

$$Ar^{1p}—W^{1a}—H \quad (V)$$

[wherein $W^{1a}$ is an oxygen atom, a sulfur atom or a group represented by —$NR^{ka}$—; $R^{ka}$ is a hydrogen atom, a lower alkyl group, a lower alkanoyl group, a trifluoroacetyl group or a lower alkoxycarbonyl group; $Ar^{1p}$ is as defined above] with a compound represented by the general formula (VI):

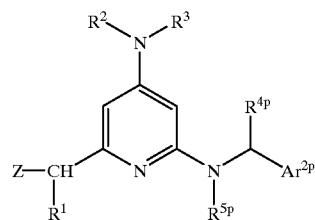

[wherein $R^{5p}$ is a protecting group for an amino group, or a hydrogen atom; and $Ar^{2p}, R^1, R^2, R^3, R^{4p}$ and Z are as defined above] to obtain a compound represented by the general formula (VII):

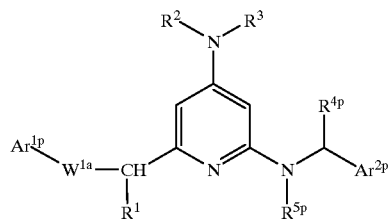

[wherein $Ar^{1p}, Ar^{2p}, R^1, R^2, R^3, R^{4p}, R^{5p}$ and $W^{1a}$ are as defined above], and if necessary, removing any protecting group.

Process 2 is a process for producing a compound represented by the general formula (I) of the present invention, wherein W is an oxygen atom, a sulfur atom or a group represented by —$NR^k$—, i.e. a compound represented by the general formula (I-1).

The reaction of the compound represented by the general formula (V) with the compound represented by the general formula (VI) is carried out usually in an inert solvent which does not adversely affect the reaction, using both of the compounds (V) and (VI) in equimolar amounts or either one of them in a small excess molar amount. Further, this reaction may be carried out in the presence of a base in order to let the reaction proceed smoothly.

As such an inert solvent, an ether such as tetrahydrofuran or dioxane, a halogenated hydrocarbon such as methylene chloride or chloroform, an aromatic hydrocarbon such as benzene or toluene or an aprotic polar solvent such as dimethylformamide, N,N-dimethylacetamide or acetonitrile, is preferred.

As the base, an inorganic salt such as sodium hydride, sodium hydroxide, potassium hydroxide, sodium carbonate, potassium carbonate or sodium hydrogen carbonate or an organic base such as pyridine, 4-dimethylaminopyridine, triethylamine or diisopropylethylamine, is preferred, and such a base is used usually in an equal molar or excess molar amount, preferably from 1 to 5 mols, per mol of the compound (V) or the compound (VI).

The reaction temperature is usually from −70 to 100° C., preferably from −20° C. to 50° C.

The reaction time is usually from 5 minutes to 7 days, preferably from 1 to 24 hours.

After completion of the reaction, conventional treatment may be carried out as it is when no protecting group is present in the product, or after removing any protecting group, when such a protecting group is present in the product, to obtain a compound of the general formula (I-1).

For removal of protecting groups and post treatment, etc., the methods described in the above Process 1 can be applied as they are.

Process 3

A compound represented by the general formula (I-2):

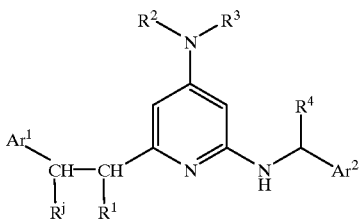

[I-2]

[wherein $Ar^1$, $Ar^2$, $R^1$, $R^2$, $R^3$, $R^4$ and $R^j$ are as defined above] can be obtained by reacting a compound represented by the general formula (VIII):

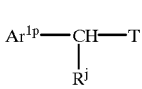

[VIII]

[wherein T is a triphenylphosphonio group, a dimethoxyphosphoryl group or a diethoxyphosphoryl group; and $Ar^{1p}$ and $R^j$ are as defined above] with a compound represented by the general formula (IX):

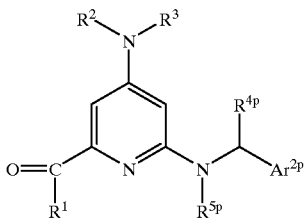

[IX]

[wherein $Ar^{2p}$, $R^1$, $R^2$, $R^3$, $R^{4p}$ and $R^{5p}$ are as defined above] to obtain a compound represented by the general formula (X):

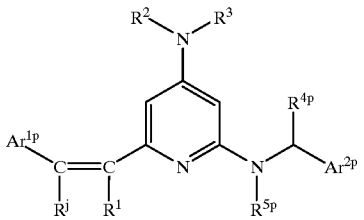

[X]

[wherein $Ar^{1p}$, $Ar^{2p}$, $R^1$, $R^2$, $R^3$, $R^{4p}$, $R^{5p}$ and $R^j$ are as defined above], then reducing the compound (X), and if necessary, removing any protecting group.

Process 3 is a process for producing a compound represented by the general formula (I) of the present invention, wherein W is a group represented by —CHR$^j$—, i.e. a compound represented by the general formula (I-2).

The reaction of the compound represented by the general formula (VIII) with the compound represented by the general formula (IX), is carried out usually by using both in equimolar amounts or either one of them in a small excess molar amount.

The reaction is carried out usually in an inert solvent, and as such an inert solvent, an ether such as ethyl ether, tetrahydrofuran or dioxane, an aromatic hydrocarbon such as benzene, toluene, chlorobenzene or xylene, an aprotic polar solvent such as dimethylformamide, ethyl acetate, hexamethylphosphoric triamide, or a mixed solvent thereof, may, for example, be mentioned.

The reaction temperature is usually from −100° C. to the boiling point of the solvent used for the reaction, preferably from −70° C. to 50° C.

The reaction time is usually from 5 minutes to 7 days, preferably from 10 minutes to 24 hours.

Further, the above reaction is preferably carried out in the presence of a base, and as such a base, sodium hydride, n-butyl lithium, sodium methoxide, potassium tert-butoxide, sodium hydroxide or potassium hydroxide may, for example, be mentioned.

The amount of the base is from 1 mol to an excess mol, preferably from 1 to 5 mols, per mol of the compound represented by the general formula (VIII).

Then, the reaction for reducing the compound (X) obtained by the above process, is preferably carried out by catalytic reduction employing a palladium-carbon catalyst, a Raney nickel catalyst or a platinum catalyst, usually in an inert solvent.

As the inert solvent, an alcohol such as methanol, ethanol or propanol, or acetic acid, may, for example, be mentioned.

The reaction temperature is usually from −20° C. to 100° C., preferably from 0° C. to room temperature.

The reaction time is usually from 5 minutes to 7 days, preferably from 10 minutes to 24 hours.

The hydrogen pressure in the catalytic reduction reaction is usually preferably from atmospheric pressure to 5 atm, and the amount of the catalyst is usually from 0.01 to 1 mol, preferably from 0.05 to 0.2 mol, per mol of the starting material compound (X).

After completion of the reaction, conventional treatment is carried out as it is when no protecting group is present in the product, or after removing any protecting group, when such a protecting group is present in the product, to obtain a compound of the general formula (I-2).

For removal of protecting groups and post treatment, etc., the methods described in the above Process 1 can be applied as they are.

Process 4

A compound represented by the general formula (I-2):

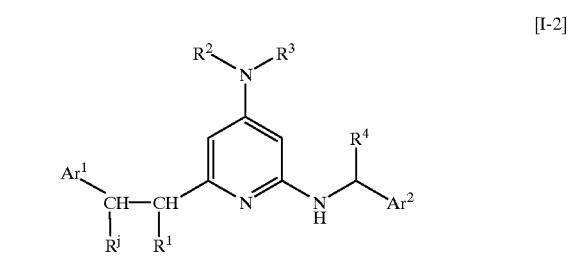

[I-2]

[wherein $Ar^1$, $Ar^2$, $R^1$, $R^2$, $R^3$, $R^4$ and $R^j$ are as defined above] can be obtained by reacting a compound represented by the general formula (XI):

[XI]

[wherein $Ar^{1p}$ and $R^j$ are as defined above] with a compound represented by the general formula (XII):

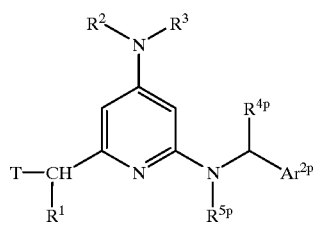

[XII]

[wherein $Ar^{2p}$, $R^1$, $R^2$, $R^3$, $R^{4p}$, $R^{5p}$ and T are as defined above] to obtain a compound represented by the general formula (X):

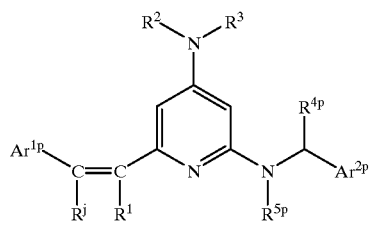

[X]

[wherein $Ar^{1p}$, $Ar^{2p}$, $R^1$, $R^2$, $R^3$, $R^{4p}$, $R^{5p}$ and $R^j$ are as defined above], then reducing the compound (X), and if necessary, removing any protecting group.

Like the above Process 3, Process 4 is a process for producing a compound represented by the general formula (I) of the present invention, wherein W is a group represented by —$CHR^j$—, i.e. a compound represented by the general formula (I-2).

Process 4 is equal to a reaction wherein the compounds (VIII) and (IX) as the starting compounds in Process 3 are replaced by the compounds (XII) and (XI), respectively. Accordingly, the reaction methods and conditions, etc., may all be in accordance with Process 3.

Process 5

A compound represented by the general formula (I-3):

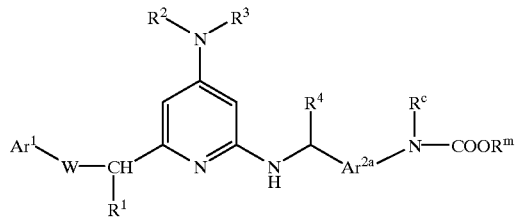

[I-3]

[wherein $Ar^{2a}$ is an aryl group or an aromatic heterocyclic group, which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group; and $Ar^1$, $R^1$, $R^2$, $R^3$, $R^4$, $R^c$, $R^m$ and W are as defined above] can be obtained by reacting a compound represented by the general formula (XIII):

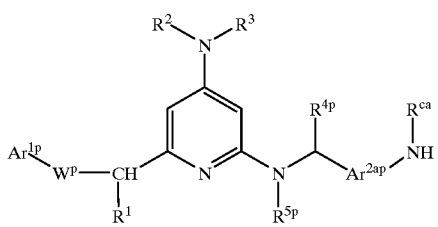

[XIII]

[wherein $Ar^{2ap}$ is an aryl group or an aromatic heterocyclic group, which may be substituted by a group selected from the group consisting of a halogen atom, a lower alkyl group, a lower haloalkyl group, a lower alkoxy group, a lower alkylthio group and a lower alkoxy-lower alkyl group, as well as a hydroxyl group and a lower hydroxyalkyl group, which may be protected; $R^{ca}$ is a hydrogen atom, a lower alkyl group, a lower alkanoyl group, a trifluoroacetyl group or a lower alkoxycarbonyl group; and $Ar^1$, $R^1$, $R^2$, $R^3$, $R^{4p}$, $R^{5p}$ and $W^p$ are as defined above] with a compound represented by the general formula (XIV):

X—COOR$^m$ (XIV)

[wherein $R^m$ is a lower alkyl group, a lower alkenyl group, a lower alkynyl group or a group represented by —O—$(CH_2)_n$—Het; X is a halogen atom or a group represented by $R^m$O—; and Het and n are as defined above] to obtain a compound represented by the general formula (XV):

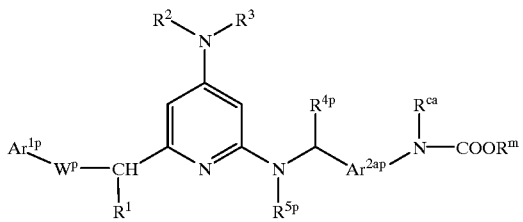

[XV]

[wherein $Ar^{1p}$, $Ar^{2ap}$, $R^1$, $R^2$, $R^3$, $R^{4p}$, $R^{5p}$, $R^{ca}$, $R^m$ and $W^p$ are as defined above], and if necessary, removing any protecting group.

Process 5 is a process for producing a compound represented by the general formula (I) of the present invention, wherein $Ar^2$ is an aryl group or an aromatic heterocyclic group, which has a group represented by —$NR^c$—$COOR^m$ (wherein $R^c$ and $R^m$ are as defined above) and which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group, i.e. a compound represented by the general formula (I-3).

The reaction of the compound represented by the general formula (XIII) with the compound represented by the general formula (XIV) is carried out usually by using the compound represented by the general formula (XIV) in an amount of from 1 mol to an excess mol, preferably from 1 to 2 mols, per mol of the compound represented by the general formula (XIII).

The reaction is carried out usually in an inert solvent, and as such an inert solvent, methylene chloride, chloroform, tetrahydrofuran, ethyl ether, benzene, toluene, dimethylformamide or a mixed solvent thereof, is for example preferred.

The reaction temperature is usually from −78° C. to 100° C., preferably from −20° C. to 50° C.

The reaction time is usually from 5 minutes to 7 days, preferably from 30 minutes to 24 hours.

Further, the above reaction is preferably carried out in the presence of a base, and as such a base, in a case where $R^{ca}$ is a hydrogen atom or a lower alkyl group, an organic base such as triethylamine, diisopropylamine, pyridine or 4-dimethylaminopyridine, or an inorganic base such as sodium hydroxide, sodium carbonate, potassium carbonate or sodium hydrogen carbonate, is preferred, and in the case where $R^{ca}$ is a lower alkanoyl group, a trifluoroacetyl group or a lower alkoxycarbonyl group, a strong base such as sodium hydride or lithium diisopropylamide is, for example, preferred.

The amount of the base is usually from 1 mol to an excess mol, preferably from 1 to 2 mols, per mol of the compound represented by the general formula (XIII).

Further, in a case where $R^{ca}$ is a lower alkanoyl group, a trifluoroacetyl group or a lower alkoxycarbonyl group, the reaction may be carried out in a two phase system comprising water and a solvent immiscible with water, such as ether, benzene or toluene, by using an inorganic base such as sodium hydroxide, potassium hydroxide, sodium carbonate or potassium carbonate and using a phase transfer catalyst such as tetrabutylammonium hydrogen sulfate.

After completion of the reaction, conventional treatment is carried out as it is when no protecting group is present in the product, or after removing a protecting group, when a protecting group for a hydroxyl group or an amino group, or a protecting group such as a lower alkanoyl group, a trifluoroacetyl group or a lower alkoxycarbonyl group as $R^{ca}$, is present in the product, to obtain a compound of the general formula (I-3).

Such a protecting group can be removed usually by a conventional method well known in the field of the organic chemistry, such as a method of reacting from 0.01 mol to a large excess amount of an acid or from an equimolar amount to a large excess amount of a base.

As such an acid, trifluoroacetic acid, formic acid or hydrochloric acid may, for example, be preferred, and as the base, potassium hydroxide or calcium hydroxide may, for example, be preferred.

Process 6

A compound represented by the general formula (I-3):

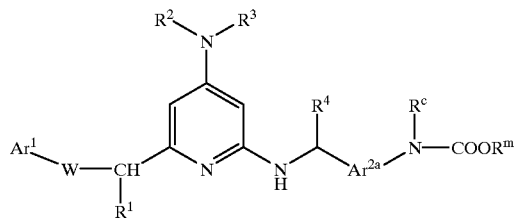

[I-3]

[wherein $Ar^1$, $Ar^{2a}$, $R^1$, $R^2$, $R^3$, $R^4$, $R^c$, $R^m$ and W are as defined above] can be obtained by reacting a compound represented by the general formula (XIII):

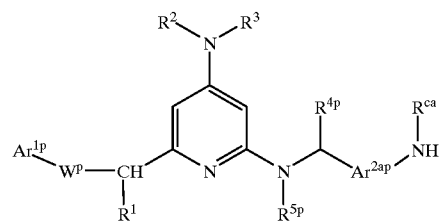

[XIII]

[wherein $Ar^{1p}$, $Ar^{2ap}$, $R^1$, $R^2$, $R^3$, $R^{4p}$, $R^{5p}$, $R^{ca}$ and $W^p$ are as defined above] with a compound represented by the general formula (XVI):

$$X^1\text{—CO—}X^2 \qquad (XVI)$$

[wherein $X^1$ and $X^2$ which are the same or different, is a halogen atom, a 1-imidazolyl group or a phenoxy group which may be substituted by a halogen atom or a nitro group] to obtain a compound represented by the general formula (XVII):

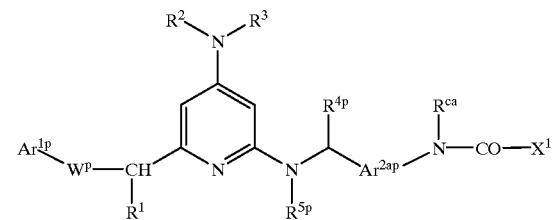

[XVII]

[wherein $Ar^{1p}$, $Ar^{2ap}$, $R^1$, $R^2$, $R^3$, $R^{4p}$, $R^{5p}$, $R^{ca}$, $W^p$ and $X^1$ are as defined above], then reacting the compound (XVII) with a compound represented by the general formula (XVIII):

$$R^m OH \qquad (XVIII)$$

[wherein $R^m$ is as defined above] to obtain a compound represented by the general formula (XV):

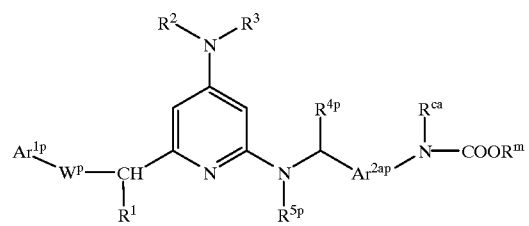

[XV]

[wherein $Ar^{1p}$, $Ar^{2ap}$, $R^1$, $R^2$, $R^3$, $R^{4p}$, $R^{5p}$, $R^{ca}$, $R^m$ and $W^p$ are as defined above], and if necessary, removing any protecting group.

Like the above Process 5, Process 6 is a process for producing a compound represented by the general formula (I) of the present invention, wherein $Ar^2$ is an aryl group or an aromatic heterocyclic group, which has a group represented by —$NR^c$—$COOR^m$ (wherein $R^c$ and $R^m$ are as defined above) and which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group, i.e. a compound represented by the general formula (I-3).

The reaction of the compound represented by the general formula (XIII) with the compound represented by the general formula (XVI), can be carried out substantially in the same manner as the reaction of the compound represented by the general formula (XIII) with the compound represented by the general formula (XIV) in the above Process 5.

The reaction of the compound represented by the general formula (XVII) with the compound represented by the general formula (XVIII) is carried out by isolating or without isolating the compound represented by the general formula (XVII) obtained by the above-mentioned reaction and usually by using the compound represented by the general formula (XVIII) in an amount of from 1 mol to a large excess molar amount, preferably from 1 to a large excess molar amount of at least 5 mols, per mol of the compound (XVII).

The reaction is carried out usually in an inert solvent, or using the compound represented by the general formula (XVIII) as the solvent and the reactant, and as such an inert solvent, methylene chloride, chloroform, tetrahydrofuran, dimethylformamide or a mixed solvent thereof, is, for example, preferred.

The reaction temperature is usually from −30° C. to 200° C., preferably from −20° C. to 100° C.

The reaction time is usually from 5 minutes to 7 days, preferably from 30 minutes to 24 hours.

Further, the above reaction is preferably carried out in the presence of a base, and as such a base, sodium hydride, lithium hydride, a sodium alkoxide of the alcohol (XVIII) used as the starting material, sodium hydroxide, sodium carbonate, triethylamine, diisopropylethylamine, pyridine or 4-dimethylaminopyridine is, for example, preferred.

The amount of the base is from 1 mol to an excess mol, preferably from 1 to 5 mols, per mol of the compound represented by the general formula (XVII).

After completion of the reaction, conventional treatment may be carried out as it is in a case where no protecting group is present in the product, or after removing any protecting group, when such a protecting group is present in the product, to obtain a compound of the general formula (I-3).

For removal of protecting groups and post treatment, etc., the methods described in the above Process 5 can be applied as they are.

Process 7

A compound represented by the general formula (I-4):

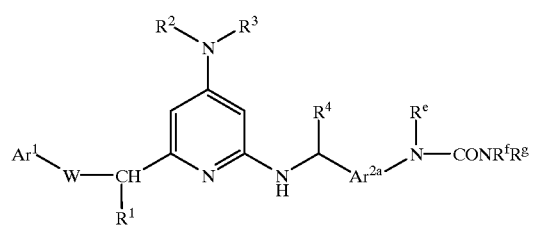

[I-4]

[wherein $Ar^1$, $Ar^{2a}$, $R^1$, $R^2$, $R^3$, $R^4$, $R^e$, $R^f$, $R^g$ and W are as defined above] can be obtained by reacting a compound represented by the general formula (XVII'):

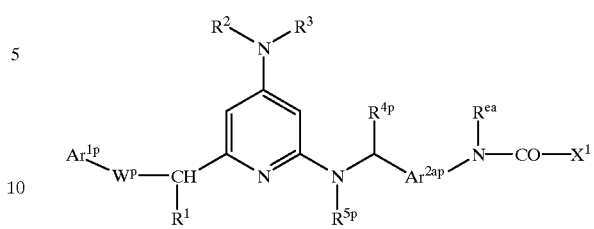

[XVII']

[wherein $R^{ea}$ is a hydrogen atom, a lower alkyl group, a lower alkanoyl group, a trifluoroacetyl group or a lower alkoxycarbonyl group; and $Ar^{1p}$, $Ar^{2ap}$, $R^1$, $R^2$, $R^3$, $R^{4p}$, $R^{5p}$, $W^p$ and $X^1$ are as defined above] with a compound represented by the general formula (XIX):

$R^f R^{gpa} NH$ (XIX)

[wherein $R^{gpa}$ is a hydrogen atom, a lower alkyl group, a lower alkenyl group, or an aryl group or an aromatic heterocyclic group, which may be substituted by a group selected from the group consisting of a halogen atom, a hydroxyl group which may be protected, a lower alkyl group and a lower alkoxy group; and $R^f$ is as defined above] to obtain a compound represented by the general formula (XX):

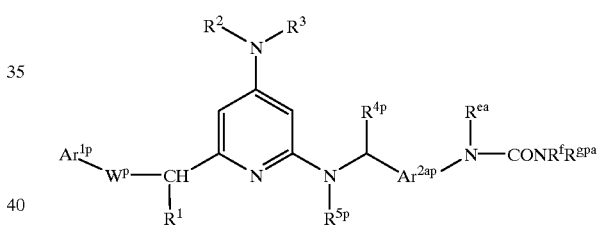

[XX]

[wherein $Ar^{1p}$, $Ar^{2ap}$, $R^1$, $R^2$, $R^3$, $R^{4p}$, $R^{5p}$, $R^{ea}$, $R^f$, $R^{gpa}$ and $W^p$ are as defined above], and if necessary, removing any protecting group.

Process 7 is a process for producing a compound represented by the general formula (I) of the present invention, wherein $Ar^2$ is an aryl group or an aromatic heterocyclic group, which has a group represented by —$NR^e$—CO—$NR^f R^g$ (wherein $R^e$, $R^f$ and $R^g$ are as defined above) and which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group, i.e. a compound represented by the general formula (I-4).

The reaction of the compound represented by the general formula (XVII') with the compound represented by the general formula (XIX) is carried out usually by using the compound represented by the general formula (XIX) in an amount of from 1 mol to a large excess mol, preferably from 1 to 10 mols, per mol of the compound represented by the general formula (XVII').

The reaction is carried out usually in an inert solvent, and as such an inert solvent, methylene chloride, tetrahydrofuran, dimethylformamide is, for example, preferred.

The reaction temperature is usually from −30° C. to 100° C., preferably from −20° C. to 50° C.

The reaction time is usually from 5 minutes to 7 days, preferably from 30 minutes to 24 hours.

Further, the above reaction can be carried out in the presence of a base to let the reaction proceed smoothly, and as such a base, an inorganic base such as sodium hydride, lithium diisopropylamide, sodium hydroxide, sodium carbonate or potassium carbonate, or an organic base such as triethylamine, diisopropylethylamine, pyridine or 4-dimethylaminopyridine, is, for example, preferred.

The amount of the base is from 1 mol to an excess mol, preferably from 1 to 10 mols, per mol of the compound represented by the general formula (XVII').

Further, it is possible to use a large excess amount of the amine (XIX) as the starting material instead of said base.

After completion of the reaction, conventional treatment is carried out as it is, when no protecting group is present in the product, or after removing a protecting group, when a protecting group for a hydroxyl group or an amino group, or a protecting group such as a lower alkanoyl group, a trifluoroacetyl group or a lower alkoxycarbonyl group as $R^{ea}$, is present in the product, to obtain a compound of the general formula (I-4).

For removal of the protecting groups and post treatment, etc., the methods described in the above Process 5 can be applied as they are.

Process 8

A compound represented by the general formula (I-5):

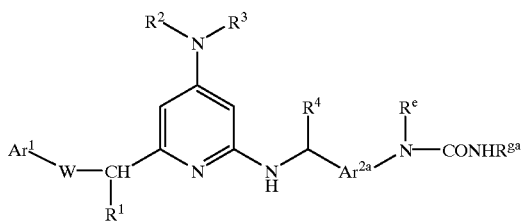

[I-5]

[wherein $Ar^1$, $Ar^{2a}$, $R^1$, $R^2$, $R^3$, $R^4$, $R^e$, $R^{ga}$ and W are as defined above] can be obtained by reacting a compound represented by the general formula (XXI):

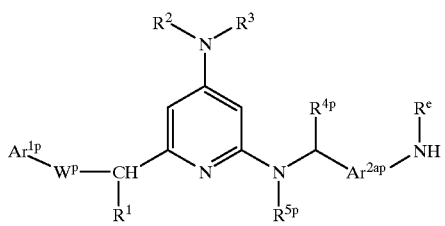

[XXI]

[wherein $Ar^{1p}$, $Ar^{2ap}$, $R^1$, $R^2$, $R^3$, $R^{4p}$, $R^{5p}$, $R^e$ and $W^p$ are as defined above] with a compound represented by the general formula (XXII):

$R^{gap}$—NCO    (XXII)

[wherein $R^{gap}$ is a lower alkyl group, a lower alkenyl group, or an aryl group or an aromatic heterocyclic group, which may be substituted by a group selected from the group consisting of a halogen atom, a hydroxyl group which may be protected, a lower alkyl group and a lower alkoxy group] to obtain a compound represented by the general formula (XXIII):

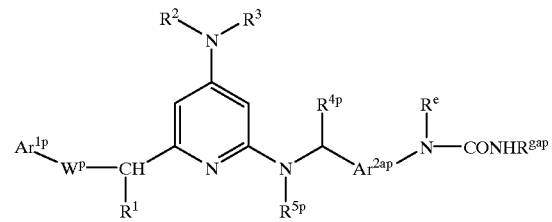

[XXIII]

[wherein $Ar^{1p}$, $Ar^{2ap}$, $R^1$, $R^2$, $R^3$, $R^{4p}$, $R^{5p}$, $R^e$, $R^{gap}$ and $W^p$ are as defined above], and if necessary, removing any protecting group.

Process 8 is a process for producing a compound represented by the general formula (I) of the present invention, wherein $Ar^2$ is an aryl group or an aromatic heterocyclic group, which has a group represented by —$NR^e$—CO—$NHR^{ga}$ (wherein $R^e$ and $R^{ga}$ are as defined above) and which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group, i.e. a compound represented by the general formula (I-5).

The reaction of the compound represented by the general formula (XXI) with the compound represented by the general formula (XXII) is carried out usually by using the compound represented by the general formula (XXII) in an amount of from 1 mol to an excess mol, preferably from 1 to 2 mols, per mol of the compound (XXI).

The reaction is carried out usually in an inert solvent, and as such an inert solvent, methylene chloride, chloroform, tetrahydrofuran, benzene, dimethylformamide or a mixed solvent thereof, is, for example, preferred.

The reaction temperature is usually from −78° C. to 100° C., preferably from −20° C. to 50° C.

The reaction time is usually from 5 minutes to 7 days, preferably from 30 minutes to 24 hours.

Further, the above reaction can be carried out in the presence of a base to let the reaction proceed smoothly, and as such a base, an organic base such as triethylamine, diisopropylethylamine, pyridine or 4-dimethylaminopyridine, is preferred.

The amount of the base is from a catalytic amount to an excess mol, per mol of the compound represented by the general formula (XXI).

After completion of the reaction, conventional treatment is carried out as it is when no protecting group is present in the product, or after removing any protecting group, when such a protecting group is present in the product, to obtain a compound of the general formula (I-5).

For removal of the protecting groups and post treatment, etc., the methods described in the above Process 5 can be applied as they are.

Process 9

A compound represented by the general formula (I-6):

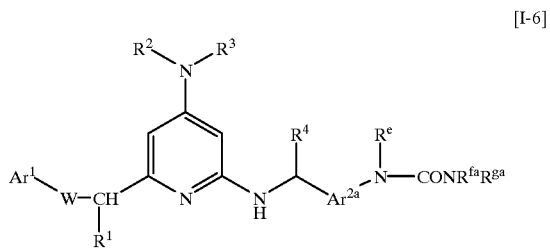

[I-6]

[wherein $Ar^1$, $Ar^{2a}$, $R^1$, $R^2$, $R^3$, $R^4$, $R^e$, $R^{fa}$, $R^{ga}$ and W are as defined above] can be obtained by reacting a compound represented by the general formula (XIII'):

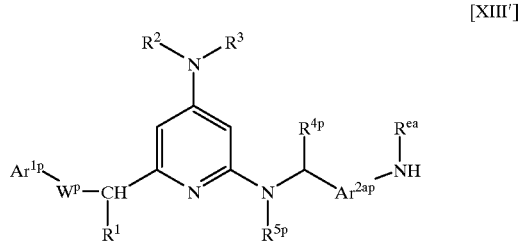

[XIII']

[wherein $Ar^{1p}$, $Ar^{2ap}$, $R^1$, $R^2$, $R^3$, $R^{4p}$, $R^{5p}$, $R^{ea}$ and $W^p$ are as defined above] with a compound represented by the general formula (XXIV):

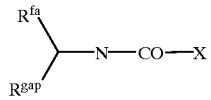

[XXIV]

[wherein $R^{fa}$ is a lower alkyl group; and $R^{gap}$ and X are as defined above] to obtain a compound represented by the general formula (XXV):

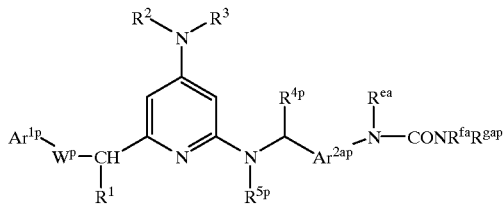

[XXV]

[wherein $Ar^{1p}$, $Ar^{2ap}$, $R^1$, $R^2$, $R^3$, $R^{4p}$, $R^{5p}$, $R^{ea}$, $R^{fa}$, $R^{gap}$ and $W^p$ are as defined above], and if necessary, removing any protecting group.

Process 9 is a process for producing a compound represented by the general formula (I) of the present invention, wherein $Ar^2$ is an aryl group or an aromatic heterocyclic group, which has a group represented by —$NR^e$—CO—$NR^{fa}R^{ga}$ (wherein $R^e$, $R^{fa}$ and $R^{ga}$ are as defined above) and which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group, i.e. a compound represented by the general formula (I-6).

The reaction of the compound represented by the general formula (XIII') with the compound represented by the general formula (XXIV) can be carried out substantially in the same manner as the reaction of the compound represented by the general formula (XIII) with the compound represented by the general formula (XIV) in the above Process 5.

After completion of the reaction, conventional treatment is carried out as it is, when no protecting group is present in the product, or after removing any protecting group, when such a protecting group is present in the product, to obtain a compound of the general formula (I-6).

For removal of the protecting groups and post treatment, etc., the methods described in the above Process 5 can be applied as they are Process 10

A compound represented by the general formula (I-7):

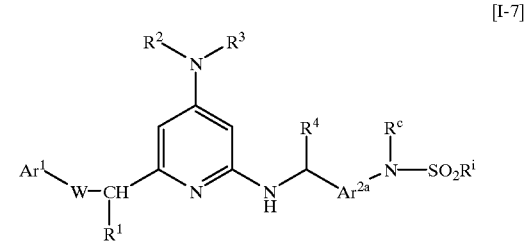

[I-7]

[wherein $Ar^1$, $Ar^{2a}$, $R^1$, $R^2$, $R^3$, $R^4$, $R^c$, $R^i$ and W are as defined above] can be obtained by reacting a compound represented by the general formula (XIII):

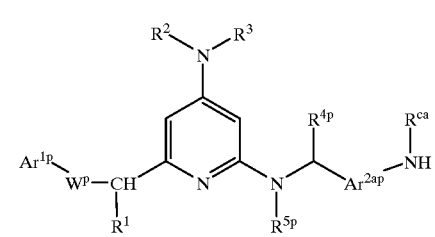

[XIII]

[wherein $Ar^{1p}$, $Ar^{2ap}$, $R^1$, $R^2$, $R^3$, $R^{4p}$, $R^{5p}$, $R^{ea}$ and $W^p$ are as defined above] with a compound represented by the general formula (XXVI):

$R^i$—$SO_2$—X  (XXVI)

[wherein $R^i$ and X are as defined above] to obtain a compound represented by the general formula (XXVII):

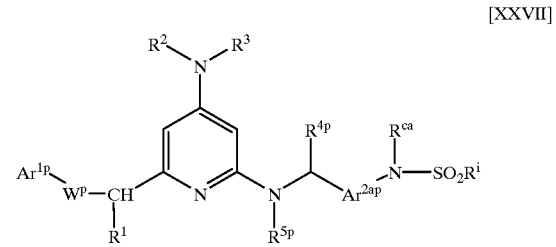

[XXVII]

[wherein $Ar^{1p}$, $Ar^{2ap}$, $R^1$, $R^2$, $R^3$, $R^{4p}$, $R^{5p}$, $R^{ca}$, $R^i$ and $W^p$ are as defined above], and if necessary, removing any protecting group.

Process 10 is a process for producing a compound represented by the general formula (I) of the present invention, wherein Ar² is an aryl group or an aromatic heterocyclic group, which has a group represented by —NR$^c$—SO$_2$—R$^i$ (wherein R$^c$ and R$^i$ are as defined above) and which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group, i.e. a compound represented by the general formula (I-7).

The reaction of the compound represented by the general formula (XIII) with the compound represented by the general formula (XXVI) can be carried out substantially in the same manner as the reaction of the compound represented by the general formula (XIII) with the compound represented by the general formula (XIV) in the above Process 5.

After completion of the reaction, conventional treatment may be carried out as it is, when no protecting group is present in the product, or after removing any protecting group, when such a protecting group is present in the product, to obtain a compound of the general formula (I-7).

For removal of the protecting groups and post treatment, etc., the methods described in the above Process 5 can be applied as they are.

Process 11

A compound represented by the general formula (I-3-1):

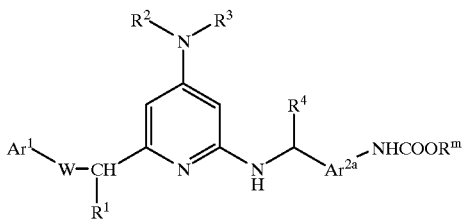

[I-3-1]

[wherein Ar$^1$, Ar$^{2a}$, R$^1$, R$^2$, R$^3$, R$^4$, R$^m$ and W are as defined above] can be obtained by reacting a carboxylic acid represented by the general formula (XXVIII):

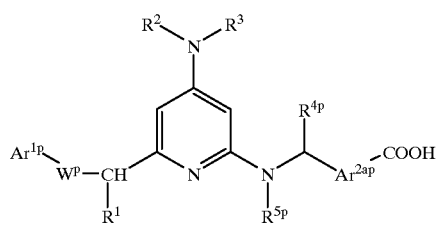

[XXVIII]

[wherein Ar$^{1p}$, Ar$^{2ap}$, R$^1$, R$^2$, R$^3$, R$^{4p}$, R$^{5p}$ and W$^p$ are a defined above] or its reactive derivative, with diphenylphosphoryl azide or sodium azide, followed by heat treatment to obtain a compound represented by the general formula (XXIX):

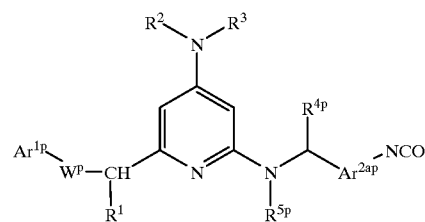

[XXIX]

[wherein Ar$^{1p}$, Ar$^{2ap}$, R$^1$, R$^2$, R$^3$, R$^{4p}$, R$^{5p}$ and W$^p$ are as defined above], then reacting the compound (XXIX) with a compound represented by the general formula (XVIII):

$$R^mOH \qquad (XVIII)$$

[wherein R$^m$ is as defined above] to obtain a compound represented by the general formula (XV-1):

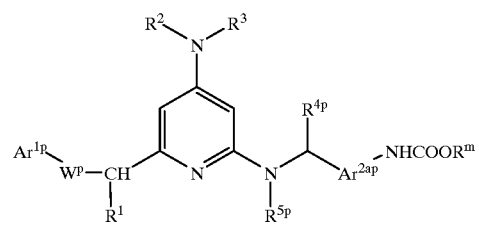

[XV-1]

[wherein Ar$^{1p}$, Ar$^{2ap}$, R$^1$, R$^2$, R$^3$, R$^{4p}$, R$^{5p}$, R$^m$ and W$^p$ are as defined above], and if necessary, removing any protecting group.

Process 11 is a process for producing a compound represented by the general formula (I) of the present invention, wherein Ar² is an aryl group or an aromatic heterocyclic group, which has a group represented by —NHCOOR$^m$ (wherein R$^m$ is as defined above) and which may be substituted by a group selected from the group consisting of a halogen atom, a hydroxyl group, a lower alkyl group, a lower haloalkyl group, a lower alkoxy group, a lower alkylthio group, a lower hydroxyalkyl group and a lower alkoxy-lower alkyl group, i.e. a compound represented by the general formula (I-3-1).

As the reactive derivative of the carboxylic acid represented by the general formula (XXVIII), an acid halide, a mixed acid anhydride, an active ester or an active amide may, for example, be employed.

The acid halide of the compound of the general formula (XXVIII) can be obtained by reacting the carboxylic acid of the formula (XXVIII) with a halogenating agent in accordance with a conventional method. As the halogenating agent, thionyl chloride, phosphorus trichloride, phosphorus pentachloride, phosphorus oxychloride, phosphorus tribromide, oxalyl chloride or phosgene may, for example, be used.

The mixed acid anhydride of the compound of the general formula (XVIII) can be obtained by reacting the carboxylic acid of the general formula (XXVIII) with e.g. an alkyl chlorocarbonate such as ethyl chlorocarbonate or an aliphatic carboxylic chloride such as acetyl chloride, in accordance with a conventional method.

The active ester of the compound of the general formula (XXVIII) can be obtained by reacting the carboxylic acid of the general formula (XXVIII) with an N-hydroxy compound such as N-hydroxysuccinimide, N-hydroxyphthalimide or 1-hydroxybenzotriazole, or a phenol compound such as 4-nitrophenol, 2,4-dinitrophenol, 2,4,5-trichlorophenol or pentachlorophenol, in the presence of a condensing agent such as N,N'-dicyclohexylcarbodiimide or 1-ethyl-3-(3-dimethylaminopropyl)carbodiimide, in accordance with a conventional method.

The active amide of the compound of the general formula (XXVIII) can be obtained by reacting the carboxylic acid of the general formula (XXVIII) with e.g. 1,1'-carbonyldiimidazole of 1,1'-carbonylbis(2-methylimidazole) in accordance with a conventional method.

The reaction of the reactive derivative of the carboxylic acid represented by the general formula (XXVIII) with sodium azide is carried out by using sodium azide in an amount of from 1 mol to an excess mol, preferably from 1 to 5 mols, per mol of the reactive derivative of the carboxylic acid represented by the general formula (XXVIII).

The reaction is carried out usually in an inert solvent, and as such an inert solvent, a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixed solvent thereof, may, for example, be mentioned.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The reaction of the carboxylic acid represented by the general formula (XXVIII) with diphenylphosphoryl azide is carried out by using diphenylphosphoryl azide in an amount of from 1 mol to an excess mol, preferably from 1 to 2 mols, per mol of the carboxylic acid represented by the general formula (XXVIII).

The reaction can be carried out usually in an inert solvent, and as such an inert solvent, chloroform, tetrahydrofuran, dioxane, toluene, dimethylformamide or a mixed solvent thereof may, for example, be mentioned.

The reaction temperature is usually from −70° C. to the boiling point of the solvent used for the reaction, preferably from −20° C. to 100° C.

The reaction time is usually from 5 minutes to 7 days, preferably from 30 minutes to 24 hours.

Further, the above reaction is preferably carried out in the presence of a base to let the reaction proceed smoothly, and as such a base, it is preferred to carry out the invention in the presence of an organic base such as triethylamine, diisopropylethylamine, pyridine or 4-dimethylaminopyridine.

The amount of the base is from 1 mol to an excess mol, preferably from 1 to 2 mols, per mol of the reactive derivative of the carboxylic acid of the general formula (XXVIII).

The reaction of the compound represented by the general formula (XXIX) with the compound represented by the general formula (XVIII) is carried out by isolating or without isolating the compound represented by the general formula (XXIX) obtained by the above-mentioned reaction and usually by using the compound represented by the general formula (XVIII) in an amount of from 1 mol to a large excess mol, preferably from 1 to 50 mols, per mol of the compound (XXIX).

The reaction is carried out usually in an inert solvent, or using the compound represented by the general formula (XVIII) as a solvent and reactant, and as such an inert solvent, tetrahydrofuran, dioxane, toluene, dimethylformamide or a mixed solvent thereof, is, for example, preferred.

The reaction temperature is usually preferably from 0° C. to 100° C., and the reaction time is usually preferably from 30 minutes to 24 hours.

After completion of the reaction, conventional treatment is carried out as it is, when no protecting group is present in the product, or after removing any protecting group, when such a protecting group is present in the product, to obtain a compound of the general formula (I-3-1).

For removal of protecting groups and post treatment, etc., the methods described in the above Process 5 can be applied as they are.

Isolation and purification of the compound of the general formula (I), (I-1), (I-2), (I-3), (I-3-1), (I-4), (I-5), (I-6) or (I-7) obtained by the above method, can be carried out by a single use or a proper combination of conventional separating means such as column chromatography employing silica gel, adsorbent resin or the like, liquid chromatography, solvent extraction and recrystallization-reprecipitation.

The compound of the general formula (I), (I-1), (I-2), (I-3), (I-3-1), (I-4), (I-5), (I-6) or (I-7) can be converted to a pharmaceutically acceptable salt by a conventional method, and reversely, the conversion from the salt to a free compound can also be conducted by a conventional method.

The compound represented by the general formula (II), (III), (V), (VI), (VIII), (IX), (XI), (XII), (XIII), (XIII'), (XIV), (XVI), (XVII'), (XVIII), (XIX), (XXI), (XXII), (XXIV), (XXVI) or (XXVIII) may be available as a commercial product, or can be produced by a conventional method or a similar thereto, or by the following processes or the methods disclosed in Examples.

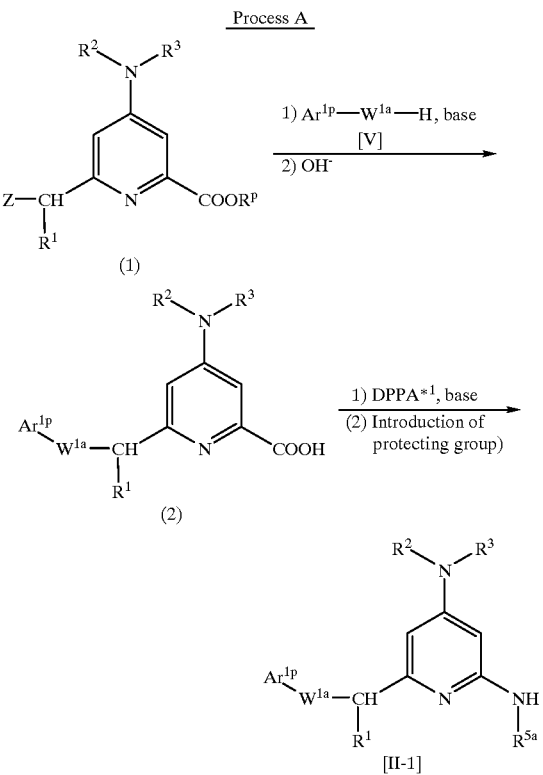

Process B
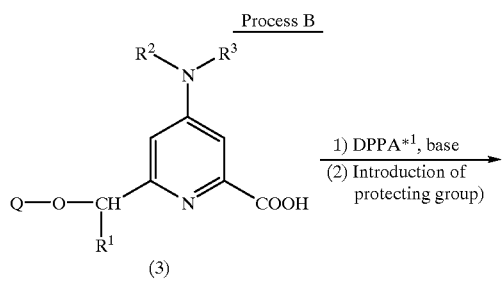
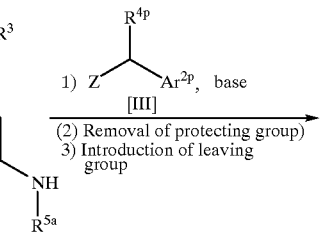
*[1] diphenylphosphoryl azide
Process C
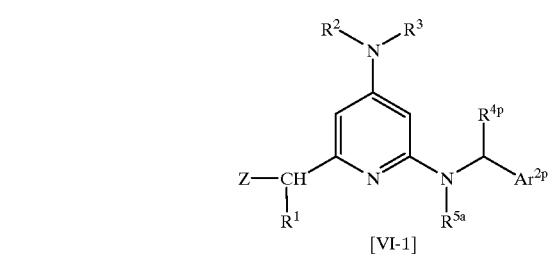
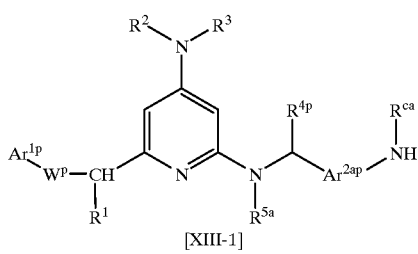
Process D
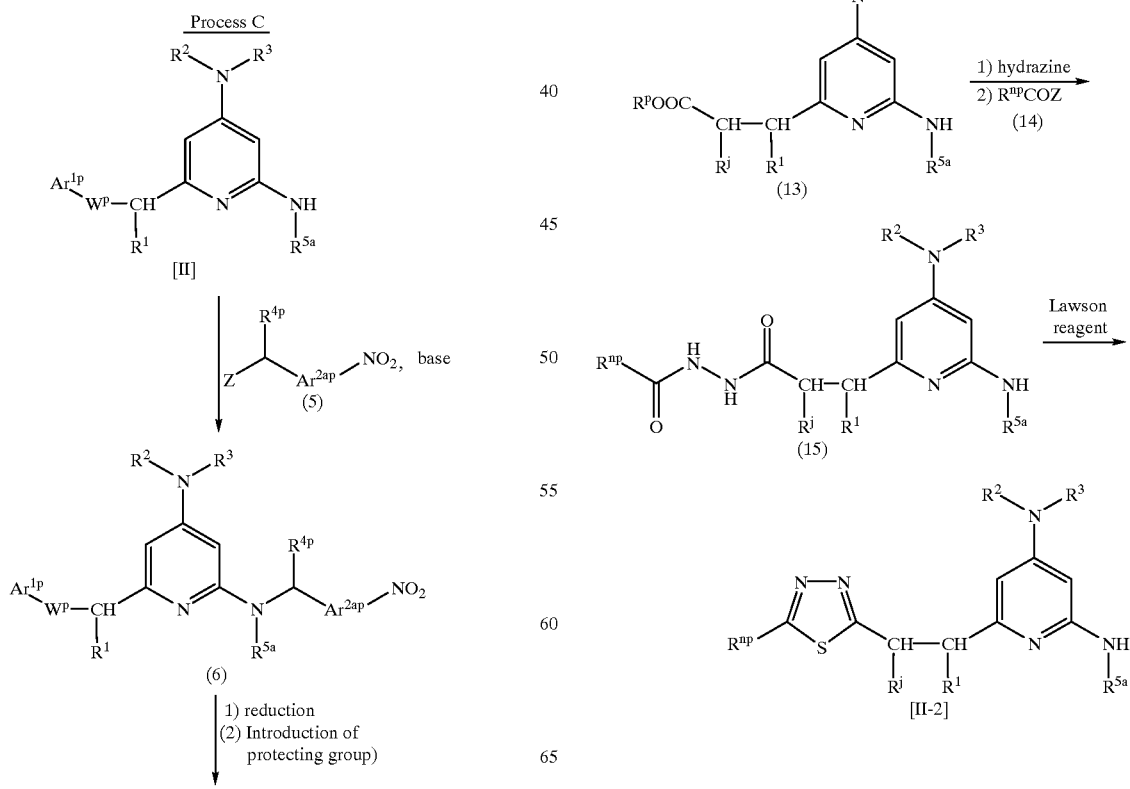

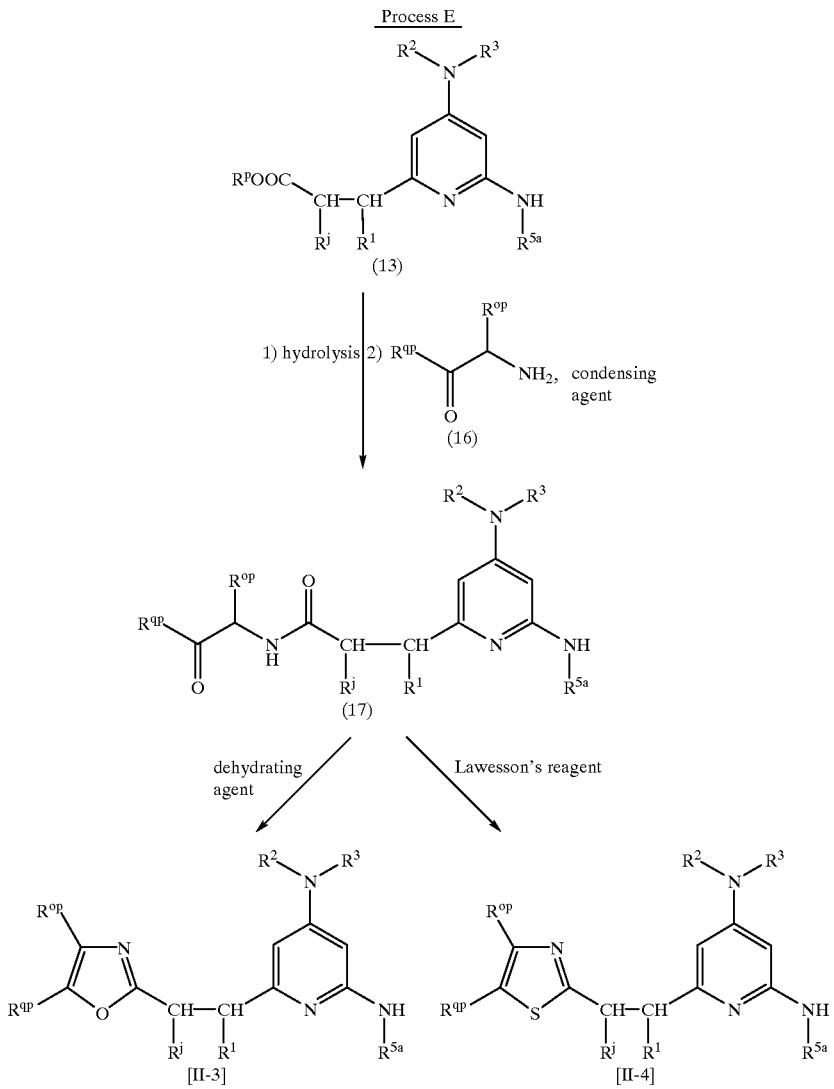

[wherein each of $R^{np}$, $R^{op}$, and $R^{qp}$ which are the same or different, is a lower alkyl group, a lower hydroxyalkyl group which may be protected or a group represented by —$NR^{ap}R^{bp}$, or $R^{op}$ and $R^{qp}$ are bonded to each other to form a lower alkylene group; $R^p$ is a lower alkyl group; Q is a protecting group for a hydroxyl group; $Ar^{1p}$, $Ar^{2p}$, $Ar^{2ap}$, $R^1$, $R^2$, $R^3$, $R^{4p}$, $R^{5a}$, $R^{ap}$, $R^{bp}$, $R^{ca}$, $R^j$, T, $W^{1a}$, $W^p$ and Z are as defined above].

In the formulae (3) and (4), Q is a protecting group for a hydroxyl group, which is usually preferably one which is stable in a basic condition and can be removed under an acidic condition or in the presence of fluorine ions, and it may, for example, be preferably a tetrahydropyranyl group or a 2-(trimethylsilyl)ethoxymethyl group.

Process A is a process for producing a compound (II-1), wherein a compound (1) and a compound (V) are condensed, for example, under the same condition as in Process 2, and the product is treated with a base such as sodium hydroxide in a solvent such as water-containing methanol or water-containing tetrahydrofuran to hydrolyze the ester groups; the formed compound (2) is treated in the same manner as the process for converting the compound (XXVIII) to the compound (XV-1) in Process 11; and if necessary, the formed amino group is treated with acetic anhydride, trifluoroacetic anhydride or the like.

Process B is a process for producing a compound (VI-1), wherein a compound (3) is treated, for example, in the same manner as the process for converting the compound (2) to the compound (II-1) in the above Process A; the obtained compound (4) and a compound (III) are condensed under the same condition as in Process 1; the protecting group Q for a hydroxyl group is removed under a weakly acidic condition or in the presence of fluorine ions; and finally e.g. a chlorine atom, a bromine atom or a methanesulfonyloxy group is introduced as a leaving group.

Process C is a process for producing a compound (XIII-1), wherein a compound (II) and a compound (5) are condensed, for example, under the same condition as in Process 1; a nitro group of the product (6) is reduced; and if necessary, the formed amino group is treated by acetic anhydride, trifluoroacetic anhydride or the like.

The reduction of a nitro group can be carried out, for example, by a method of treating with iron powder and ammonium chloride under heating in a solvent such as a water-containing ethanol or water-containing dioxane, a method of treating with stannous chloride under heating in a solvent such as ethanol, or catalytic reduction employing a palladium-carbon catalyst or the like in an inert solvent such as methanol or ethanol.

Process D is a process for producing a compound (II-2), wherein the protecting group Q for a hydroxyl group of a compound (4) is removed under a weakly acidic condition or in the presence of fluorine ions; the formed alcohol is oxidized with an oxidizing agent such as sulfur trioxide-pyridine complex; the obtained compound (11) and a compound (12) are treated under the same condition as in Process 3; the obtained compound (13) is reacted with hydrazine to obtain a hydrazide; the hydrazide is acylated by a compound (14); and e.g. Lawesson's reagent is reacted to the obtained compound (15).

Process E is a process which comprises treating a compound (13) with a base such as sodium hydroxide in a solvent such as water-containing methanol or water-containing tetrahydrofuran to hydrolyze the ester group; condensing the formed compound and a compound (16) in the presence of a condensing agent such as benzotriazole-1-yloxy-tris-pyrrolidinophosphonium hexafluorophosphate; and reacting a dehydrating agent such as thionyl chloride to the obtained compound (17) to obtain a compound (II-3), or by reacting Lawesson's reagent or the like to the compound (17) to obtain a compound (II-4).

The starting material compounds (1) and (3) used in the above Processes A to E can be produced and obtained, for example, by the following processes.

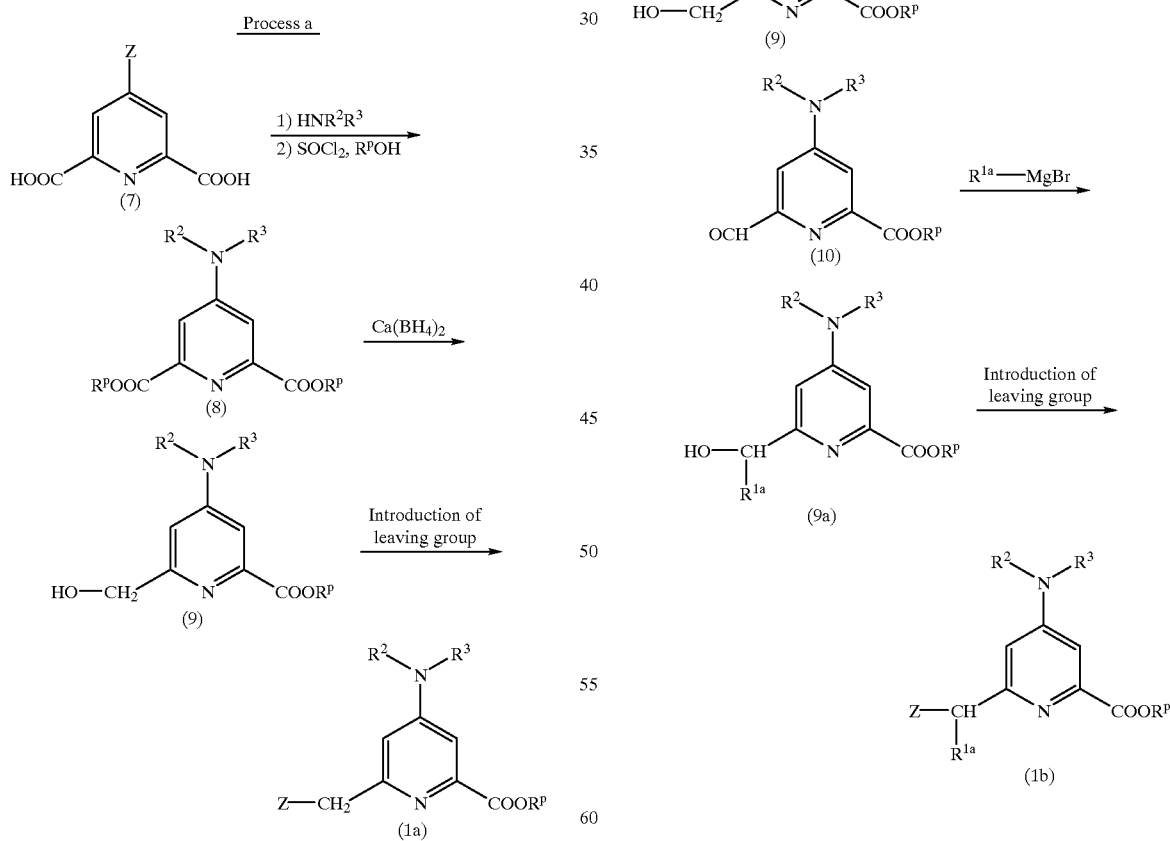

-continued

Process d

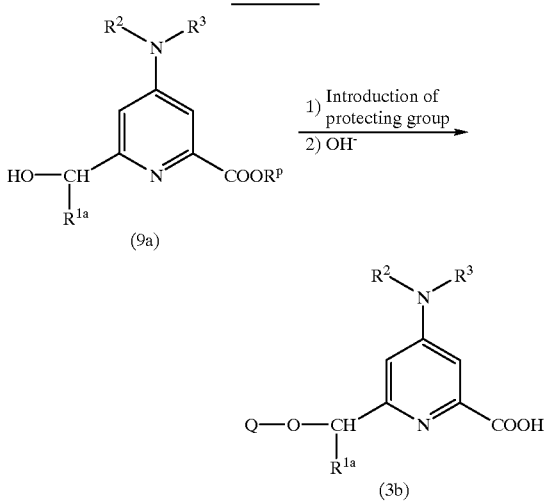

[wherein $R^{1a}$ is a lower alkyl group; and $R^2$, $R^3$, Z, $R^p$ and Q are as defined above].

Usefulness of the compound of the present invention as a pharmaceutical, is specifically demonstrated, for example, by the following Pharmacological Test Example 1 or 2.

Pharmacological Test Example 1

(NPY Binding Inhibition Test)

A membrane sample prepared from SK-N-MC cells derived from human neuroblastoma in which the expression of NPY Y1 receptor was reported, was incubated at 25° C. for 2 hours together with a test compound and 20,000 cpm of [$^{125}$I] peptide YY (manufactured by Amersham Company) in an assay buffer (25 mM HEPES buffer solution containing 10 mM of magnesium chloride, 1 mM of phenylmethylsulfonyl fluoride, 0.1% of bacitracin and 0.5% of BSA, pH 7.4), and then subjected to filtration by a glass filter GF/C. After washing with a 50 mM Tris buffer solution containing 0.3% of BSA at pH 7.4, the radiation activity on the glass filter was measured by a gamma counter. The nonspecific binding was measured in the presence of 1 $\mu$M of peptide YY and the 50% inhibition concentration ($IC_{50}$) of the test compound against specific [$^{125}$I] peptide YY binding was obtained [Endocrinology, vol. 131, 2090 (1992)]. The results are shown in Table.

| Test compound | $IC_{50}$ (nM) |
|---|---|
| Example 4 | 0.33 |

As shown above, the compound of the present invention strongly inhibited the binding of peptide YY (NPY homologue) to the NPY Y1 receptor.

Pharmacological Test Example 2

(Antagonistic Test Against NPY-Induced Feeding Behavior In Vivo)

Under pentobarbital anesthesia (intraperitoneal single administration of 200 mg/kg), a chronic guide cannula (outer diameter: 0.8 mm, inner diameter: 0.5 mm, length: 10 mm) was inserted stereotaxically in the right lateral cerebral ventricle of a male SD rat (7 to 8 weeks old, 200 to 300 g) and fixed by a dental resin. The forward end position of the guide cannula was at 0.9 mm posterior to bregma, 1.2 mm to the right of the midline and 1.5 mm ventral to the brain surface, so that when an inner needle was inserted, the forward end extended beyond the forward end of the guide cannula by about 2 mm and reached the lateral ventricle. After a recovery period of about one week, NPY (5 $\mu$g/head/ 10 $\mu$l) was administered into the lateral ventricle. The test compound was simultaneously administered as mixed with NPY, and food intake for two hours after the administration was measured. With respect to the obtained result, a multiple comparative determination was carried out by Duncan's test, whereby p<0.05 was taken as significant.

As a result of the above described test operation, the compound of Example 4 (200 $\mu$g/head) significantly suppressed the increase in food intake induced by NPY simultaneously administered.

As a result of the foregoing, the compound (I) of the present invention is useful as a treating agent for various diseases associated with NPY, for example, cardiovascular diseases, such as hypertension, renal diseases, cardiac diseases or vasospasm, central diseases, such as hyperphagia, depression, epilepsy or dementia, metabolic diseases, such as obesity, diabetes or hormone unbalance, or glaucoma, particularly as a treating agent for e.g. hyperphagia, obesity or diabetes.

The compound represented by the general formula (I) can be orally or parenterally administered, and it may be formulated into a formulation suitable for such administration, so that it can be used as a treating agent for cardiovascular diseases, such as hypertension, renal diseases, cardiac diseases or vasospasm, central diseases, such as hyperphagia, depression, epilepsy or dementia, metabolic diseases, such as obesity, diabetes or hormone unbalance, or glaucoma. To use the compound of the present invention for clinical purpose, it may be formulated into various formulations by an addition of pharmaceutically acceptable additives in accordance with the type of administration and then administered. As such additives, various additives which are commonly used in the field of drug formulations, may be used, including, for example, gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin, etc.

A drug formulation to be prepared as a mixture with such additives, may, for example, be a solid formulation such as a tablet, a capsule, a granule, a powder or a suppository; or a liquid formulation such as a syrup, an elixir or an injection drug. These formulations can be prepared in accordance with conventional methods commonly employed in the field of drug formulations. Further, in the case of liquid formulation, it may be of the type which is to be dissolved or suspended in water or in other suitable medium at the time of its use. Particularly, in the case of an injection drug, it may be dissolved or suspended in a physiological saline or in a glucose solution, and a buffering agent or a preserving agent may further be added.

These formulations may contain the compound of the present invention in a proportion of from 1.0 to 100 wt %, preferably from 1.0 to 60 wt % of the total amount.

In a case where the compound of the present invention is used, for example, in the clinical field, its dose and the frequency of administration vary depending upon the sex, the age, the body weight and the diseased degree of the patient and the type and the range of the intended treating effects. However, in the case of an oral administration, it is preferred to administer from 0.1 to 100 mg/kg per day for an adult all at once or in a few times in a divided fashion. In the case of parental administration, it is preferred to administer from 0.001 to 10 mg/kg per day for an adult all at once or in a few times in a divided fashion.

BEST MODE FOR CARRYING OUT THE INVENTION

The present invention will be described in further detail with reference to Examples. However, it should be understood that the present invention is by no means restricted by such Examples.

EXAMPLE 1

Preparation of 2-benzylamino-6-(5-ethyl-1,3,4-thiadiazol-2-ylthiomethyl)-4-morpholinopyridine (1) Preparation of dimethyl 4-morpholino-2,6-pyridinedicarboxylate 4-chloro-2,6-pyridinedicarboxylic acid (1.5 g) was suspended in morpholine (13 ml) and refluxed under heating for 8 hours. Morpholine was distilled off under reduced pressure, and the residue was dissolved in 10% hydrochloric acid-methanol (20 ml) and refluxed under heating for 8 hours. The reaction solution was concentrated under reduced pressure, and then the residue was again dissolved in 10% hydrochloric acid-methanol (20 ml) and stirred at 40° C. for 14 hours, followed by refluxing under heating for two hours. To the residue, ethyl acetate and water were added, and the mixture was made alkaline with potassium carbonate. Then, the organic layer was separated and dried over anhydrous sodium sulfate. The solvent was distilled off under reduced pressure to obtain the above identified compound (1.4 g) as a yellowish white solid.

(2) Preparation of ethyl 6-hydroxymethyl-4-morpholino-2-pyridinecarboxylate

The compound (1.3 g) obtained by the above reaction and calcium chloride (283 mg) were suspended in ethanol (38 ml), and sodium borohydride (88 mg) was added under cooling to a temperature of from −10 to −5° C., followed by stirring at the same temperature for one hour. Excess calcium borohydride was decomposed by acetone. Then, water was added thereto, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (chloroform/methanol=50:1→10:1), to obtain the above identified compound (865 mg) as a white solid.

(3) Preparation of ethyl 6-(5-ethyl-1,3,4-thiadiazol-2-ylthiomethyl)-4-morpholino-2-pyridinecarboxylate The compound (860 mg) obtained by the above reaction was dissolved in chloroform (10 ml), and thionyl chloride (1.6 ml) was added under cooling with ice, followed by stirring at the same temperature for 1.5 hours. The solvent and thionyl chloride were distilled off under reduced pressure, and then, the residue was dissolved in dimethylformamide (10 ml). Under cooling with ice, potassium carbonate (4.4 g) and 5-ethyl-2-mercapto-1,3,4-thiadiazole (567 mg) were sequentially added. The reaction solution was stirred at room temperature for 14 hours, then diluted with ethyl acetate and sequentially washed with water and a saturated sodium chloride aqueous solution. The organic layer was dried over anhydrous sodium sulfate, and then, the solvent was distilled off under reduced pressure to obtain the above identified compound (1.2 g) as a yellow oily substance.

(4) Preparation of 6-(5-ethyl-1,3,4-thiadiazol-2-ylthiomethyl)-4-morpholino-2-pyridinecarboxylic acid The compound (1.2 g) obtained by the above reaction was dissolved in ethanol (9 ml), and a 1N sodium hydroxide aqueous solution (4.8 ml) was added thereto, followed by stirring at room temperature for one hour. 1N hydrochloric acid (6 ml) was added to the reaction solution. The precipitate was collected by filtration and washed with cold ethanol to obtain the above identified compound (770 mg) as a white solid.

(5) Preparation of tert-butyl N-[6-(5-ethyl-1,3,4-thiadiazol-2-ylthiomethyl)-4-morpholino-2-pyridyl]carbamate The compound (770 mg) obtained by the above reaction, diphenylphosphoryl azide (0.498 ml) and triethylamine (0.322 ml) were suspended in a solvent mixture comprising tert-butanol (20 ml) and dimethylformamide (4 ml), followed by refluxing under heating for 5 hours. The solvent was distilled off under reduced pressure, and the residue was dissolved in ethyl acetate, and then sequentially washed with a 10% citric acid aqueous solution, a saturated sodium hydrogen carbonate aqueous solution and a saturated sodium chloride aqueous solution. The organic layer was dried over anhydrous sodium sulfate, and then, the solvent was distilled off under reduced pressure. The residue was recrystallized from methanol to obtain the above identified compound (560 mg) as a white solid.

(6) Preparation of 2-(N-benzyl-N-tert-butoxycarbonyl)amino-6-(5-ethyl-1,3,4-thiadiazol-2-ylthiomethyl)-4-morpholinopyridine The compound (80 mg) obtained by the above reaction was added to a suspension of 60% sodium hydride (7.9 mg) in dimethylformamide (1.5 ml), under cooling with ice and stirred at room temperature for 30 minutes. Then, under cooling with ice, benzyl bromide (24 µl) was added, followed by stirring at room temperature for 3 hours. Water was added to the reaction solution, followed by extraction with ethyl acetate. Then, the organic layer was washed sequentially with water and a saturated sodium chloride aqueous solution and dried over anhydrous sodium sulfate. The solvent was distilled off under reduced pressure to obtain the above identified compound (100 mg) as a brown oily substance.

(7) Preparation of 2-benzylamino-6-(5-ethyl-1,3,4-thiadiazol-2-ylthiomethyl)-4-morpholinopyridine To the compound (100 mg) obtained by the above reaction, trifluoroacetic acid (1.5 ml) was added under cooling with ice, and stirred at room temperature for 30 minutes. The solvent was distilled off under reduced pressure, and then, the residue was partitioned between a saturated sodium hydrogen carbonate/ethyl acetate. The organic layer was separated, washed with a saturated sodium chloride aqueous solution and then dried over anhydrous sodium sulfate. The solvent was distilled off under reduced pressure, and the residue was purified by thin layer chromatography for separation (silica gel 60F254, manufactured by Merck Company, hexane:ethyl acetate=1:2) to obtain the above identified compound (53 mg) as a pale yellow oily substance.

$^1$H-NMR(CDCl$_3$) δ:1.37(3H, t, J=7.6 Hz), 3.05(2H, q, J=7.6 Hz), 3.16(4H, dd, J=4.9 Hz, 5.0 Hz), 3.76(4H, dd, J=4.9 Hz, 5.0 Hz), 4.42–4.45(4H, m), 5.00–5.10(1H, m), 5.57(1H, d, J=1.9 Hz), 6.32(1H, d, J=1.9 Hz), 7.28–7.37(5H, m).

EXAMPLE 2

Preparation of 6-(5-ethyl-1,3,4-thiadiazol-2-ylthiomethyl)-2-(3-methoxybenzylamino)-4-morpholinopyridine The above identified compound was obtained as a vermilion oily substance in the same manner as in Example 1-(6) and (7) except that benzyl bromide was changed to 3-methoxybenzyl bromide.

$^1$H-NMR(CDCl$_3$) δ:1.38(3H, t, J=7.6 Hz), 3.06(2H, q, J=7.6 Hz), 3.17(4H, dd, J=4.9 Hz, 5.0 Hz), 3.77(4H, dd, J=4.9 Hz, 5.0 Hz), 3.79 (3H, s), 4.42(2H, d, J=5.6 Hz), 4.43(2H, s), 4.93(1H, brs), 5.58(1H, d, J=2.1 Hz), 6.32(1H, d, J=2.1 Hz), 6.80(1H, dd, J=1.7 Hz, 7.9 Hz), 6.92(1H, t, J=1.7 Hz), 6.93(1H, dd, J=1.7 Hz, 7.9 Hz), 7.24(1H, t, J=7.9 Hz).

EXAMPLE 3

Preparation of 6-(5-ethyl-1,3,4-thiadiazol-2-ylthiomethyl)-2-(3-hydroxybenzylamino)-4-morpholinopyridine To a solution of the compound (18.2 mg) obtained in Example 2 in methylene chloride (0.5 ml), boron tribromide (a 1.0M methylene chloride solution, 0.30 ml) was added at −78° C., and the temperature was raised to about 2° C. over a period of 3.6 hours. Then, a saturated sodium hydrogen carbonate aqueous solution (20 ml) was added thereto. The reaction solution was extracted with ethyl acetate, and the organic layer was washed with a saturated sodium chloride aqueous solution and then dried over anhydrous sodium sulfate. The solvent was distilled off under reduced pressure. The residue was purified by thin layer chromatography for separation (silica gel 60F254, manufactured by Merck Company, chloroform:methanol=10:1) to obtain the above identified compound (14.9 mg) as a colorless oily substance.

$^1$H-NMR(CDCl$_3$) δ:1.36(3H, t, J=7.6 Hz), 3.05(2H,q, J=7.6 Hz), 3.17(4H, dd, J=4.9 Hz, 5.0 Hz), 3.75(4H, dd, J=4.9 Hz, 5.0 Hz), 4.35 (2H, s), 4.30–4.43(2H, m), 5.13–5.28(1H, m), 5.54(1H, d, J=1.9 Hz), 6.33(1H, d, J=1.9 Hz), 6.56(1H, d, J=7.8 Hz), 6.77(1H, d, J=7.8 Hz), 6.96(1H, brs), 7.15(1H, t, J=7.8 Hz).

EXAMPLE 4

Preparation of 6-(5-ethyl-1,3,4-thiadiazol-2-ylthiomethyl)-4-morpholino-2-[3-(2-propenyloxycarbonylamino)benzylamino]pyridine (1) Preparation of 2-[N-tert-butoxycarbonyl-N-(3-methoxycarbonylbenzyl)amino]-6-(5-ethyl-1,3,4-thiadiazol-2-ylthiomethyl)-4-morpholinopyridine The above identified compound was obtained as a pale yellow oily substance in the same manner as in Example 1-(6) except that benzyl bromide was changed to methyl 3-bromomethylbenzoate.

(2) Preparation of 2-[N-tert-butoxycarbonyl-N-(3-carboxybenzyl)amino]-6-(5-ethyl-1,3,4-thiadiazol-2-ylthiomethyl)-4-morpholinopyridine The compound (763 mg) obtained by the above reaction was dissolved in a solvent mixture comprising methanol (2.0 ml) and tetrahydrofuran (2.0 ml), and 1N sodium hydroxide aqueous solution (2.1 ml) was added thereto, followed by stirring at 50° C. for two hours. Water was added, and the aqueous layer was washed with ethyl ether. The aqueous layer was neutralized with a 10% citric acid aqueous solution and extracted twice with ethyl acetate. The organic layer was dried over anhydrous sodium sulfate, and the solvent was distilled off under reduced pressure to obtain the above identified compound (657 mg) as a yellow solid.

(3) Preparation of 2-{N-tert-butoxycarbonyl-N-[3-(2-propenyloxycarbonylamino)benzyl]amino}-6-(5-ethyl-1,3,4-thiadiazol-2-ylthiomethyl)-4-morpholinopyridine The compound (657 mg) obtained by the above reaction, diphenylphosphoryl azide (0.30 ml) and triethylamine (0.20 ml) was suspended in allyl alcohol (8 ml) and dimethylformamide (4 ml) and refluxed under heating for 3 hours. Chloroform was added thereto, followed by washing with water and a saturated sodium chloride aqueous solution. The aqueous layer was extracted with ethyl acetate, and the ethyl acetate layer was washed three times with water and further washed with a saturated sodium chloride aqueous solution. The organic layers were put together and dried over anhydrous sodium sulfate, and then, the solvent was distilled off under reduced pressure. The residue was purified by silica gel column chromatography (hexane/ethyl acetate=1:1) to obtain the above identified compound (543 mg) as a pale yellow solid.

(4) Preparation of 6-(5-ethyl-1,3,4-thiadiazol-2-ylthiomethyl)-4-morpholino-2-[3-(2-propenyloxycarbonylamino)benzylamino]pyridine Using the compound obtained by the above reaction, the above identified compound was obtained as a yellow oily substance in the same manner as in Example 1-(7).

$^1$H-NMR(CDCl$_3$) δ:1.37(3H, t, J=7.6 Hz), 3.06(2H, q, J=7.6 Hz), 3.17(4H, dd, J=4.9 Hz, 5.1 Hz), 3.76(4H, dd, J=4.9 Hz, 5.1 Hz), 4.42 (2H, s), 4.43(2H, d, J=6.3 Hz), 4.66(2H, dt, J=5.7 Hz, 1.4 Hz), 4.95–5.09(1H, m), 5.26(1H, dq, J=10.4 Hz, 1.4 Hz), 5.36(1H, dq, J=17.2 Hz, 1.4 Hz), 5.56(1H, d, J=2.0 Hz), 5.96(1H, ddt, J=10.4 Hz, 17.2 Hz, 5.7 Hz), 6.32(1H, d, J=2.0 Hz), 6.79(1H, brs), 7.05(1H, d, J=7.6 Hz), 7.26(1H, t, J=7.6 Hz), 7.32(1H, d, J=7.6 Hz), 7.39(1H, s).

EXAMPLE 5

Preparation of 6-(5-ethyl-1,3,4-thiadiazol-2-ylthiomethyl)-2-[3-(methylsulfonylamino)benzylamino]-4-morpholinopyridine (1) Preparation of 2-[N-(3-aminobenzyl)-N-(tert-butoxycarbonyl)amino]-6-(5-ethyl-1,3,4-thiadiazol-2-ylthiomethyl)-4-morpholinopyridine To a solution of the compound (100 mg) obtained in Example 4-(3) in chloroform (1.5 ml), water (57 μl), tributyltin hydride (86 μl) and palladium dichloride-bistriphenylphosphine complex (6 mg) were added at room temperature, followed by stirring for 3 hours. To the reaction solution, a saturated sodium chloride aqueous solution was added, followed by extraction with ethyl acetate. The organic layer was dried over anhydrous sodium sulfate, and then, the solvent was distilled off under reduced pressure. The residue was purified by thin layer chromatography for separation (silica gel 60F254, manufactured by Merck Company, chloroform:methanol=10:1) to obtain the above identified compound (45 mg) as a pale yellow oily substance.

(2) Preparation of 2-[3-[bis(methylsulfonyl)amino]benzylamino]-6-(5-ethyl-1,3,4-thiadiazol-2-ylthiomethyl)-4-morpholinopyridine To a solution of the compound (15 mg) obtained by the above reaction in chloroform (1 ml), triethylamine (12 μl) and methanesulfonyl chloride (6 μl) were added under cooling with ice, followed by stirring at room temperature for 4 hours. The reaction solution was partitioned between water and chloroform. Then, the organic layer was separated, washed with a saturated sodium chloride aqueous solution and then, dried over anhydrous sodium sulfate. The solvent was distilled off under reduced pressure, and the residue was purified by thin layer chromatography for separation (silica gel 60F254, manufactured by Merck Company, chloroform:methanol=15:1) to obtain a pale yellow oily substance (13 mg). Then, the pale yellow oily substance was treated in the same manner as in Example 1-(7) to obtain the above identified compound (10.5 mg) as a pale yellow oily substance.

(3) Preparation of 6-(5-ethyl-1,3,4-thiadiazol-2-ylthiomethyl)-2-[3-(methylsulfonylamino)benzylamino]-4-morpholinopyridine To a methanol (0.3 ml)-tetrahydrofuran (0.2 ml) solution of the compound (9 mg) obtained by the above reaction, a 1N sodium hydroxide aqueous solution (22 μl) was added under cooling with ice and stirred at room temperature for 4 hours. The reaction solution was diluted with chloroform and washed with a saturated sodium chloride aqueous solution and then, dried over anhydrous sodium sulfate. The solvent was distilled off under reduced pressure, and the residue was purified by thin layer chromatography for separation (silica gel 60F254, manufactured by Merck Company, chloroform:methanol=15:1) to obtain the above identified compound (5.2 mg) as a pale yellow oily substance.

$^1$H-NMR(CDCl$_3$) δ:1.37(3H, t, J=7.6 Hz), 2.97(3H, s), 3.08(2H, q, J=7.6 Hz), 3.16(4H, dd, J=4.9 Hz, 5.0 Hz), 3.76(4H, dd, J=4.9 Hz, 5.0 Hz), 4.39(2H, s), 4.48(2H, d, J=5.7 Hz), 5.00–5.12(1H, m), 5.55 (1H, d, J=1.7 Hz), 6.32(1H, d, J=1.7 Hz), 7.14(1H, d, J=7.3 Hz), 7.19–7.30(3H, m).

EXAMPLE 6

Preparation of 6-(5-ethyl-1,3,4-thiadiazol-2-ylthiomethyl)-2-(3-methylbenzylamino)-4-thiomorpholinopyridine (1) Preparation of tert-butyl N-[6-(5-ethyl-1,3,4-thiadiazol-2-ylthiomethyl)-4-thiomorpholino-2-pyridyl]carbamate The above identified compound was obtained in the same manner as in Example 1-(1) to (5) except that morpholine was changed to thiomorpholine.

(2) Preparation of 6-(5-ethyl-1,3,4-thiadiazol-2-ylthiomethyl)-2-(3-methylbenzylamino)-4-thiomorpholinopyridine Using the compound obtained by the above reaction, the above identified compound was obtained as a orange colored oily substance in the same manner as in Example 1-(6) and (7) except that benzyl bromide was changed to 3-methylbenzyl bromide.

$^1$H-NMR(CDCl$_3$) δ:1.38(3H, t, J=7.6 Hz), 2.34(3H, s), 2.56(4H, dd, J=5.0 Hz, 5.2 Hz), 3.06(2H, q, J=7.6 Hz), 3.66(4H, dd,J=5.0 Hz, 5.2 Hz), 4.38(2H, d, J=5.7 Hz), 4.41(2H, s), 4.92–5.04(1H, m), 5.51 (1H, d, J=2.1 Hz), 6.27(1H, d, J=2.1 Hz), 7.07(1H, d, J=7.6 Hz), 7.15(1H, d, J=7.6 Hz), 7.18(1H, s), 7.22(1H, t, J=7.6 Hz).

EXAMPLE 7

Preparation of 6-(5-ethyl-1,3,4-thiadiazol-2-ylthiomethyl)-4-morpholino-2-[3-(2-propenylaminocarbonylamino)benzylamino]pyridine To a solution of the compound (16 mg) obtained in Example 5-(l) in chloroform (0.5 ml), allyl isocyanate (26 μl) was added under cooling with ice, followed by stirring at room temperature for 30 minutes. To the reaction solution, methanol (2 ml) was added, followed by stirring at room temperature for one hour. Then, the volatile component was distilled off under reduced pressure. The residue was purified by thin layer chromatography for separation (silica gel 60F254, manufactured by Merck Company, chloroform:methanol=95:5) to obtain a colorless oily substance (16 mg). Then, the colorless oily substance was treated in the same manner as in Example 1-(7) to obtain the above identified compound (12.9 mg) as a yellow oily substance.

$^1$H-NMR(CDCl$_3$) δ:1.37(3H, t, J=7.6 Hz), 3.04(2H, q, J=7.6 Hz), 3.14(4H, dd, J=4.8 Hz, 5.0 Hz), 3.74(4H, dd, J=4.8 Hz, 5.7 Hz), 3.85 (2H, tt, J=1.5 Hz, 5.7 Hz), 4.34(2H, s), 4.35(2H, d, J=6.3 Hz), 5.07 (1H, dq, J=10.2 Hz, 1.5 Hz), 5.19(1H, dq, J=17.2 Hz, 1.5 Hz), 5.15–5.24(1H, m), 5.53 (1H, d, J=2.0 Hz), 5.79(1H, t, J=5.7 Hz), 5.85(1H, ddt, J=10.2 Hz, 17.2 Hz, 5.7 Hz), 6.23(1H, d, J=2.0 Hz), 6.89 (1H, d, J=7.8 Hz), 7.17(1H, t, J=7.8 Hz), 7.17(1H, s), 7.54(1H, d, J=7.8 Hz), 7.62(1H, s).

EXAMPLE 8

Preparation of 6-(5-ethyl-1,2,4-triazol-3-ylthiomethyl)-4-morpholino-2-[3-(2-propenyloxycarbonylamino)benzylamino]pyridine (1) Preparation of 4-morpholino-6-trimethylsilylethyloxymethyloxymethyl-2-pyridinecarboxylic acid The compound (1.81 g) obtained in Example 1-(2) was dissolved in methylene chloride (6.8 ml), and trimethylsilylethyloxymethyl chloride (2.27 g) and diisopropylethylamine (3.52 g) were added, followed by stirring at room temperature overnight. The reaction solution was washed sequentially with water, a saturated sodium hydrogen carbonate aqueous solution and a saturated sodium chloride aqueous solution. The organic layer was dried over anhydrous sodium sulfate, and then, the solvent was distilled off under reduced pressure. The residue was dissolved in dioxane (20 ml) and methanol (20 ml), and a 4N sodium hydroxide aqueous solution was added thereto, followed by stirring at room temperature for 12 hours. After neutralization with citric acid, the reaction solution was distilled off under reduced pressure, and ethyl acetate was added to the residue, followed by washing with water and a saturated sodium chloride aqueous solution. The organic layer was dried over anhydrous sodium sulfate, and then, the solvent was distilled off under reduced pressure to obtain the above identified compound (2.15 g) as a white solid.

(2) Preparation of tert-butyl N-(4-morpholino-6-trimethylsilylethyloxymethyloxymethyl-2-pyridyl) carbamate Using the compound obtained by the above reaction, the above identified compound was obtained as a white solid in the same manner as in Example 1-(5).

(3) Preparation of 2-(N-tert-butoxycarbonyl-3-nitrobenzylamino)-4-morpholino-6-trimethylsilylethyloxymethyloxymethylpyridine Using the compound obtained by the above reaction, the above identified compound was obtained as a pale yellow oily substance in the same manner as in Example 1-(6) except that benzyl bromide was changed to 3-nitrobenzyl chloride.

(4) Preparation of 2-{N-(3-aminobenzyl)-N-tert-butoxycarbonylamino)-4-morpholino-6-trimethylsilylethyloxymethyloxymethylpyridine The compound (1.1 g) obtained by the above reaction was dissolved in methanol (120 ml), and palladium-carbon (110 mg) was added thereto, followed by vigorous stirring at room temperature for 2.5 hours in a hydrogen (normal pressure) atmosphere. Palladium-carbon was filtered off, and the filtrate was distilled off under reduced pressure to obtain the above identified compound (0.97 g) as a white solid.

(5) Preparation of 2-[N-tert-butoxycarbonyl-3-(2-propenyloxycarbonylamino)benzylamino]-4-morpholino-6-trimethylsilylethyloxymethyloxymethylpyridine To a solution of the compound (0.97 g) obtained by the above reaction in chloroform (10 ml), 4-dimethylaminopyridine (260 mg) and allyl chloroformate (0.23 ml) were added at 0° C. and stirred at room temperature for one hour. Then, the solvent was distilled off under reduced pressure. The residue was purified by silica gel column chromatography (ethyl acetate/heptane=0/1→1/1) to obtain the above identified compound (1.13 g) as a colorless oily substance.

(6) Preparation of 2-[N-tert-butoxycarbonyl-3-(2-propenyloxycarbonylamino)benzylamino]-6-hydroxymethyl-4-morpholinopyridine The compound (1.03 g) obtained by the above reaction was dissolved in a 1N hydrochloric acid-methanol (15 ml), followed by stirring at room temperature for 2.5 hours. Then, the solvent was distilled off under reduced pressure. A saturated sodium hydrogen carbonate aqueous solution was added to the residue, followed by extraction with ethyl acetate. The organic layer was washed with a saturated sodium chloride aqueous solution and dried over anhydrous magnesium sulfate. Then, the solvent was distilled off under reduced pressure. The residue was purified by silica gel column chromatography (methanol/chloroform=0/1→2/50) to obtain the above identified compound (608 mg).

(7) Preparation of 2-[N-tert-butoxycarbonyl-3-(2-propenyloxycarbonylamino)benzylamino]-6-(5-ethyl-1,2,4-triazol-3-ylthiomethyl)-4-morpholinopyridine To a solution of the compound (75 mg) obtained by the above reaction in a tetrahydrofuran, methanesulfonyl chloride (0.019 ml) and triethylamine (0.035 ml) were added at 0° C., followed by stirring at room temperature for two hours. Then, ethyl acetate was added thereto, followed by sequential washing with water, a saturated sodium hydrogen carbonate aqueous solution and a saturated sodium chloride aqueous solution. The organic layer was dried over anhydrous magnesium sulfate, and then, the solvent was distilled off under reduced pressure. The residue was dissolved in dimethylformamide (2 ml), and potassium carbonate (207 mg) and 5-ethyl-3-mercapto-1,2,4-triazole (38.8 mg) were added thereto, followed by stirring at room temperature overnight. To the reaction solution, ethyl acetate was added, followed by sequential washing with water and a saturated sodium chloride aqueous solution. The organic layer was dried over anhydrous magnesium sulfate, and then, the solvent was distilled off under reduced pressure to obtain the above identified compound (96 mg).

(8) Preparation of 6-(5-ethyl-1,2,4-triazol-3-ylthiomethyl)-4-morpholino-2-[3-(2-propenyloxycarbonylamino)benzylamino]pyridine Using the compound obtained by the above reaction, the above identified compound was obtained as a pale yellow solid in the same manner as in Example 1-(7).

$^1$H-NMR(CDCl$_3$) δ: 1.30(3H, t, J=7.6 Hz), 2.74(2H, q, J=7.6 Hz), 3.15–3.25(4H, m), 3.70–3.85(4H, m), 3.99(2H, s), 4.43(2H, d, J=3.8 Hz), 4.66(2H, d, J=5.7 Hz), 5.20–5.40 (3H, m), 5.55–5.60(1H, m), 5.85–6.05(1H, m), 6.10–6.20 (1H, m), 7.04(1H, d, J=7.4 Hz), 7.11(1H, s), 7.20–7.30(1H, m), 7.30–7.45(2H, m).

Examples 9 to 21 were obtained in the same manner as in Example 8-(7) and (8) except that 5-ethyl-3-mercapto-1,2,4-triazole was changed to the corresponding mercaptan.

EXAMPLE 9

6-(1-methylimidazol-2-ylthiomethyl)-4-morpholino-2-[3-(2-propenyloxycarbonylamino)benzylamino]pyridine $^1$H-NMR(CDCl$_3$) δ: 3.07(4H, t, J=4.9 Hz), 3.41(3H, s), 3.73(4H, t, J=4.9 Hz), 4.03(2H, s), 4.41(2H, d, J=5.9 Hz), 4.65(2H, d, J=5.6 Hz), 4.85(1H, br), 5.26(1H, d, J=10.0 Hz), 5.35(1H, d, J=17.1 Hz), 5.53(2H, d, J=2.0 Hz), 5.88(2H, d, J=2.0 Hz), 5.90–6.00 (1H, m), 6.80(1H, br), 7.00–7.10(2H, m), 7.20–7.30(2H, m), 7.43 (1H, brs).

EXAMPLE 10

6-(5-methylamino-1,3,4-thiadiazol-2-ylthiomethyl)-4-morpholino-2-[3-(2-propenyloxycarbonylamino) benzylamino]pyridine $^1$H-NMR(CDCl$_3$) δ: 3.00(3H, s), 3.20(4H, t, J=5.0 Hz), 3.75(4H, t, J=4.7 Hz), 4.19(2H, s), 4.43(2H, d, J=3.8 Hz), 4.65(2H, d, J=5.6 Hz), 5.00(1H, s), 5.25(1H, d, J=10.3 Hz), 5.35(1H, d, J=17.3 Hz), 5.93(1H, ddd, J=5.6 Hz, 10.3 Hz, 17.3 Hz), 6.26(1H, s), 7.01 (1H, d, J=7.3 Hz), 7.30(1H, s), 7.26(1H, t, J=7.3 Hz), 7.41(1H, d, J=7.3 Hz).

EXAMPLE 11

6-(5-isopropyl-1,3,4-thiadiazol-2-ylthiomethyl)-4-morpholino-2-[3-(2-propenyloxycarbonylamino) benzylamino]pyridine $^1$H-NMR(CDCl$_3$) δ: 1.39(6H, d, J=6.9 Hz), 3.16(4H, t, J=5.0 Hz), 3.40(1H, sept, J=6.9), 3.76(4H, t, J=4.9 Hz), 4.42(4H, s), 4.65(2H, dt, J=1.4 Hz, 5.6 Hz), 5.26(1H, dq, J=1.4 Hz, 10.4 Hz), 5.39(1H, dq, J=1.4 Hz, 17.3 Hz), 5.55(1H, d, J=2.1 Hz), 6.31(1H, d, J=1.9 Hz), 5.95(1H, ddt, J=10.4 Hz, 17.3 Hz), 6.77(1H, brs), 7.04(1H, d, J=7.3 Hz), 7.30(1H, d, J=7.3 Hz), 7.38(1H, s), 7.26(1H, t, J=7.3 Hz).

EXAMPLE 12

6-(5-ethyl-1,3,4-oxadiazol-2-ylthiomethyl)-4-morpholino-2-[3-(2-propenyloxycarbonylamino) benzylamino]pyridine $^1$H-NMR(CDCl$_3$) δ: 1.34(3H, t, J=7.6 Hz), 2.83(2H, q, J=7.6 Hz), 3.18(4H, t, J=4.9 Hz), 3.76(4H, t, J=4.9 Hz), 4.34(2H, s), 4.42(2H, d, J=5.7 Hz), 4.63–4.67(2H, m), 5.26(1H, ddd, J=1.3 Hz, 1.3 Hz, 10.4 Hz), 5.30(1H, brs), 5.36(1H, ddd, J=1.5 Hz, 1.5 Hz, 17.2 Hz), 5.56 (1H, d, J=2.0 Hz), 5.89–6.00(1H, m), 6.33(1H, J=2.0 Hz), 6.85(1H, brs) 7.05(1H, d, J=7.3 Hz), 7.24(2H, m), 7.39(1H, brs).

EXAMPLE 13

6-(5-ethyl-1,3-thiazol-2-ylthiomethyl)-4-morpholino-2-[3-(2-propenyloxycarbonylamino)benzylamino]pyridine $^1$H-NMR(CDCl$_3$) δ: 1.27(3H, t, J=7.5 Hz), 2.78(2H, q, J=7.5 Hz), 3.14(4H, t, J=4.9 Hz), 3.75(4H, t, J=4.9 Hz), 4.27(2H, s), 4.40(2H, d, J=), 4.66(2H, d, J=5.7 Hz), 5.20–5.40(1H, m), 5.27(1H, dd, J=1.4 Hz, 15.1 Hz), 5.33 (1H, dd, J=1.4 Hz, 15.9 Hz), 5.50(1H, d, J=2.0 Hz), 5.95(1H, ddt, J=5.7 Hz, 15.1 Hz, 15.9 Hz), 6.22(1H, d, J=2.0 Hz), 6.80(1H, brs), 7.05(1H, d, J=7.5 Hz), 7.25(1H, dd, J=7.5 Hz, 8.1 Hz), 7.33(1H, d, J=8.1 Hz), 7.34(1H, s), 7.38(1H, s).

EXAMPLE 14

6-(4-methyl-1,2,4-triazol-3-ylthiomethyl)-4-morpholino-2-[3-(2-propenyloxycarbonylamino) benzylamino]pyridine $^1$H-NMR(CDCl$_3$) δ: 3.11(4H, dd, J=4.7 Hz, 5.0 Hz), 3.46(3H, s), 3.74(4H, dd, J=4.7 Hz, 5.0 Hz), 4.23(2H, s), 4.40(2H, d, J=5.8 Hz), 4.65(2H, d, J=5.6 Hz), 4.96–5.08(1H, m), 5.25(1H, d, J=10.3 Hz), 5.34(1H, d, J=17.4 Hz), 5.54 (1H, d, J=1.9 Hz), 5.95(1H, ddt, J=5.6 Hz, 10.3 Hz, 17.4 Hz), 6.13(1H, d, J=1.9 Hz), 6.95–7.05(1H, brs), 7.03(1H, d, J=7.2 Hz), 7.23–7.33(2H, m), 7.40(1H, s), 8.08(1H, s).

EXAMPLE 15

4-morpholino-2-[3-(2-propenyloxycarbonylamino) benzylamino]-6-(5-propyl-1,2,4-triazol-3-ylthiomethyl)pyridine $^1$H-NMR(CDCl$_3$) δ: 0.96(3H, t, J=7.4 Hz), 1.76(2H, tq, J=7.4 Hz, 7.6 Hz), 2.68(2H, t, J=7.6 Hz), 3.20(4H, dd, J=4.9 Hz, 5.0 Hz), 3.76 (4H, dd, J=4.9 Hz, 5.0 Hz), 3.99(2H, s), 4.43(2H, d, J=5.3 Hz), 4.65 (2H, d, J=5.7 Hz), 5.25(1H, dd, J=1.0 Hz, 10.4 Hz), 5.35(1H, dd, J=1.0 Hz, 17.1 Hz), 5.57(1H, d, J=1.9 Hz), 5.55–5.75(1H, m), 5.95(1H, ddt, J=5.7 Hz, 10.4 Hz, 17.1 Hz), 6.14(1H, dd, J=1.9 Hz), 7.05(1H, d, J=7.3 Hz), 7.08(1H, brs), 7.26(1H, dd, J=7.3 Hz, 8.1 Hz), 7.35(1H, d, j=8.1 Hz), 7.40(1H, s).

EXAMPLE 16

6-(5-ethyl-4-methyl-1,2,4-triazol-3-ylthiomethyl)-4-morpholino-2-[3-(2-propenyloxycarbonylamino) benzylamino]pyridine $^1$H-NMR(CDCl$_3$) δ: 1.31(3H, t, J=7.6 Hz), 2.69(2H, q, J=7.6 Hz), 3.05–3.15(4H, m), 3.34(3H, m), 3.65–3.75(4H, m), 4.11(2H, s), 4.39(2H, d, J=5.6 Hz), 4.64(2H, d, J=5.6 Hz), 5.20–5.25(1H, m), 5.30–5.40(1H, m), 5.40–5.55(2H, m), 5.85–6.05(1H, m), 6.05–6.10(1H, m), 7.00(1H, d, J=7.5 Hz), 7.20–7.30(1H, m), 7.30–7.40 (2H, m), 7.40–7.60(1H, m).

EXAMPLE 17

6-(5-dimethylamino-1,3,4-thiadiazol-2-ylthiomethyl)-4-morpholino-2-[3-(2-propenyloxycarbonylamino)benzylamino]pyridine $^1$H-NMR(CDCl$_3$) δ: 3.09(6H, s), 3.14(4H, dd, J=4.6 Hz, 4.9 Hz), 3.75(4H, dd, J=4.6 Hz, 4.9 Hz), 4.18(2H, s), 4.41(2H, d, J=5.3 Hz), 4.64(2H, d, J=5.7 Hz), 5.15–5.30(1H, brs), 5.24(1H, dd, J=11.2 Hz, 10.3 Hz), 5.35(1H, dd, J=1.2 Hz, 17.1 Hz), 5.52(1H, d, J=1.8 Hz), 5.95 (1H, ddt, J=5.7 Hz, 10.3 Hz, 17.1 Hz), 6.22(1H, d, J=1.8 Hz), 7.03(1H, d, J=7.6 Hz), 7.00–7.12(1H, brs), 7.25(1H, dd, J=7.6 Hz, 7.9 Hz), 7.33(1H, s), 7.36(1H, d, J=7.9 Hz).

EXAMPLE 18

6-(4-methyl-5-propyl-1,2,4-triazol-3-ylthiomethyl)-4-morpholino-2-[3-(2-propenyloxycarbonylamino) benzylamino]pyridine $^1$H-NMR(CDCl$_3$) δ: 0.99(3H, t, J=7.4 Hz), 1.65–1.80(2H, m), 2.60–2.80(2H, m), 3.05–3.15(4H, m), 3.35(3H, s), 3.70–3.80(4H, m), 4.12(2H, s), 4.40(2H, d, J=5.6 Hz), 4.60–4.70(2H, m), 5.20–5.50(3H, m), 5.50(1H, d, J=2.0 Hz), 5.85–6.00(1H, m), 6.08(1H, d, J=1.9 Hz), 7.02(1H, d, J=7.4 Hz), 7.20–7.30(1H, m), 7.30–7.50 (2H, m).

EXAMPLE 19

6-(4,5-diethyl-1,2,4-triazol-3-ylthiomethyl)-4-morpholino-2-[3-(2-propenyloxycarbonylamino) benzylamino]pyridine $^1$H-NMR(acetone-d$_6$) δ: 1.17(3H, t, J=7.3 Hz), 1.28(3H, t, J=7.5 Hz), 2.70(2H, q, J=7.5 Hz), 3.05–3.15(4H, m), 3.60–3.70(4H, m), 3.83(2H, q, J=7.3 Hz), 4.13(2H, s), 4.49(2H, d, J=6.1 Hz), 4.55–4.65(2H, m), 5.15–5.25(1H, m), 5.30–5.40(1H, m), 5.80–6.15(4H, m), 7.05(1H, d, J=8.1 Hz), 7.22(1H, ddJ=8.1 Hz, 8.1 Hz), 7.47(1H, d, J=8.1 Hz), 7.58(1H, s), 8.89(1H, s).

EXAMPLE 20

6-(5-ethylamino-1,3,4-thiadiazol-2-ylthiomethyl)-4-morpholino-2-[3-(2-propenyloxycarbonylamino) benzylamino]pyridine $^1$H-NMR(CDCl$_3$) δ: 1.26(3H, t, J=7.2 Hz), 3.16(4H, dd, J=4.6 Hz, 5.0 Hz), 3.31(2H, brq, J=7.2 Hz), 3.74(4H, dd, J=4.6 Hz, 5.0 Hz), 4.18 (2H, s), 4.42(2H, d, J=5.7 Hz), 4.65(2H, d, J=5.6 Hz), 5.24(1H, d, J=10.4 Hz), 5.35(1H, d, J=17.0 Hz), 5.52(1H, m), 5.55–5.75(1H, brs), 5.95(1H, ddt, J=5.6 Hz, 10.4 Hz, 17.0 Hz), 6.23(1H, m), 7.01(1H, d, J=7.3 Hz), 7.25(1H, dd, J=7.3 Hz, 8.2 Hz), 7.34(1H, s), 7.40(1H, d, J=8.2 Hz), 7.34–7.56(1H, m).

EXAMPLE 21

6-(5-butyl-4-methyl-1,2,4-triazol-3-ylthiomethyl)-4-morpholino-2-[3-(2-propenyloxycarbonylamino) benzylamino]pyridine $^1$H-NMR(acetone-d$_6$) δ: 0.91(3H, t, J=7.3 Hz), 1.30–1.50 (2H, m), 1.60–1.75(2H, m), 2.60–2.70(2H, m), 3.05–3.15 (4H, m), 3.36 (3H, s), 3.65–3.75(4H, m), 4.04(2H, m), 4.48(2H, d, J=6.1 Hz), 4.55–4.65(2H, m), 5.15–5.40(2H, m), 5.82(1H, d, J=2.0 Hz), 5.59–6.10(2H, m), 6.09(1H, d, J=2.0 Hz), 7.04(1H, d, J=7.6 Hz), 7.22(1H, dd, J=7.6 Hz, 8.0 Hz), 7.48(1H, d, J=8.0 Hz), 7.57(1H, s), 8.93(1H, s).

EXAMPLE 22

Preparation of 6-[2-(5-ethyl-1,3,4-thiadiazol-2 -yl) ethyl]-4-morpholino-2-[3-(2-propenyloxycarbonylamino)benzylamino]pyridine (1) Preparation of tert-butyl N-(6-hydroxymethyl-4-morpholino-2-pyridyl)carbamate Using the compound obtained in Example 8-(2), the above identified compound was obtained as a colorless oily substance in the same manner as in Example 8-(6).

(2) Preparation of tert-butyl N-(6-formyl-4-morpholino-2-pyridyl)carbamate

The compound (1.12 g) obtained by the above reaction was dissolved in dimethyl sulfoxide (45 ml), and a sulfur trioxide-pyridine complex salt (2.88 g) was added thereto, followed by stirring at room temperature for 2.5 hours. The reaction solution was added to water and extracted three times with ethyl acetate. The organic layer was washed three times with water. The organic layer was dried over anhydrous magnesium sulfate and then, the solvent was distilled off under reduced pressure to obtain the above identified compound (1.2 g) as a white solid.

(3) Preparation of tert-butyl N-(6-methoxycarbonylethyl-4-morpholino-2-pyridyl)carbamate To a solution of methyl dimethylphosphonoacetate (0.7 ml) in tetrahydrofuran (30 ml), 60% sodium hydride (202 mg) was added at −20° C., followed by stirring at the same temperature for 20 minutes. Then, a solution of the compound (1.11 g) obtained by the above reaction in tetrahydrofuran (15 ml), was added at the same temperature, followed further by stirring at the same temperature for one hour. The solvent was distilled off under reduced pressure, and water was added to the residue. The mixture was extracted three times with ethyl acetate. The organic layer was washed with water and dried over anhydrous magnesium sulfate. Then, the solvent was distilled off under reduced pressure. The residue was dissolved in a solvent mixture comprising ethyl acetate (10 ml), tetrahydrofuran (25 ml) and ethanol (25 ml), and palladium-carbon (260 mg) was added thereto, followed by vigorous stirring at room temperature for 18 hours in a hydrogen (normal pressure) atmosphere. Palladium-carbon was filtered off, and the filtrate was concentrated under reduced pressure to obtain the above identified compound (1.33 g) as a white solid.

(4) Preparation of tert-butyl N-(6-hydrazinocarbonylethyl-4-morpholino-2-pyridyl)carbamate To a solution of the compound (350 mg) obtained by the above reaction in methanol (10 ml) and tetrahydrofuran (2 ml), hydrazine monohydrate (1.16 ml) was added, followed by stirring at room temperature for 4.5 days. The reaction solution was concentrated under reduced pressure to obtain the above identified compound (350 mg) as a colorless oily substance.

(5) Preparation of tert-butyl N-[4-morpholino-6-(2-propionohydrazino)carbonylethyl-2-pyridyl]carbamate To a solution of the compound (350 mg) obtained by the above reaction in chloroform (2 ml), pyridine (0.5 ml) and propionic anhydride (70 μl) were added at 0° C., followed by stirring at room temperature for 1.5 hours. To the reaction solution, a saturated sodium hydrogen carbonate aqueous solution was added, and the mixture was extracted three times with chloroform. The organic layer was washed with water and dried over anhydrous magnesium sulfate. Then, the solvent was distilled off under reduced pressure. The residue was purified by silica gel column chromatography (methanol/chloroform=1/100→4/100) to obtain the above identified compound (94 mg) as a colorless oily substance.

(6) Preparation of tert-butyl N-{6-[2-(5-ethyl-1,3,4-thiadiazol-2-yl)ethyl]-4-morpholino-2-pyridyl}carbamate To a solution of the compound (94 mg) obtained by the above reaction in tetrahydrofuran (2 ml), Lawesson's reagent (135 mg) was added, followed by stirring at room temperature for 7.5 hours. The solvent was distilled off under reduced pressure, and the residue was purified by silica gel column chromatography (methanol/chloroform=2/100→4/100) to obtain the above identified compound (68 mg) as a colorless oily substance.

(7) Preparation of 6-[2-(5-ethyl-1,3,4-thiadiazol-2-yl)ethyl]-4-morpholino-2-[3-(2-propenyloxycarbonylamino) benzylamino]pyridine Using the compound obtained by the above reaction, the above identified compound was obtained as a pale yellow solid in the same manner as in Example 1-(6) and (7) except that benzyl bromide was changed to 3-(2-propenyloxycarbonylamino)benzyl bromide.

$^1$H-NMR(CDCl$_3$) δ: 1.38(3H, t, J=7.5 Hz), 3.08(2H, q, J=7.5 Hz), 3.08(2H, t, J=7.3 Hz), 3.20(4H, t, J=5.1 Hz), 3.54(2H, t, J=7.3 Hz), 3.76(4H, t, J=5.1 Hz), 4.43(2H, d, J=6.0 Hz), 4.65(2H, d, J=5.7 Hz), 5.26(1H, dq, J=1.3 Hz, 10.5 Hz), 5.37(1H, dq, J=1.3 Hz, 17.2 Hz), 5.50 (1H, d, J=2.0 Hz), 5.95(1H, ddt, J=10.5 Hz, 17.2 Hz), 6.03(1H, d, J=2.0 Hz), 6.97(1H, s), 7.05(1H, d, J=7.3 Hz), 7.29(1H, d, J=7.3 Hz), 7.26(1H, d, J=7.3 Hz), 7.39(1H, s).

Examples 23 and 24 were obtained in the same manner as in Example 22-(5) to (7) except that propionic anhydride was changed to the corresponding carboxylic anhydride.

EXAMPLE 23

6-[2-(5-isopropyl-1,3,4-thiadiazol-2-yl)ethyl]-4-morpholino-2-[3-(2-propenyloxycarbonylamino) benzylamino]pyridine $^1$H-NMR(CDCl$_3$) δ: 1.37(3H, s), 1.40(3H, s), 3.00(2H, t, J=7.6 Hz), 3.15(4H, t, J=4.9 Hz), 3.40(1H, q, J=6.9 Hz), 3.49(2H, t, J=7.6 Hz), 3.77(4H, t, J=4.9 Hz), 4.45(2H, d, J=5.8 Hz), 4.66(2H, d, J=5.8 Hz), 4.95(1H, brs), 5.26(1H, dd, J=1.2 Hz, 9.0 Hz), 5.36(1H, dd, J=1.2 Hz, 15.9 Hz), 5.55(1H, d, J=1.8 Hz), 5.95(1H, ddt, J=5.8 Hz, 9.0 Hz, 15.9 Hz), 6.00(1H, d, J=1.8 Hz), 6.94(1H, brs), 7.06(1H, d, J=7.5 Hz), 7.26(1H, d, J=7.5 Hz, 8.1 Hz), 7.32(1H, d, J=8.1 Hz), 7.39(1H, s).

EXAMPLE 24

4-morpholino-2-[3-(2-propenyloxycarbonylamino) benzylamino]-6-[2-(5-propyl-1,3,4-thiadiazol-2-yl) ethyl]pyridine $^1$H-NMR(CDCl$_3$) δ: 0.99(3H, t, J=7.3 Hz), 1.77(2H, tq, J=7.3 Hz, 7.6 Hz), 3.00(4H, t, J=7.6 Hz), 3.15(4H, t, J=4.9 Hz), 3.50(2H, t, J=7.6 Hz), 3.77(4H, t, J=4.9 Hz), 4.45(2H, d, J=4.9 Hz), 4.65(2H, d, J=2.7 Hz), 4.95(1H, brs), 5.26(1H, dd, J=1.4 Hz, 10.3 Hz), 5.36 (1H, dd, J=1.4 Hz, 17.2 Hz), 5.55(1H, s), 5.97(1H, ddt, J=2.7 Hz, 10.3 Hz, 17.2 Hz), 6.00(1H, s), 6.90(1H, brs), 7.05(1H, d, J=7.6 Hz), 7.20–7.31 (2H, m), 7.38(1H, s).

EXAMPLE 25

Preparation of (±)-6-(5-ethyl-1,3,4-thiadiazol-2-ylthiomethyl)-4-(2-methylpiperidino)-2-[3-(2-propenyloxycarbonylamino)benzylamino]pyridine (1) Preparation of dimethyl (±)-4-(2-methylpiperidino)-2,6-pyridinedicarboxylate 4-chloro-2,6-pyridinedicarboxylic acid (3.5 g) was dissolved in 2-methylpiperidine (25 ml), and cupric oxide (207 mg) was added thereto, followed by heating at 180° C. for 14 hours in a sealed tube. Cupric oxide was filtered off, and 2-methylpiperidine was distilled off under reduced pressure. The residue was dissolved in 10% hydrochloric acid-methanol (50 ml), followed by refluxing under heating for 20 hours. The reaction solution was concentrated under reduced pressure, and then, chloroform and water were added to the residue. The mixture was made alkaline with a 1 N sodium hydroxide aqueous solution, and then, the organic layer was separated and dried over anhydrous magnesium sulfate. The solvent was distilled off under reduced pressure, and the residue was purified by silica gel column chromatography (hexane/ethyl acetate=1:1→2:5) to obtain the above identified compound (5.07 g) as a white solid.

(2) Preparation of tert-butyl (±)-N-[6-(5-ethyl-1,3,4-thiadiazol-2-ylthiomethyl)-4-(2-methylpiperidino)-2-pyridyl]carbamate Using the compound obtained by the above reaction, the above identified compound was obtained as a white solid in the same manner as in Example 1-(2) to (5).

(3) Preparation of (±)-2-[N-tert-butoxycarbonyl-N-(3-nitrobenzyl)amino]-6-(5-ethyl-1,3,4-thiadiazol-2-ylthiomethyl)-4-(2-methylpiperidino)pyridine Using the compound obtained by the above reaction, the above identified compound was obtained as a pale yellow oily substance in the same manner as in Example 8-(3).

(4) Preparation of (±)-2-[N-(3-aminobenzyl)-N-tert-butoxycarbonylamino]-6-(5-ethyl-1,3,4-thiadiazol-2-ylthiomethyl)-4-(2-methylpiperidino)pyridine The compound (377 mg) obtained by the above reaction was dissolved in ethanol (6 ml) and stannous chloride (489 mg) was added, followed by stirring at 50° C. for one hour and further at 60° C. for one hour. The solvent was distilled off under reduced pressure, and a saturated sodium hydrogen carbonate aqueous solution was added to the residue. Then, the pH was adjusted from 7 to 8, followed by extraction with ethyl acetate. The organic layer was dried over anhydrous sodium sulfate, and then, the solvent was distilled off under reduced pressure. The residue was purified by silica gel column chromatography (ethyl acetate/heptane=2/3→1/1) to obtain the above identified compound (189 mg).

(5) Preparation of (±)-6-(5-ethyl-1,3,4-thiadiazol-2-ylthiomethyl)-4-(2-methylpiperidino)-2-[3-(2-propenyloxycarbonylamino)benzylamino]pyridine Using the compound obtained by the above reaction, the above identified compound was obtained as a pale yellow solid in the same manner as in Example 8-(5) and Example 1-(7).

$^1$H-NMR(CDCl$_3$) δ: 1.01(3H, d, J=6.6 Hz), 1.37(3H, t, J=7.6 Hz), 1.58–1.80(6H, m), 2.84(1H, dt, J=3.0 Hz, 12.5 Hz), 3.05(2H, q, J=7.6 Hz), 3.45(1H, dt, J=3.0 Hz, 12.5 Hz), 4.05(1H, m), 4.39(2H, s), 4.40(2H, d, J=4.9 Hz), 4.65(2H, d, J=5.6 Hz), 5.13–5.27(1H, m), 5.24(1H, dd, J=1.1 Hz, 10.3 Hz), 5.34(1H, dd, J=1.1 Hz, 17.0 Hz), 5.51 (1H, d, J=2.0 Hz), 5.95(1H, ddt, J=5.6 Hz, 10.3 Hz, 17.0 Hz), 6.29(1H, d, J=2.0 Hz), 6.83(1H, brs), 7.05(1H, d, J=7.6 Hz), 7.26(1H, dd, J=6.3 Hz, 7.6 Hz), 7.34(1H, s), 7.36(1H, d, J=6.3 Hz).

EXAMPLE 26

Preparation of (±)-6-[1-(5-ethyl-1,3,4-thiadiazol-2-ylthio)ethyl]-4-moroholino-2-[3-(2-propenyloxycarbonylamino)benzylamino]pyridine (1) Preparation of 2-{N-tert-butoxycarbonyl-N-[3-(2-propenyloxycarbonylamino)benzyl]amino}-6-formyl-4-morpholinopyridine Using the compound obtained in Example 8-(6), the above identified compound was obtained in the same manner as in Example 22-(2).

(2) Preparation of (±)-2-{N-tert-butoxycarbonyl-N-[3-(2-propenyloxycarbonylamino)benzyl]amino}-6-(1-hydroxyethyl)-4-morpholinopyridine The compound (42 mg) obtained by the above reaction is dissolved in tetrahydrofuran (1.5 ml), and methylmagnesium bromide (a 0.95 N tetrahydrofuran solution, 0.15 ml) was added at −65° C., followed by stirring at the same temperature for 30 minutes. Ethyl acetate was added thereto, followed by washing with water and a saturated sodium chloride aqueous solution and drying over anhydrous sodium sulfate. Then, the solvent was distilled off under reduced pressure, and the residue was purified by silica gel column chromatography (ethyl acetate/heptane=2/3→2/1) to obtain the above identified compound (189 mg).

(3) Preparation of (±)-6-[1-(5-ethyl-1,3,4-thiadiazol-2-ylthio)ethyl]-4-morpholino-2-[3-(2-propenyloxycarbonylamino)benzylamino]pyridine Using the compound obtained by the above reaction, the above identified compound was obtained as a pale yellow solid in the same manner as in Example 8-(7) and (8) except that 5-ethyl-3-mercapto-1,2,4-triazole was changed to 5-ethyl-2-mercapto-1,3,4-thiadiazole.

$^1$H-NMR(CDCl$_3$) δ: 1.36(3H, t, J=7.5 Hz), 1.77(3H, d, J=6.9 Hz), 3.05(2H, q, J=7.5 Hz), 3.16(4H, dd, J=4.7 Hz, 5.0 Hz), 3.76(4H, dd, J=4.7 Hz, 5.0 Hz), 4.44(2H, d, J=4.7 Hz), 4.65(2H, d, J=5.7 Hz), 4.89 (1H, q, J=6.9 Hz), 4.99–5.18 (1H, m), 5.25(1H, d, J=10.7 Hz), 5.35 (1H, d, J=17.1 Hz), 5.55(1H, d, J=1.9 Hz), 5.96(1H, ddt, J=5.7 Hz, 10.7 Hz, 17.1 Hz), 6.22(1H, d, J=1.9 Hz), 6.84(1H, brs), 7.06(1H, d, J=7.2 Hz), 7.26(1H, dd, J=7.2 Hz, 8.3 Hz), 7.33(1H, d, J=8.3 Hz), 7.39(1H, s).

EXAMPLE 27

Preparation of 6-(5-ethyl-1,3,4-thiadiazol-2-ylthiomethyl)-4-morpholino-2-[6-(2-propenyloxycarbonylamino)-2-pyridylmethylamino]pyridine The above identified compound was obtained as a pale yellow solid in the same manner as in Example 1-(6), Example 4-(2) and (3) and Example 1-(7) except that benzyl bromide was changed to ethyl 6-chloromethylpyridine-2-carboxylate.

$^1$H-NMR(CDCl$_3$) δ: 1.38(3H, t, J=7.6 Hz), 3.06 (2H, q, J=7.6 Hz), 3.19(4H, dd, J=4.9 Hz, 5.0 Hz), 3.78(4H, dd, J=4.9 Hz, 5.0 Hz), 4.44 (2H, s), 4.46(2H, d, J=5.4 Hz), 4.69(2H, dt, J=1.4 Hz, 5.6 Hz), 5.28 (1H, dt, J=1.4 Hz, 10.4 Hz), 5.38(1H, dt, J=1.4 Hz, 17.2 Hz), 5.40–5.50(1H, m), 5.62(1H, d, J=2.0 Hz), 5.96(1H, ddt, J=5.6 Hz, 10.4 Hz, 17.2 Hz), 6.33(1H, d, J=2.0 Hz), 7.02(1H, d, J=7.7 Hz), 7.45(1H, brs), 7.64(1H, t, J=7.7 Hz), 7.82(1H, d, J=7.7 Hz).

EXAMPLE 28

Preparation of 6-(5-ethyl-1,3,4-thiadiazol-2-ylthiomethyl)-4-morpholino-2-[2-(2-propenyloxycarbonylamino)-4-pyridylmethylamino] pyridine The above identified compound was obtained as a white solid in the same manner as in Example 27 except that ethyl 6-chloromethylpyridine-2-carboxylate was changed to ethyl 4-chloromethylpyridine-2-carboxylate.

$^1$H-NMR(CDCl$_3$) δ: 1.38(3H, t, J=7.6 Hz), 3.06(2H, q, J=7.6 Hz), 3.17(4H, dd, J=4.9 Hz, 5.0 Hz), 3.77(4H, dd, J=4.9 Hz, 5.0 Hz), 4.41 (2H, s), 4.49(2H, d, J=6.2 Hz), 4.69(2H, dt, J=1.4 Hz, 5.7 Hz), 4.90–5.10(1H, m), 5.28(1H, dq, J=1.4 Hz, 10.5 Hz), 5.37(1H, dq, J=1.4 Hz, 17.2 Hz), 5.56(1H, d, J=2.0 Hz), 5.97(1H, ddt, J=5.6 Hz, 10.5 Hz, 17.2 Hz), 6.33(1H, d, J=2.0 Hz), 7.03(1H, dd, J=1.5 Hz, 5.3 Hz), 7.98 (1H, brs), 8.15(1H, brs), 8.19(1H, d, J=5.3 Hz).

EXAMPLE 29

Preparation of 6-(5-ethyl-1,3,4-thiadiazol-2-ylthiomethyl)-4-morpholino-2-(3-propyloxycarbonylaminobenzylamino)pyridine Using the compound of Example 5-(1), the above identified compound was obtained as a colorless oily substance in the same manner as in Example 8-(5) and Example 1-(7) except that allyl chloroformate was changed to propyl chloroformate.

$^1$H-NMR(CDCl$_3$) δ: 0.97(3H, t, J=7.1 Hz), 1.38(3H, t, J=7.6 Hz), 1.69(2H, sext, J=7.1 Hz), 3.06(2H, q, J=7.6 Hz), 3.16(4H, dd, J=4.8 Hz, 5.1 Hz), 3.76(4H, dd, J=4.8 Hz, 5.1 Hz), 4.11(2H, t, J=7.1 Hz), 4.41 (2H, s), 4.42(2H, d, J=4.9 Hz), 5.56(1H, d, J=2.0 Hz), 6.31(1H, d, J=2.0 Hz), 6.74(1H, brs), 7.04(1H, brd, J=7.7 Hz), 7.25(1H, t, J=7.7 Hz), 7.31 (1H, brd, J=7.7 Hz), 7.38(1H, brs).

Examples 30 to 32 were obtained in the same manner as in Example 29 except that propyl chloroformate was changed to the corresponding alkyl chloroformate.

EXAMPLE 30

6-(5-ethyl-1,3,4-thiadiazol-2-ylthiomethyl)-2-(3-methoxycarbonylaminobenzylamino)-4-morpholinopyridine $^1$H-NMR(CDCl$_3$) δ: 1.38(3H, t, J=7.6 Hz), 3.06(2H, q, J=7.6 Hz), 3.16(4H, dd, J=4.9 Hz, 5.0 Hz), 3.76(3H, s), 3.76(4H, dd, J=4.9 Hz, 5.0 Hz), 4.41(2H, s), 4.42(2H, d, J=6.1 Hz), 4.97–5.10(1H, m), 5.56 (1H, d, J=2.0 Hz), 6.31 (1H, d, J=2.0 Hz), 6.80(1H, brs), 7.05(1H, brd, J=7.6 Hz), 7.23(1H, t, J=7.6 Hz), 7.32(1H, brd, J=7.6 Hz), 7.38 (1H, brs).

EXAMPLE 31

6-(5-ethyl-1,3,4-thiadiazol-2-ylthiomethyl)-2-(3-isopropyloxycarbonylaminobenzylamino)-4-morpholinopyridine $^1$H-NMR(CDCl$_3$) δ: 1.29(6H, d, J=6.3 Hz), 1.37(3H, t, J=7.6 Hz), 3.06(2H, q, J=7.6 Hz), 3.16(4H, dd, J=4.9 Hz, 5.0 Hz), 3.76(4H, dd, J=4.9 Hz, 5.0 Hz), 4.42(2H, s), 4.42(2H, d, J=5.6 Hz), 4.95–5.05(1H, m), 5.00 (1H, sept, J=6.3 Hz), 5.57(1H, d, J=2.0 Hz), 6.31(1H, d, J=2.0 Hz), 6.64(1H, brs), 7.04(1H, brd, J=7.0 Hz), 7.25(1H, t, J=7.0 Hz), 7.30(1H, brd, J=7.0 Hz), 7.39(1H, brs).

EXAMPLE 32

6-(5-ethyl-1,3,4-thiadiazol-2-ylthiomethyl)-4-morpholino-2-(3-pentyloxycarbonylaminobenzylamino)pyridine $^1$H-NMR(CDCl$_3$) δ: 0.88–0.95(3H, m), 1.30–1.42(4H, m), 1.37 (3H, t, J=7.6 Hz), 1.60–1.73(2H, m), 3.06(2H, q, J=7.6 Hz), 3.16 (4H, dd, J=4.9 Hz, 5.1 Hz), 3.76(4H, dd, J=4.9 Hz, 5.1 Hz), 4.14(2H, t, J=6.7 Hz), 4.41(2H, s), 4.42(2H, d, J=4.5 Hz), 4.95–5.05(1H, m), 5.56(1H, d, J=2.0 Hz), 6.31(1H, d, J=2.0 Hz), 6.73(1H, s), 7.04 (1H, brd, J=7.6 Hz), 7.25(1H, t, J=7.6 Hz), 7.31 (1H, brd, J=7.6 Hz), 7.38(1H, brs).

EXAMPLE 33

Preparation of 2-(3-aminobenzylamino)-6-(5-ethyl-1,3,4-thiadiazol-2-ylthiomethyl)-4-morpholinopyridine Using the compound obtained by the Example 5-(1), the above identified compound was obtained in the same manner as in Example 1-(7).

$^1$H-NMR(CDCl$_3$) δ: 1.37(3H, t, J=7.6 Hz), 3.05(2H, q, J=7.6 Hz), 3.19(4H, dd, J=4.9 Hz, 5.0 Hz), 3.77(4H, dd, J=4.9 Hz, 5.0 Hz), 4.43 (2H, s), 4.51(2H, d, J=5.9 Hz), 5.27–5.38(1H, m), 5.56(1H, d, J=2.0 Hz), 5.55–5.70(1H, m), 6.34(1H, d, J=2.0 Hz), 6.30–6.50(1H, m), 7.41(1H, t, J=7.6 Hz), 7.50(1H, d, J=7.6 Hz), 7.74(1H, d, J=7.6 Hz), 7.87(1H, s).

EXAMPLE 34

Preparation of 6-(5-ethyl-1,3,4-thiadiazol-2-ylthiomethyl)-4-morpholino-2-[3-(3-methyl-2-butenyloxycarbonylamino)benzylamino]pyridine The compound (17.4 mg) obtained in Example 33 and 4-dimethylaminopyridine (5.8 mg) were dissolved in chloroform (1.0 ml), and a solution of phenyl chlorocarbonate (7.4 mg) in chloroform (0.5 ml) was added thereto, followed by stirring at room temperature for one hour. Further, a solution of triethylamine (32.2 mg) and 3-methyl-2-buten-1-ol (28 mg) in chloroform, was added, thereto, followed by stirring at room temperature overnight, at 55° C. for 6 hours, at 70° C. for 3 hours and further at 80° C. for 3 hours. The solvent was distilled off under reduced pressure, and the residue was purified by thin layer chromatography for separation (silica gel 60F$_{254}$, manufactured by Merck Company, chloroform:methanol=10:1) to obtain the above identified compound (13.6 mg) as a white solid.

$^1$H-NMR(CDCl$_3$) δ: 1.38(3H, t, J=7.5 Hz), 1.78(6H, s), 3.06(2H, q, J=7.5 Hz), 3.16–3.21(4H, m), 3.73–3.78(4H, m), 4.40(2H, brs), 4.43(2H, s), 4.65(2H, d, J=7.3 Hz), 5.34–5.42 (1H, m), 5.53(1H, d, J=2.0 Hz), 6.12(1H, brs), 6.34(1H, d, J=2.0 Hz), 6.71 (1H, brs), 7.04(1H, d, J=6.8 Hz), 7.22–7.32 (2H, m), 7.39(1H, brs).

EXAMPLE 35

Preparation of (±)-6-(5-ethyl-1,3,4-thiadiazol-2-ylthiomethyl)-2-[3-(5-methyl-2-thiazolin-2-ylamino)benzylamino]-4-morpholinopyridine (1) Preparation of 2-{N-(tert-butoxycarbonyl)-N-[3-(2-propenylaminothiocarbonylamino)benzyl]amino}-6-(5-ethyl-1,3,4-thiadiazol-2-ylthiomethyl)-4-morpholinopyridine The compound (27.1 mg) obtained in Example 5-(1) was dissolved in chloroform (0.7 ml), and a solution of 2-propenylthioisocyanate (7.5 mg) in chloroform (0.3 ml), was added, followed by stirring at room temperature overnight. Further, a solution of 2-propenylthioisocyanate (22.5 mg) in chloroform (0.6 ml) was added, followed by stirring at 45° C. for 3 hours and at 60° C. for 3 hours. Ethyl acetate was added thereto, followed by sequential washing with a saturated sodium hydrogen carbonate aqueous solution and a saturated sodium chloride aqueous solution. The product was dried over anhydrous sodium sulfate and then, the solvent was distilled off under reduced pressure. The residue was purified by thin layer chromatography for separation (silica gel 60F$_{254}$, manufactured by Merck Company, ethyl acetate) to obtain the above identified compound (30.1 mg) as a white solid.

(2) Preparation of (±)-6-(5-ethyl-1,3,4-thiadiazol-2-ylthiomethyl)-2-[3-(5-methyl-2-thiazolin-2-ylamino)benzylamino]-4-morpholinopyridine Using the compound obtained by the above reaction, the above identified compound was obtained as a pale yellow oily substance in the same manner as in Example 1-(7).

$^1$H-NMR(CDCl$_3$) δ: 1.38(3H, t, J=7.5 Hz), 1.42(3H, d, J=6.6 Hz), 3.06(2H, q, J=7.5 Hz), 3.14–3.20(4H, m), 3.40–3.50(1H, m), 3.73–3.78(4H, m), 3.80(1H, brs), 3.81–3.93(2H, m), 4.41(2H, d, J=7.1 Hz), 4.42(2H, s), 5.24(1H, brs), 5.54(1H, d, J=2.0 Hz), 6.32(1H, d, J=2.0 Hz), 7.00–7.12(3H, m), 7.23(1H, d, J=7.6 Hz).

EXAMPLE 36

Preparation of 2-(2-acetamidobenzylamino)-6-(5-ethyl-1,3,4-thiadiazol-2-ylthiomethyl)-4-morpholinopyridine (1) Preparation of 2-{N-tert-butoxycarbonyl-N-[2-(2-propenyloxycarbonylamino)benzyl]amino}-6-(5-ethyl-1,3,4-thiadiazol-2-ylthiomethyl)-4-morpholinopyridine The above identified compound was obtained in the same manner as in Example 1-(6) and Example 4-(2) and (3) except that benzyl bromide was changed to methyl 2-bromomethylbenzoate.

(2) Preparation of 2-[N-(2-aminobenzyl)-N-(tert-butoxycarbonyl)amino]-6-(5-ethyl-1,3,4-thiadiazol-2-ylthiomethyl)-4-morpholinopyridine The compound (39.1 mg) obtained by the above reaction, palladium (II) acetate (0.2 mg) and trisodium 3,3',3"-phosphinidinetris(benzenesulfonate) (1 mg) were dissolved in acetonitrile (0.6 ml) and water (0.1 ml), and diethylamine (32 μl) was added, followed by stirring at room temperature for one hour. Ethyl acetate was added thereto, followed by washing with water and a saturated sodium chloride aqueous solution and drying over anhydrous magnesium sulfate. Then, the solvent was distilled off under reduced pressure to obtain the above identified compound (30 mg) as a yellow solid.

(3) Preparation of 2-(2-acetamidobenzylamino)-6-(5-ethyl-1,3,4-thiadiazol-2-ylthiomethyl)-4-morpholinopyridine The compound (30 mg) obtained by the above reaction was dissolved in chloroform (1 ml), and 4-dimethylaminopyridine (8 mg) and acetyl bromide (4.8 μl) were added thereto, followed by stirring at room temperature for 3 hours. Chloroform was added thereto, and the mixture was washed with a saturated sodium chloride aqueous solution and dried over anhydrous magnesium sulfate. Then, the solvent was distilled off under reduced pressure. The residue was treated in the same manner as in Example 1-(7) to obtain the above identified compound (22 mg) as a pale yellow oily substance.

¹H-NMR(CDCl₃) δ: 1.37(3H, t, J=7.5 Hz), 2.08(3H, s), 3.05(2H, q, J=7.5 Hz), 3.19(4H, dd, J=4.7 Hz, 4.9 Hz), 3.77(4H, dd, J=4.7 Hz, 4.9 Hz), 4.49(2H, s), 4.49–4.51(2H, m), 5.10–5.29(1H, m), 5.62(1H, d, J=1.9 Hz), 6.37(1H, d, J=1.9 Hz), 7.09(1H, dd, J=7.5 Hz, 8.0 Hz), 7.23–7.32(2H, m), 7.92(1H, d, J=8.0 Hz), 8.80(1H, brs).

EXAMPLE 37

Preparation of 2-[3-(cyclopropylmethyloxycarbonylamino)benzylamino]-6-(5-ethyl-1,3,4-thiadiazol-2-ylthiomethyl)-4-morpholinopyridine To a solution of the compound (17 mg) obtained in Example 5-(1) in chloroform (1 ml), N,N'-carbonyldiimidazole (25 mg) was added, followed by stirring at room temperature for two hours. To the reaction solution, triethylamine (41 μl) and cyclopropanemethanol (25 μl) were added, followed by stirring at room temperature overnight. Water was added thereto, and the mixture was extracted three times with chloroform. The organic layer was washed with water and dried over anhydrous magnesium sulfate. Then, the solvent was distilled off under reduced pressure, and the residue was treated in the same manner as in Example 1-(7) to obtain the above identified compound (6.4 mg) as a pale yellow oily substance.

¹H-NMR(CDCl₃) δ: 0.32(2H, q, J=4.5 Hz), 0.58(2H, q, J=4.5 Hz), 1.16(1H, m), 1.37(3H, t, J=7.6 Hz), 3.05(2H, q, J=7.6 Hz), 3.16(4H, t, J=5.0 Hz), 3.76(4H, t, J=5.0 Hz), 3.96(2H, d, J=7.3 Hz), 4.42(4H, s), 5.15(1H, brs), 5.55(1H, d, J=2.1 Hz), 6.31(1H, d, J=2.1 Hz), 7.03(1H, s) 7.05(1H, d, J=7.2 Hz), 7.26(1H, t, J=7.8 Hz), 7.30(1H, d, J=7.2 Hz), 7.38(1H, brs).

Using the compound obtained in Example 33, Examples 38 to 42 were obtained in the same manner as in Example 37 except that cyclopropanemethanol was changed to the corresponding alcohol.

EXAMPLE 38

6-(5-ethyl-1,3,4-thiadiazol-2-ylthiomethyl)-2-[3-(2-furylmethyloxycarbonylamino)benzylamino]-4-morpholinopyridine ¹H-NMR(CDCl₃) δ: 1.36(3H, t, J=7.6 Hz), 3.04(2H, q, J=7.6 Hz), 3.16(4H, dd, J=4.8 Hz, 5.0 Hz), 3.76(4H, dd, J=4.8 Hz, 5.0 Hz), 4.41 (2H, s), 4.42(2H, d, J=4.2 Hz), 5.14(2H, s), 5.17(1H, brs), 5.55(1H, d, J=2.0 Hz), 6.32(1H, d, J=2.0 Hz), 6.37(1H, dd, J=1.9 Hz, 3.3 Hz), 6.45(1H, d, J=3.3 Hz), 6.86(1H, brs), 7.05(1H, d, J=7.3 Hz), 7.21–7.33 (2H, m), 7.37(1H, brs), 7.43(1H, d, J=1.9 Hz).

EXAMPLE 39

6-(5-ethyl-1,3,4-thiadiazol-2-ylthiomethyl)-4-morpholino-2-[3-(2-thienylmethyloxycarbonylamino)benzylamino]pyridine ¹H-NMR(CDCl₃) δ: 1.36(3H, t, J=7.6 Hz), 3.04(2H, q, J=7.6 Hz), 3.16(4H, dd, J=4.8 Hz, 5.1 Hz), 3.75(4H, dd, J=4.8 Hz, 5.1 Hz), 4.41 (2H, s), 4.42(2H, d, J=3.9 Hz), 5.26(1H, brs), 5.33(2H, s), 5.55(1H, d, J=2.0 Hz), 6.32(1H, d, J=2.1 Hz), 6.88(1H, brs), 6.99(1H, dd, J=3.5 Hz, 5.1 Hz), 7.05(1H, d, J=7.4 Hz), 7.13(1H, d, J=3.5 Hz), 7.21–7.30(2H, m), 7.33(1H, d, J=5.1 Hz), 7.37(1H, brs).

EXAMPLE 40

6-(5-ethyl-1,3,4-thiadiazol-2-ylthiomethyl)-2-[3-(3-furylmethyloxycarbonylamino)benzylamino]-4-morpholinopyridine ¹H-NMR(CDCl₃) δ: 1.37(3H, t, J=7.6 Hz), 3.05(2H, q, J=7.6 Hz), 3.17(4H, t, J=4.9 Hz), 3.76(4H, t, J=4.9 Hz), 4.41(2H, s), 4.42(2H, d, J=4.4 Hz), 5.06(2H, s), 5.17(1H, brs), 5.55(1H, d, J=2.0 Hz), 6.32(1H, d, J=2.0 Hz), 6.45(1H, d, J=2.0 Hz), 6.47(1H, d, J=2.0 Hz), 6.83(1H, s), 7.05(1H, d, J=7.3 Hz), 7.23–7.93(3H, m), 7.51(1H, brs).

EXAMPLE 41

6-(5-ethyl-1,3,4-thiadiazol-2-ylthiomethyl)-4-morpholino-2-[3-(3-tetrahydrofuranylmethyloxycarbonylamino)benzylamino]pyridine ¹H-NMR(CDCl₃) δ: 1.48(3H, t, J=7.6 Hz), 1.63–1.71(1H, m), 2.01–2.10(1H, m), 2.57–2.68(1H, m), 3.05(2H, q, J=7.6 Hz), 3.16 (4H, t, J=5.0 Hz), 3.62(1H, dd, J=5.7 Hz, 8.9 Hz), 3.76(5H, t, J=5.0 Hz), 3.83–3.89(2H, m), 4.05(1H, dd, J=6.7 Hz, 11.0 Hz), 4.18(1H, dd, J=6.7 Hz, 11.0 Hz), 4.42(2H, s), 4.44(2H, d, J=5.3 Hz), 5.02(1H, brt, J=5.3 Hz), 5.56(1H, d, J=1.9 Hz), 6.30(1H, d, J=1.9 Hz), 6.85 (1H, brs), 7.05(1H, d, J=7.2 Hz), 7.23–7.36(3H, m).

EXAMPLE 42

6-(5-ethyl-1,3,4-thiadiazol-2-ylthiomethyl)-4-morpholino-2-[3-(2-tetrahydrofuranylmethyloxycarbonylamino)benzylamino]pyridine ¹H-NMR(CDCl₃) δ: 1.37(3H, t, J=7.6 Hz), 1.63(1H, m), 1.95 (2H, m), 3.06(2H, q, J=7.6 Hz), 3.16(4H, t, J=5.5 Hz), 3.76(6H, t, J=5.5 Hz), 3.82(1H, m), 3.90(1H, m), 4.05(1H, dd, J=7.5 Hz, 11.1 Hz), 4.16(1H, m), 4.26(1H, dd, J=2.7 Hz, 10.8 Hz), 4.41(4H, s), 5.25(1H, brs), 5.55(1H, d, J=1.9 Hz), 6.31(1H, d, J=1.9 Hz), 6.83 (1H, dd, J=2.1 Hz, 8.5 Hz), 7.04(1H, dd, J=2.1 Hz, 8.5 Hz), 7.22–7.34 (2H, m).

EXAMPLE 43

Preparation of 2-[3-(cyclopropylaminocarbonylamino)benzylamino]-6-(5-ethyl-1,3,4-thiadiazol-2-ylthiomethyl)-4-morpholinopyridine Using the compound obtained in Example 5-(1), the above identified compound was obtained as a pale yellow oily substance in the same manner as in Example 34 and Example 1-(7), except that 3-methyl-2-buten-1-ol was changed to cyclopropylamine.

¹H-NMR(CDCl₃) δ: 0.60–0.63(2H, m), 0.76–0.83(2H, m), 1.37 (3H, t, J=7.6 Hz), 2.57–2.62(1H, m), 3.05(2H, q, J=7.6 Hz), 3.15 (4H, dd, J=4.8 Hz, 5.1 Hz), 3.75(4H, dd, J=4.8 Hz, 5.1 Hz), 4.37(2H, s), 4.39(2H, d, J=5.8 Hz), 5.05–5.15(1H, m), 5.25–5.35(1H, m), 5.55(1H, d, J=2.0 Hz), 6.26(1H, d, J=2.0 Hz), 6.98(1H, d, J=7.6 Hz), 7.22(1H, dd, J=7.6 Hz, 7.8 Hz), 7.22(1H, brs), 7.32(1H, brs), 7.46 (1H, d, J=7.8 Hz).

Examples 44 to 46 were obtained in the same manner as in Example 34 except that cyclopropylamine was changed to the corresponding alcohol or aniline.

EXAMPLE 44

6-(5-ethyl-1,3,4-thiadiazol-2-ylthiomethyl)-4-morpholino-2-[3-(2-propynyloxycarbonylamino)benzylamino]pyridine ¹H-NMR(CDCl₃) δ: 1.37(3H, t, J=7.6 Hz), 2.51(1H, t, J=2.5 Hz), 3.06(2H, q, J=7.6 Hz), 3.17(4H, dd, J=4.8 Hz, 5.0 Hz), 3.76(4H, dd, J=4.8 Hz, 5.0 Hz), 4.41(2H, s), 4.43(2H, d, J=5.9 Hz), 4.77(2H, d, J=2.5 Hz), 5.56(1H, d, J=2.0 Hz), 6.32(1H, d, J=2.0 Hz), 6.90(1H, brs), 7.07(1H, brd, J=7.6 Hz), 7.26(1H, t, J=7.6 Hz), 7.32(1H, brd, J=7.6 Hz), 7.39 (1H, brs).

EXAMPLE 45

6-(5-ethyl-1,3,4-thiadiazol-2-ylthiomethyl)-2-[3-(2-methoxyethyloxycarbonylamino)benzylamino]-4-morpholinopyridine $^1$H-NMR(CDCl$_3$) δ: 1.38 (3H, t, J=7.6 Hz), 3.06(2H, q, J=7.6 Hz), 3.16(4H, t, J=5.3 Hz), 3.41(3H, s), 3.63(2H, t, J=4.7 Hz), 3.75(4H, t, J=5.0 Hz), 4.32(2H, t, J=4.6 Hz), 4.41 (4H, s), 5.56(1H, d, J=2.1 Hz), 6.31(1H, d, J=1.9 Hz), 6.78(1H, brs), 7.07(1H, m) 7.26(2H, m), 7.61 (1H, s).

EXAMPLE 46

6-(5-ethyl-1,3,4-thiadiazol-2-ylthiomethyl)-2-[3-(3-hydroxyphenylaminocarbonylamino)benzylamino]-4-moroholinopyridine $^1$H-NMR(CDCl$_3$) δ: 1.35(3H, t, J=7.6 Hz), 3.03(2H, q, J=7.6 Hz), 3.16(4H, dd, J=4.5 Hz, 5.0 Hz), 3.71(4H, dd, J=4.5 Hz, 5.0 Hz), 4.28 (2H, m), 4.32(2H, s), 5.50(1H, d, J=1.7 Hz), 5.78–6.02(1H, brs), 6.25(1H, d, J=1.7 Hz), 6.51 (1H, d, J=7.3 Hz), 6.84(1H, d, J=7.7 Hz), 7.02–7.15(5H, m), 7.47(1H, brd, J=8.1 Hz), 7.92(1H, brs), 8.23(1H, brs).

EXAMPLE 47

Preparation of 6-(5-ethyl-1,3,4-thiadiazol-2-ylthiomethyl)-2-(3-ethyloxycarbonylaminobenzylamino)-4-morpholinopyridine Using the compound obtained in Example 33, the above identified compound was obtained as a colorless oily substance in the same manner as in Example 8-(5) except that allyl chloroformate was changed to ethyl chloroformate.

$^1$H-NMR(CDCl$_3$) δ: 1.30(3H, t, J=7.1 Hz), 1.37(3H, t, J=7.6 Hz), 3.06(2H, q, J=7.6 Hz), 3.16(4H, dd, J=4.8 Hz, 5.0 Hz), 3.75(4H, dd, J=4.8 Hz, 5.0 Hz), 4.21(2H, q, J=7.1 Hz), 4.41 (2H, s), 4.42(2H, d, J=4.9 Hz), 4.95–5.15(1H, m), 5.56(1H, d, J=1.9 Hz), 6.31(1H, d, J=1.9 Hz), 6.68(1H, brs), 7.04(1H, d, J=7.1 Hz), 7.22–7.29(2H, m)7.38(1H, brs).

EXAMPLE 48

Preparation of 6-(5-ethyl-1,3,4-thiadiazol-2-ylthiomethyl)-2-(3-isobutyloxycarbonylaminobenzylamino)-4-morpholinopyridine The above identified compound was obtained as a pale yellow oily substance in the same manner as in Example 47 except that ethyl chloroformate was changed to isobutyl chloroformate.

$^1$H-NMR(CDCl$_3$) δ: 0.95(6H, d, J=6.7 Hz), 1.37(3H, t, J=7.6 Hz), 1.96(1H, m), 3.06(2H, q, J=7.6 Hz), 3.16(4H, dd, J=4.8 Hz, 5.0 Hz), 3.76(4H, dd, J=4.8 Hz, 5.0 Hz), 3.94(2H, d, J=6.6 Hz), 4.41(2H, s), 4.42(2H, d, J=5.8 Hz), 4.90–5.05 (1H, m), 5.56(1H, d, J=2.0 Hz), 6.30(1H, d, J=2.0 Hz), 6.70(1H, brs), 7.04(1H, d, J=7.2 Hz), 7.23–7.35(2H, m) 7.38(1H, s).

EXAMPLE 49

Preparation of 6-(5-ethyl-1,3,4-thiadiazol-2-ylthiomethyl)-4-piperidino-2-[3-(2-propenyloxycarbonylamino)benzylamino]pyridine (1) Preparation of tert-butyl N-[6-(5-ethyl-1,3,4-thiadiazol-2-ylthiomethyl)-4-piperidino-2-pyridyl]carbamate The above identified compound was obtained as a white solid in the same manner as in Example 1-(1) to (5) except that morpholine was changed to piperidine.

(2) Preparation of 6-(5-ethyl-1,3,4-thiadiazol-2-ylthiomethyl)-2-[3-(2-propenyloxycarbonylamino) benzylamino]-4 -piperidinopyridine Using the compound obtained by the above reaction, the above identified compound was obtained as a white solid in the same manner as in Example 25-(3) to (5).

$^1$H-NMR(CDCl$_3$) δ: 1.37(3H, t, J=7.6 Hz), 1.49–1.67(6H, m), 3.05(2H, q, J=7.6 Hz), 3.15–3.25(4H, m), 4.40(4H, s), 4.65(2H, d, J=5.7 Hz), 5.25(1H, dd, J=1.3 Hz, 10.4 Hz), 5.35(1H, dd, J=1.3 Hz, 17.1 Hz), 5.45–5.61(1H, m), 5.53 (1H, d, J=2.1 Hz), 5.93(1H, ddt, J=5.7 Hz, 10.4 Hz, 17.1 Hz), 6.30(1H, d, J=2.1 Hz), 6.88(1H, brs), 7.05 (1H, d, J=7.8 Hz), 7.25(1H, dd, J=7.6 Hz, 7.8 Hz), 7.35(1H, s), 7.37 (1H, d, J=7.6 Hz).

EXAMPLE 50

Preparation of 6-(5-ethyl-1,3,4-thiadiazol-2-ylthiomethyl)-2-[3-(4-methyloxazol-2-ylamino) benzylamino]-4-morpholinopyridine The above identified compound was obtained as a pale yellow solid in the same manner as in Example 1-(6) and (7) except that benzyl bromide was changed to 3-[N-tert-butoxycarboyl-N-(4-methyloxazol-2-yl)amino]benzyl methanesulfonate.

$^1$H-NMR(CDCl$_3$) δ: 1.36(3H, t, J=7.6 Hz), 2.10(3H, d, J=1.3 Hz), 3.05(2H, q, J=7.6 Hz), 3.10–3.20(4H, m), 3.70–3.80(4H, m), 4.40–4.50(4H, m), 5.00–5.10(1H, m), 5.57(1H, d, J=1.9 Hz), 6.30(1H, d, J=2.0 Hz), 6.90–7.00(2H, m), 7.20–7.30(1H, m), 7.36(1H, s), 7.40–7.50(1H, m), 7.50–7.80(1H, m).

EXAMPLE 51

Preparation of 6-(5-ethyl-1,3,4-thiadiazol-2-ylthiomethyl)-4-morpholino-2-{1-[3-(2-propenyloxycarbonylamino)phenyl] ethylamino}pyridine (1) Preparation of 4-morpholino-6-(2-tetrahydropyranyl) oxymethyl-2-pyridinecarboxylic acid The compound (5.0 g) obtained in Example 1-(2) and p-toluenesulfonic acid monohydrate (3.9 g) were dissolved in chloroform (20 ml), and dihydropyran (9 g) was slowly added thereto at room temperature, followed by stirring for two hours. The reaction solution was washed sequentially with a saturated sodium hydrogen carbonate aqueous solution and a saturated sodium chloride aqueous solution. The organic layer was dried over anhydrous magnesium sulfate, and then, the solvent was distilled off under reduced pressure. The residue was dissolved in methanol (40 ml), and a 1 N sodium hydroxide aqueous solution (20 ml) was added, followed by stirring at 40° C. for one hour. The reaction solution was distilled off under reduced pressure, and chloroform and 1 N hydrochloric acid were added to the residue. The aqueous layer was extracted six times with chloroform, and the organic layers were put together and dried over anhydrous magnesium sulfate. Then, the solvent was distilled off under reduced pressure to obtain the above identified compound (3.77 g) as a white solid.

(2) Preparation of tert-butyl N-[4-morpholino-6-(2-tetrahydropyranyloxymethyl)-2-pyridyl]carbamate Using the compound obtained by the above reaction, the above identified compound was obtained as a white solid in the same manner as in Example 1-(5) except that dimethylformamide was changed to 1,4-dioxane.

(3) Preparation of 2-{N-tert-butoxycarbonyl-N-{1-[3-(2-propenyloxycarbonylamino)phenyl]ethyl}amino}-4-morpholino-6-(2-tetrahydropyranyl)oxymethylpyridine Using the compound obtained by the above reaction, the above identified compound was obtained as a pale yellow oily substance in the same manner as in Example 1-(6) and Example 8-(4) and (5), except that benzyl bromide was changed to 1-(3-nitrophenyl)ethyl methanesulfonate.

(4) Preparation of 2-{N-tert-butoxycarbonyl-N-{1-[3-(2-propenyloxycarbonylamino)phenyl]ethyl}amino}-6-hydroxymethyl-4-morpholinopyridine The compound (162 mg) obtained by the above reaction and p-toluenesulfonic acid monohydrate (55 mg) were dissolved in methanol (3 ml), followed by stirring at 60° C. for two hours. After cooling naturally, ethyl acetate was added, and the mixture was washed with a saturated sodium hydrogen carbonate aqueous solution and a saturated sodium chloride aqueous solution, and dried over anhydrous magnesium sulfate. Then, the solvent was distilled off under reduced pressure. The residue was purified by silica gel column chromatography (ethyl acetate/heptane=6/4→8/2) to obtain the above identified compound (74.3 mg) as a pale yellow solid.

(5) Preparation of 6-(5-ethyl-1,3,4-thiadiazol-2-ylthiomethyl)-4-morpholino-2-{1-[3-(2-propenyloxycarbonylamino)phenyl]ethylamino}pyridine Using the compound obtained by the above reaction, the above identified compound was obtained as a pale yellow solid in the same manner as in Example 26-(3).

$^1$H-NMR(CDCl$_3$) δ: 1.37(3H, t, J=7.6 Hz), 1.50(3H, d, J=6.7 Hz), 2.95–3.15(6H, m), 3.60–3.80(4H, m), 4.38(2H, s), 4.50–4.70(3H, m), 5.00(1H, d, J=5.02 Hz), 5.20–5.45 (3H, m), 5.85–6.05(1H, m), 6.25(1H, d, J=1.9 Hz), 6.85(1H, s), 7.00–7.10(1H, m), 7.20–7.35 (1H, m), 7.41(1H, s).

EXAMPLE 52

Preparation of 6-(5-ethyl-1,3,4-thiadiazol-2-ylthiomethyl)-4-morpholino-2-{1-[3-(2-propenyloxycarbonylamino)phenyl] propylamino}pyridine (1) Preparation of 2-{N-tert-butoxycarbonyl-N-[1-(3-nitrophenyl)propyl]amino}-4-morpholino-6-(2-tetrahydropyranyl)oxymethylpyridine Using the compound obtained in Example 51-(2), the above identified compound was obtained as a colorless oily substance in the same manner as in Example 1-(6) except that benzyl bromide was changed to 1-(3-nitrophenyl)propyl methanesulfonate.

(2) Preparation of 2-{N-[1-(3-aminophenyl)propyl]-N-tert-butoxycarbonylamino}-4-morpholino-6-(2-tetrahydropyranyl)oxymethylpyridine The compound (280 mg) obtained by the above reaction was dissolved in a solvent mixture comprising methanol (4 ml) and water (2 ml), and iron powder (250 mg) and ammonium chloride (500 mg) were added thereto, followed by refluxing for one hour. The reaction solution was subjected to celite filtration, and the filtrate was concentrated under reduced pressure. The residue was dissolved in ethyl acetate and washed with a saturated sodium hydrogen carbonate aqueous solution and a saturated sodium chloride aqueous solution and dried over anhydrous magnesium sulfate. Then, solvent was distilled off under reduced pressure, and the residue was purified by silica gel column chromatography (ethyl acetate/heptane=1/1→2/1) to obtain the above identified compound (115 mg) as a pale yellow solid.

(3) Preparation of 2-{N-tert-butoxycarbonyl-N-{1-[3-(2-propenyloxycarbonylamino)phenyl]propyl}amino}-4-morpholino-6-(2-tetrahydropyranyl)oxymethylpyridine Using the compound obtained by the above reaction, the above identified compound was obtained as a pale yellow oily substance in the same manner as in Example 8-(5).

(4) Preparation of 6-(5-ethyl-1,3,4-thiadiazol-2-ylthiomethyl)-4-morpholino-2-{1-[3-(2-propenyloxycarbonylamino)phenyl]propylamino}pyridine Using the compound obtained by the above reaction, the above identified compound was obtained as a pale yellow solid in the same manner as in Example 51-(4) and Example 26-(3).

$^1$H-NMR(CDCl$_3$) δ: 0.93(3H, t, J=7.3 Hz), 1.37(3H, t, J=7.6 Hz), 1.70–1.90(2H, m), 2.95–3.15(6H, m), 3.65–3.80 (4H, m), 4.25–4.35(1H, m), 4.38(2H, s), 4.60–4.70(2H, m), 5.05(1H, brs), 5.20–5.30(1H, m), 5.30–5.40(1H, m), 5.41 (1H, d, J=1.9 Hz), 5.85–6.05 (1H, m), 6.23(1H, d, J=1.9 Hz), 6.83(1H, s), 7.00–7.10(1H, m), 7.20–7.30(2H, m), 7.39(1H, s).

EXAMPLE 53

Preparation of 6-(5-ethyl-1,3,4-thiadiazol-2-ylthiomethyl)-2-[2-methyl-3-(2-propenyloxycarbonylamino)benzylamino]-4-morpholinopyridine The above identified compound was obtained as a pale yellow oily substance in the same manner as in Example 1-(6), Example 25-(4), Example 8-(5) and Example 1-(7) except that benzyl bromide was changed to 2-methyl-3-nitrobenzyl methanesulfonate.

$^1$H-NMR(CDCl$_3$) δ: 1.37(3H, t, J=7.6 Hz), 2.24(3H, s), 3.06(2H, q, J=7.6 Hz), 3.19 (4H, dd, J=4.7 Hz, 5.0 Hz), 3.78 (4H, dd, J=4.7 Hz, 5.0 Hz), 4.41(2H, m), 4.42(2H, s), 4.67(2H, d, J=5.7 Hz), 4.70–4.87 (1H, m), 5.27(1H, dd, J=1.3 Hz, 10.4 Hz), 5.35(1H, dd, J=1.3 Hz, 17.2 Hz), 5.57(1H, d, J=1.9 Hz), 5.98(1H, ddt, J=5.7 Hz, 10.4 Hz, 17.2 Hz), 6.33(1H, d, J=1.9 Hz), 6.42–6.52(1H, m), 7.13–7.20 (2H, m), 7.62(1H, m).

EXAMPLE 54

Preparation of 6-(5-ethyl-1,3,4-thiadiazol-2-ylthiomethyl)-2-[3-methoxy-5-(2-propenyloxycarbonylamino)benzylamino]-4-morpholinopyridine The above identified compound was obtained as a pale yellow oily substance in the same manner as in Example 8-(3) to (6) and Example 26-(3) except that 3-nitrobenzyl chloride was changed to 3-methoxy-5-nitrobenzyl bromide.

$^1$H-NMR(CDCl$_3$) δ: 1.37(3H, t, J=7.6 Hz), 3.06(2H, q, J=7.6 Hz), 3.16(4H, t, J=5.0 Hz), 3.77(4H, t, J=5.0 Hz), 3.78(3H, s), 4.38(2H, d, J=5.9 Hz), 4.38(2H, d, J=5.6 Hz), 4.41(2H, s), 4.88(1H, s), 5.26 (1H, dd, J=1.3 Hz, 10.5 Hz), 5.36(1H, dd, J=1.3 Hz, 17.2 Hz), 5.56(1H, d, J=2.0 Hz), 5.95(1H, ddt, J=5.6 Hz, 10.5 Hz, 17. 2Hz), 6.31 (1H, d, J=2.0 Hz), 6.38(1H, s), 6.62(1H, s), 6.89(1H, s), 7.05(1H, s).

EXAMPLE 55

Preparation of 6-(5-ethyl-1,3,4-thiadiazol-2-ylthiomethyl)-2-[2-fluoro-5-(2-propenyloxycarbonylamino)benzylamino]-4-morpholinopyridine The above identified compound was obtained as a pale yellow oily substance in the same manner as in Example 54 except that 3-methoxy-5-nitrobenzyl bromide was changed to 2-fluoro-5-nitrobenzyl bromide.

$^1$H-NMR(CDCl$_3$) δ: 1.37(3H, t, J=7.6 Hz), 3.06(2H, q, J=7.6 Hz), 3.17(4H, t, J=5.0 Hz), 3.77(4H, t, J=5.0 Hz), 4.40(2H, s), 4.49(2H, d, J=6.3 Hz), 4.64(2H, d, J=5.5 Hz), 4.92(1H, brt, J=6.3 Hz), 5.25 (1H, d, J=10.1 Hz), 5.34(1H, d, J=17.1 Hz), 5.59(1H, d, J=1.9 Hz), 5.94(1H, ddt, J=5.5 Hz, 10.1 Hz, 17.1 Hz), 6.29(1H, d, J=1.9 Hz), 6.98 (1H, m), 6.99(1H, brs), 7.30(1H, dd, J=2.5 Hz, 6.2 Hz), 7.41(1H, brs).

EXAMPLE 56

Preparation of 6-(5-ethyl-1,3,4-thiadiazol-2-ylthiomethyl)-2-[4-fluoro-3-(2-propenyloxycarbonylamino)benzylamino]-4-morpholinopyridine The above identified compound was obtained as a pale yellow solid in the same manner as in Example 52 except that 1-(3-nitrophenyl)propyl bromide was changed to 4-fluoro-3-nitrobenzyl bromide.

$^1$H-NMR(CDCl$_3$) δ: 1.36(3H, t, J=7.6 Hz), 3.06(2H, q, J=7.6 Hz), 3.17(4H, t, J=5.0 Hz), 3.77(4H, t, J=5.0 Hz), 4.40(2H, d, J=5.2 Hz), 4.41(2H, s), 4.68(2H, d, J=5.4 Hz), 4.87(1H, brt, J=5.2 Hz), 5.28 (1H, d, J=10.0 Hz), 5.37(1H, d, J=17.1 Hz), 5.58(1H, d, J=1.9 Hz), 5.97(1H, ddt, J=5.4 Hz, 10.0 Hz, 17.1 Hz), 6.31(1H, d, J=1.9 Hz), 6.84–6.90(1H, m), 7.00–7.03(2H, m), 8.09(1H, m).

EXAMPLE 57

Preparation of 2-[2-chloro-5-(2-propenyloxycarbonylamino)benzylamino]-6-(5-ethyl-1,3,4-thiadiazol-2-ylthiomethyl)-4-morpholinopyridine The above identified compound was obtained as a pale yellow oily substance in the same manner as in Example 1-(6), Example 52-(2), Example 8-(5) and Example 1-(7) except that benzyl bromide was changed to 2-chloro-5-nitrobenzyl methanesulfonate.

$^1$H-NMR(CDCl$_3$) δ: 1.37(3H, t, J=7.6 Hz), 3.06(2H, q, J=7.6 Hz), 3.16(4H, t, J=5.0 Hz), 3.77(4H, t, J=5.0 Hz), 4.40(2H, s), 4.52(2H, d, J=6.4 Hz), 4.64(2H, d, J=5.6 Hz), 4.96(1H, brt, J=6.4 Hz), 5.74 (1H, d, J=10.4 Hz), 5.34(1H, d, J=17.1 Hz), 5.55(1H, d, J=1.9 Hz), 5.94(1H, ddt, J=5.6 Hz, 10.4 Hz, 17.1 Hz), 6.28(1H, d, J=1.9 Hz), 7.14 (1H, brs), 7.27–7.31(2H, m), 7.49–7.53(1H, m).

EXAMPLE 58

Preparation of 2-[4-chloro-3-(2-propenyloxycarbonylamino)benzylamino]-6-(5-ethyl-1,3,4-thiadiazol-2-ylthiomethyl)-4-morpholinopyridine (1) Preparation of 2-[N-tert-butoxycarbonyl-N-(3-amino-4-chlorobenzyl)amino]-4-morpholino-6-(2-tetrahydropyranyl)oxymethylpyridine The above identified compound was obtained as a pale yellow oily substance in the same manner as in Example 52-(1) and (2) except that 1-(3-nitrophenyl)propyl bromide was changed to 4-chloro-3-nitrobenzyl chloride.

(2) Preparation of 2-[N-tert-butoxycarbonyl-N-(4-chloro-3-acetamidobenzyl)amino]-4-morpholino-6-(2-tetrahydropyranyl)oxymethylpyridine The compound (92 mg) obtained by the above reaction was dissolved in pyridine (2 ml), and acetic anhydride (1 ml) was added, followed by stirring at room temperature for 30 minutes. Ethyl acetate was added thereto, and the mixture was washed with a saturated sodium hydrogen carbonate aqueous solution, water and a saturated sodium chloride aqueous solution and dried over anhydrous sodium sulfate. Then, the solvent was distilled off under reduced pressure to obtain the above identified compound (92 mg) as a pale yellow solid.

(3) Preparation of 2-[N-tert-butoxycarbonyl-N-{4-chloro-3-[N'-acetyl-N'-(2-propenyloxycarbonyl)amino]benzyl}amino]-4-morpholino-6-(2-tetrahydropyranyl)oxymethylpyridine The compound (92 mg) obtained by the above reaction was dissolved in dimethylformamide (1 ml), and mixed with a solution of sodium hydride (9.6 mg) in dimethylformamide (0.5 ml), at 0° C., followed by stirring at the same temperature for one hour. Allyl chloroformate (50.9 μl) was added thereto, followed by stirring at the same temperature for one hour and further at room temperature for one hour. The reaction was added to water, followed by extraction with ethyl acetate. The organic layer was washed with water, a saturated sodium hydrogen carbonate aqueous solution and a saturated sodium chloride aqueous solution and dried over anhydrous sodium sulfate. Then, the solvent was distilled off under reduced pressure. The residue was purified by silica gel column chromatography (ethyl acetate/heptane=1/2) to obtain the above identified compound (45 mg) as an oily substance.

(4) Preparation of 2-{N-tert-butoxycarbonyl-N-[4-chloro-3-(2-propenyloxycarbonylamino)benzyl]amino}-4-morpholino-6-(2-tetrahydropyranyl)oxymethylpyridine The compound (45 mg) obtained by the above reaction was dissolved in ethanol (5 ml), and hydrazine monohydrate (17 μl) was added thereto, followed by stirring at room temperature for 0.5 hour. The solvent was distilled off under reduced pressure, and the residue was purified by silica gel column chromatography (ethyl acetate/heptane=1/1) to obtain the above identified compound (35 mg) as a pale yellow oily substance.

(5) Preparation of 2-[4-chloro-3-(2-propenyloxycarbonylamino)benzylamino]-6-(5-ethyl-1,3,4-thiadiazol-2-ylthiomethyl)-4-morpholinopyridine Using the compound obtained by the above reaction, the above identified compound was obtained as a pale yellow solid in the same manner as in Example 51-(4) and (5).

$^1$H-NMR(CDCl$_3$) δ: 1.37(3H, t, J=7.6 Hz), 3.05(2H, q, J=7.6 Hz), 3.17(4H, t, J=5.0 Hz), 3.77(4H, t, J=5.0 Hz), 4.41(2H, s), 4.43(2H, d, J=5.5 Hz), 4.68(2H, d, J=5.4 Hz), 4.92(1H, brt, J=5.5 Hz), 5.29 (1H, d, J=10.0 Hz), 5.39(1H, d, J=17.1 Hz), 5.58(1H, d, J=1.9 Hz), 5.98(1H, ddt, J=5.4 Hz, 10.0 Hz, 17.1 Hz), 6.30(1H, d, J=1.9 Hz), 7.04 (1H, dd, J=1.8 Hz, 8.2 Hz), 7.18(1H, brs), 7.29(1H, d, J=8.2 Hz), 8.18 (1H, d, J=1.8 Hz).

EXAMPLE 59

Preparation of 2-[3-amino-5-(2-propenyloxycarbonylamino)benzylamino]-6-(5-ethyl-1,3,4-thiadiazol-2-ylthiomethyl)-4-morpholinopyridine (1) Preparation of 2-{N-tert-butoxycarbonyl-N-[3,5-bis(2-propenyloxycarbonylamino)benzyl]amino}-6-hydroxymethyl-4-morpholinopyridine The above identified compound was obtained as a pale yellow oily substance in the same manner as in Example 51-(3) and (4) except that 1-(3-nitrophenyl)ethyl methanesulfonate was changed to 1-bromomethyl-3,5-dinitrobenzene.

(2) Preparation of 2-{N-tert-butoxycarbonyl-N-[3,5-bis(2-propenyloxycarbonylamino)benzyl]amino}-6-(5-ethyl-1,3,4-thiadiazol-2-ylthiomethyl)-4-morpholinopyridine Using the compound obtained by the above reaction, the above identified compound was obtained as a pale yellow oily substance in the same manner as in Example 8-(7) except that 5-ethyl-3-mercapto-1,2,4-triazole was changed to 5-ethyl-2-mercapto-1,3,4-thiadiazole.

(3) Preparation of 2-[3-amino-5-(2-propenyloxycarbonylamino)benzylamino]-6-(5-ethyl-1,3,4-thiadiazol-2-ylthiomethyl)-4-morpholinopyridine Using the compound obtained by the above reaction, the above identified compound was obtained as a pale yellow solid in the same manner as in Example 36-(2) and Example 1-(7).

$^1$H-NMR(CDCl$_3$) δ: 1.37(3H, t, J=7.6 Hz), 3.06(2H, q, J=7.6 Hz), 3.16(4H, t, J=5.0 Hz), 3.70(2H, brs), 3.76(4H, t, J=5.0 Hz), 4.30 (2H, d, J=6.0 Hz), 4.41(2H, s), 4.63(2H, d, J=5.6 Hz), 4.84(1H, brt, J=6.0 Hz), 5.25(1H, d, J=10.6 Hz), 5.35(1H, d, J=17.1 Hz), 5.55(1H, d, J=1.9 Hz), 5.95(1H, ddt, J=5.6 Hz, 10.6 Hz, 17.1 Hz), 6.30(1H, d, J=1.9 Hz), 6.39 (1H, brs), 6.61(1H, brs), 6.68(1H, brs), 6.83(1H, brs).

Examples 60 and 61 were obtained in the same manner as in Example 57 except that 2-chloro-5-nitrobenzyl methanesulfonate was changed to the corresponding nitrobenzyl bromide.

EXAMPLE 60

6-(5-ethyl-1,3,4-thiadiazol-2-ylthiomethyl)-2-[3-fluoro-5-(2-propenyloxycarbonylamino)benzylamino]-4-morpholinopyridine $^1$H-NMR(CDCl$_3$) δ: 1.37(3H, t, J=7.6 Hz), 3.06(2H, q, J=7.6 Hz), 3.15(4H, dd, J=4.9 Hz, J=5.0 Hz), 3.76(4H, dd, J=4.7 Hz, J=5.1 Hz), 4.40(2H, s), 4.42(2H, d, J=6.3 Hz), 4.65(2H, d, J=5.6 Hz), 4.85–4.95(1H, brs), 5.26(1H, dd, J=1.2 Hz, 10.5 Hz), 5.35(1H, dd, J=1.2 Hz, 16.9 Hz), 5.53(1H, s), 5.90–6.00(1H, m), 6.31(1H, s), 6.75 (1H, d, J=8.72 Hz), 6.98–7.02(2H, m), 7.28(1H, brs).

EXAMPLE 61

6-(5-ethyl-1,3,4-thiadiazol-2-ylthiomethyl)-4-morpholino-2-[3-(2-propenyloxycarbonylamino)-5-trifluoromethylbenzylamino]pyridine $^1$H-NMR(CDCl$_3$) δ: 1.37(3H, t, J=7.58 Hz), 3.06(2H, q, J=7.6 Hz), 3.10–3.20(4H, m), 3.68–3.80(4H, m), 4.40(2H, s), 4.50(2H, d, J=5.75 Hz), 4.60–4.70(2H, m), 4.80–4.98 (1H, m), 5.20–5.40 (2H, m), 5.55(1H, d, J=1.92 Hz), 5.85–6.05(1H, m), 6.31(1H, d, J=1.9 Hz), 7.16(1H, s), 7.30(1H, s), 7.52(1H, s), 7.74(1H, s).

EXAMPLE 62

Preparation of 2-[3-dimethylamino-5-(2-propenyloxycarbonylamino)benzylamino]-6-(5-ethyl-1,3,4-thiadiazol-2-ylthiomethyl)-4-morpholinopyridine The above identified compound was obtained as a pale yellow solid in the same manner as in Example 58 except that 4-chloro-3-nitrobenzyl chloride was changed to 3-dimethylamino-5-nitrobenzyl bromide.

$^1$H-NMR(CDCl$_3$) δ: 1.37(3H, t, J=7.6 Hz), 2.93(6H, s), 3.07(2H, q, J=7.6 Hz), 3.17(4H, t, J=4.9 Hz), 3.77(4H, t, J=4.9 Hz), 4.34(2H, d, J=5.6 Hz), 4.41 (2H, s), 4.64(2H, dd, J=1.4 Hz, 5.6 Hz), 4.90(1H, brs), 5.25(1H, dd, J=1.4 Hz, 10.4 Hz), 5.35(1H, dd, J=1.4 Hz, 17.2 Hz), 5.60(1H, d, J=2.0 Hz), 5.95(1H, ddt, J=5.6 Hz, 10.4 Hz, 17.2 Hz), 6.30 (1H, d, J=2.0 Hz), 6.44(1H, s), 6.64(1H, s), 6.66(1H, s), 6.82(1H, brs).

EXAMPLE 63

Preparation of 6-(5-ethyl-1,3-thiazol-2-ylthiomethyl)-2-[3-methoxy-5-(2-propenyloxycarbonylamino)benzylamino]-4-morpholinopyridine The above identified compound was obtained as a pale yellow solid in the same manner as in Example 54 except that 5-ethyl-2-mercapto-1,3,4-thiadiazole was changed to 5-ethyl-2-mercapto-1,3-thiazole.

$^1$H-NMR(CDCl$_3$) δ: 1.26(3H, t, J=7.5 Hz), 2.77(2H, q, J=7.5 Hz), 3.14(4H, dd, J=4.8 Hz, J=4.9 Hz), 3.76(4H, dd, J=4.0 Hz, J=4.8 Hz), 3.78(3H, s), 4.26(2H, s), 4.37(2H, d, J=5.9 Hz), 4.65(2H, d, J=5.8 Hz), 5.10(1H, brs), 5.25(1H, dd, J=1.4 Hz, 10.4 Hz), 5.35(1H, dd, J=1.4 Hz, 17.2 Hz), 5.55(1H, s), 5.90–6.00(1H, m), 6.22(1H, s), 6.62 (1H, s), 6.67(1H, s), 6.88(1H, s), 7.05(1H, s), 7.33(1H, s).

EXAMPLE 64

Preparation of 2-[5-chloro-3-(2-propenyloxycarbonylamino)benzylamino]-6-(5-ethyl-1,3,4-thiadiazol-2-ylthiomethyl)-4-morpholinopyridine (1) Preparation of 2-{N-tert-butoxycarbonyl-N-[3-chloro-5-(2-propenyloxycarbonylamino)benzyl]amino}-4-morpholino- 6-(2-tetrahydropyranyl)oxymethylpyridine Using the compound obtained in Example 51-(2), the above identified compound was obtained as a pale yellow oily substance in the same manner as in Example 1-(6) and Example 4-(2) and (3) except that benzyl bromide was changed to 3-chloro-5-methoxycarbonylbenzyl methanesulfonate.

(2) Preparation of 2-[5-chloro-3-(2-propenyloxycarbonylamino)benzylamino]-6-(5-ethyl-1,3,4-thiadiazol-2-ylthiomethyl)-4-morpholinopyridine Using the compound obtained by the above reaction, the above identified compound was obtained as a pale yellow solid in the same manner as in Example 51-(4) and (5).

$^1$H-NMR(CDCl$_3$) δ: 1.37(3H, t, J=7.5 Hz), 3.05(2H, q, J=7.5 Hz), 3.16(4H, dd, J=4.9 Hz, J=5.0 Hz), 3.76(4H, dd, J=4.6 Hz, J=4.7 Hz), 4.40(2H, s), 4.41(2H, d, J=6.7 Hz), 4.65(2H, d, J=5.7 Hz), 5.00(1H, brs), 5.26(1H, dd, J=1.4 Hz, 10.4 Hz), 5.35(1H, dd, J=1.4 Hz, 17.1 Hz), 5.53(1H, s), 5.85–6.00 (1H, m), 6.32(1H, s), 6.95(1H, s), 7.04(1H, s), 7.19(1H, s), 7.48(1H, s).

EXAMPLE 65

Preparation of 6-[2-(5-ethyl-1,3,4-thiadiazol-2-yl)propyl]-4-morpholino-2-[3-(2-propenyloxycarbonylamino)benzylamino]pyridine The above identified compound was obtained in the same manner as in Example 22 except that methyl dimethylphosphonoacetate in Example 22-(3) was changed to ethyl diethylphosphonopropionate.

$^1$H-NMR(CDCl$_3$) δ: 1.37(3H, t, J=7.6 Hz), 1.44(3H, t, J=7.0 Hz), 2.90(1H, dd, J=7.0 Hz, 13.8 Hz), 3.06(2H, q, J=7.6 Hz), 3.00–3.06 (1H, m), 3.15(4H, t, J=5.0 Hz), 3.75 (4H, t, J=5.0 Hz), 3.80–3.94 (1H, m), 4.37(1H, dd, J=5.8 Hz, 15.5 Hz), 4.46(1H, dd, J=6.0 Hz, 15.5 Hz), 4.64(2H, d, J=5.6 Hz), 5.24(1H, dd, J=1.4 Hz, 10.4 Hz), 5.34 (1H, dd, J=1.4 Hz, 17.2 Hz), 5.48(1H, d, J=2.2 Hz), 5.87–6.00(1H, m), 5.96(1H, d, J=2.2 Hz), 7.01(1H, d, J=7.7 Hz), 7.25(1H, t, J=7.7 Hz), 7.33(1H, s), 7.38(1H, s), 7.39(1H, d, J=7.7 Hz).

EXAMPLE 66

Preparation of 6-(5-ethyl-4-methyl-1,3-thiazol-2-ylthiomethyl)-4-morpholino-2-[3-(2-propenyloxycarbonylamino)benzylamino]pyridine (1) Preparation of 2-(N-tert-butoxycarbonyl-N-3-nitrobenzyl)amino-4-morpholino-6-(2-tetrahydropyranyl)oxymethylpyridine Tert-butyl N-[4-morpholino-6-(2-tetrahydropyranyloxymethyl)-2-pyridyl]carbamate (1.38 g) obtained in Example 51-(2), was dissolved in dimethylformamide (20 ml), and 60% sodium hydride (154 mg) was added thereto under cooling with ice, followed by stirring at the same temperature for 30 minutes and at room temperature for 30 minutes. The reaction solution was cooled with ice, and a solution of 3-nitrobenzyl chloride (662 mg) in dimethylformamide (5 ml), was added thereto, followed by stirring at the same temperature for 10 minutes and at room temperature for 3 hours. Water (100 ml) was added to the reaction solution, followed by extraction with ethyl acetate (100 ml+50 ml). The organic layers were put together and washed with a saturated sodium chloride aqueous solution (50 ml) and then dried over anhydrous magnesium sulfate. Then, the solvent was distilled off under reduced pressure. The residue was purified by silica gel column chromatography (heptane/ethyl acetate=1:1) to obtain the above identified compound (1.71 g) as a pale yellow oily substance.

(2) Preparation of 2-(N-3-aminobenzyl-N-tert-butoxycarbonyl)amino-4-morpholino-6-(2-tetrahydropyranyl)oxymethylpyridine 2-(N-tert-butoxycarbonyl-N-3-nitrobenzyl)amino-4-morpholino-6-(2-tetrahydropyranyl)oxymethylpyridine (1.71 g) was dissolved in methanol (30 ml), and 5% palladium-carbon (0.1 g) was added thereto, followed by vigorous stirring in a hydrogen (normal pressure) atmosphere at room temperature for two hours. The catalyst was filtered off, followed by washing with chloroform. The filtrate and washing liquid were put together and concentrated under reduced pressure to obtain the above identified compound (1.62 g) as a pale yellow solid.

(3) Preparation of 2-[N-tert-butoxycarbonyl-N-3-(2-propenyloxycarbonylamino)benzyl]amino-4-morpholino-6-(2-tetrahydropyranyl)oxymethylpyridine To a solution of 2-(N-3-aminobenzyl-N-tert-butoxycarbonyl)amino- 4-morpholino-6-(2-tetrahydropyranyl)oxymethylpyridine (1.61 g) and 4-dimethylaminopyridine (472 mg) in chloroform (15 ml), allyl chloroformate (0.41 ml) was added under cooling with ice, followed by stirring at the same temperature for 30 minutes and at room temperature for two hours. The reaction solution was diluted with chloroform (100 ml), and washed with 50 ml each of water, a saturated sodium hydrogen carbonate aqueous solution and a saturated sodium chloride aqueous solution and then dried over anhydrous magnesium sulfate. Then, the solvent was distilled off under reduced pressure. The residue was purified by silica gel column chromatography (ethyl acetate/heptane=1/1) to obtain the above identified compound (1.65 g) as a white amorphous solid.

(4) Preparation of 2-[N-tert-butoxycarbonyl-3-(2-propenyloxycarbonylamino)benzylamino]-6-hydroxymethyl-4-morpholinopyridine 2-[N-tert-butoxycarbonyl-N-3-(2-propenyloxycarbonylamino)benzyl]amino-4-morpholino-6-(2-tetrahydropyranyl)oxymethylpyridine (1.10 g) was dissolved in ethanol (15 ml), and p-toluenesulfonic acid monohydrate (0.43 g) was added thereto, followed by stirring at 60° C. for two hours. After cooling naturally, the reaction solution was diluted with ethyl acetate (100 ml) and washed with a saturated sodium hydrogen carbonate aqueous solution and a saturated sodium chloride aqueous solution and then dried over anhydrous magnesium sulfate. The solvent was distilled off under reduced pressure, and the residue was purified by silica gel column chromatography (ethyl acetate/heptane=2/1) to obtain the above identified compound (0.82 g) as a white amorphous solid.

(5) Preparation of 2-[N-tert-butoxycarbonyl-N-3-(2-propenyloxycarbonylamino)benzylamino]-6-methylsulfonyloxymethyl-4-morpholinopyridine To a solution of 2-[N-tert-butoxycarbonyl-N-3-(2-propenyloxycarbonylamino)benzylamino]-6-hydroxymethyl-4-morpholinopyridine (0.82 g) and triethylamine (0.46 ml) in ethyl acetate (10 ml), methanesulfonyl chloride (0.19 ml) was added under cooling with ice, followed by stirring at the same temperature for 10 minutes and at room temperature for 30 minutes. The reaction solution was diluted with ethyl acetate (30 ml), sequentially washed with 30 ml each of water, a saturated sodium hydrogen carbonate aqueous solution and a saturated sodium chloride aqueous solution and dried over anhydrous magnesium sulfate. The solvent was distilled off under reduced pressure to obtain the above identified compound (0.96 g) as a white amorphous solid.

(6) Preparation of 6-(5-ethyl-4-methyl-1,3-thiazol-2-ylthiomethyl)-4-morpholino-2-[3-(2-propenyloxycarbonylamino)benzylamino]pyridine 2-[N-tert-butoxycarbonyl-N-3-(2-propenyloxycarbonylamino)benzylamino]-6-methylsulfonyloxymethyl-4-morpholinopyridine (260 mg) was dissolved in dimethylformamide (10 ml), and potassium carbonate (124 mg) and 5-ethyl-2-mercapto-4-methyl-1,3-thiazole (80 mg) were added thereto, followed by stirring at room temperature for 3 hours. To the reaction solution, ethyl acetate was added, and the mixture was washed sequentially with water and a saturated sodium chloride aqueous solution and then dried over anhydrous magnesium sulfate. The solvent was distilled off under reduced pressure. The residue was dissolved in methylene chloride (10 ml), and trifluoroacetic acid (5 ml) was added under cooling with ice, followed by stirring at room temperature overnight. The reaction solution was concentrated under reduced pressure, and the residue was dissolved in ethyl acetate, washed with a saturated sodium hydrogen carbonate aqueous solution and a saturated sodium chloride aqueous solution and then dried over anhydrous sodium sulfate. The solvent was distilled off under reduced pressure, and the residue was purified by silica gel column chromatography (chloroform/methanol= 40/1→10/1) to obtain the above identified compound (234 mg) as a pale yellow oily substance.

$^1$H-NMR(CDCl$_3$) δ: 1.20(3H, t, J=7.6 Hz), 2.29(3H, s), 2.68(2H, q, J=7.6 Hz), 3.14(4H, t, J=5.0 Hz), 3.76(4H, t, J=4.7 Hz), 4.23(2H, s), 4.42(2H, d, J=5.9 Hz), 4.66(2H, d, J=5.8 Hz), 4.90(1H, brs), 5.26(1H, d, J=10.4 Hz), 5.35(1H, d, J=17.2 Hz), 5.56(1H, d, J=1.9 Hz),5.90–6.00(1H, m), 6.24(1H, d, J=2.0 Hz), 6.74(1H, brs), 7.06(1H, d, J=7.6 Hz), 7.20–7.40(3H, m).

Compounds of Examples 67 to 99 were obtained in the same manner as in Example 66 except that the material used in Example 66 was changed to the materials corresponding to the respective desired compounds.

EXAMPLE 67

6-(4-ethyl-1,3-thiazol-2-ylthiomethyl)-4-morpholino-2-[3-(2-propenyloxycarbonylamino)benzylamino]pyridine $^1$H-NMR(CDCl$_3$) δ: 1.27(3H, t, J=7.4 Hz), 2.75(2H, q, J=7.5 Hz), 3.14(4H, t, J=4.9 Hz), 3.76(4H, t, J=4.7 Hz), 4.28(2H, s), 4.41(2H, d, J=5.9 Hz), 4.65(2H, d, J=5.7 Hz), 4.91(1H, brs), 5.26(1H, d, J=10.3 Hz), 5.35(1H, d, J=18.8 Hz), 5.56(1H, d, J=2.0 Hz), 5.90–6.00 (1H, m), 6.26(1H, d, J=1.9 Hz), 6.74(1H, brs), 7.05(1H, d, J=7.3 Hz), 7.20–7.40 (4H, m).

EXAMPLE 68

6-(5-isopropyl-1,3-thiazol-2-ylthiomethyl)-4-morpholino-2-[3-(2-propenyloxycarbonylamino)benzylamino]pyridine $^1$H-NMR(CDCl$_3$) δ: 1.29(6H, d, J=7.0 Hz), 3.13(5H, t, J=5.0 Hz), 3.75(4H, t, J=5.0 Hz), 4.27(2H, s), 4.42(2H, d, J=5.9 Hz), 4.65(2H, d, J=5.5 Hz), 4.88(1H, t, J=5.9 Hz), 5.25 (1 H, d, J=10.7 Hz), 5.35 (1H, d, J=17.1 Hz), 5.55(1H, d, J=1.9 Hz), 5.96(1H, ddt, J=5.5 Hz, 10.7 Hz, 17.1 Hz), 6.21(1H, d, J=1.9 Hz), 6.81(1H, brs), 7.05(1H, d, J=7.8 Hz), 7.33–7.38(4H, m).

EXAMPLE 69

6-(2-cyclohexeno[d]thiazolylthiomethyl)-4-morpholino-2-[3-(2-propenyloxycarbonylamino)benzylamino]pyridine $^1$H-NMR(CDCl$_3$) δ: 1.75–1.90(4H, brs), 2.60–2.80(4H, brs), 3.15(4H, t, J=5.0 Hz), 3.76(4H, t, J=4.7 Hz), 4.24(2H, s), 4.41(2H, d, J=5.6 Hz), 4.65(2H, d, J=5.6 Hz), 4.97(1H, brs), 5.25(1H, d, J=10.3 Hz), 5.35(1H, d, J=17.1 Hz), 5.55(1H, d, J=1.9 Hz), 5.90–6.00 (1H, m), 6.25(1H, d, J=2.0 Hz), 6.76(1H, brs), 7.05(1H, d, J=7.2 Hz), 7.20–7.40(3H, m).

EXAMPLE 70

6-(2-cyclopenteno[d]thiazolylthiomethyl)-4-morpholino-2-[3-(2-propenyloxycarbonylamino)benzylamino]pyridine $^1$H-NMR(CDCl$_3$) δ: 2.40–2.50(2H, m), 2.75–2.90(4H, m), 3.14 (4H, t, J=5.1 Hz), 3.76(4H, t, J=4.8 Hz), 4.25(2H, s), 4.41(2H, d, J=5.6 Hz), 4.65(2H, d, J=5.7 Hz), 4.97(1H, brs), 5.25(1H, d, J=10.2 Hz), 5.35(1H, d, J=17.1 Hz), 5.55(1H, d, J=2.0 Hz), 5.90–6.00 (1H, m), 6.22(1H, d, J=2.0 Hz), 6.79(1H, brs), 7.05(1H, d, J=7.3 Hz), 7.20–7.40 (3H, m).

EXAMPLE 71

6-(4-methyl-5-propyl-1,3-thiazol-2-ylthiomethyl)-4-morpholino-2-[3-(2-propenyloxycarbonylamino)benzylamino]pyridine $^1$H-NMR(CDCl$_3$) δ: 0.94(3H, t, J=7.3 Hz), 1.58(2H, m), 2.29 (3H, s), 2.62(2H, t, J=7.3 Hz), 3.14(4H, t, J=5.0 Hz), 3.76(4H, t, J=4.7 Hz), 4.23(2H, s), 4.41(2H, d, J=5.6 Hz), 4.65(2H, d, J=5.3 Hz), 5.00(1H, brs), 5.26(1H, d, J=10.2 Hz), 5.35(1H, d, J=17.2 Hz), 5.55 (1H, d, J=1.7 Hz), 5.90–6.00(1H, m), 6.24(1H, d, J=1.7 Hz), 6.76 (1H, brs), 7.06(1H, d, J=7.2 Hz), 7.20–7.40(3H, m).

EXAMPLE 72

6-(4-methyl-1,3-thiazol-2-ylthiomethyl)-4-morpholino-2 -[3-(2-propenyloxycarbonylamino)benzylamino]pyridine $^1$H-NMR(CDCl$_3$) δ: 2.40(3H, s), 3.15(4H, t, J=5.0 Hz), 3.76(4H, t, J=5.0 Hz), 4.28(2H, s), 4.41(2H, d, J=5.9 Hz), 4.65(2H, d, J=5.7 Hz), 4.85(1H, brs), 5.25(1H, d, J=10.4 Hz), 5.35(1H, d, J=17.3 Hz), 5.56(1H, d, J=1.9 Hz), 5.90–6.00(1H, m), 6.26(1H, d, J=1.9 Hz), 6.74(1H, s), 6.76(1H, brs), 7.05(1H, d, J=7.3 Hz), 7.20–7.40 (3H, m).

EXAMPLE 73

6-(4,5-diethyl-1,3-thiazol-2-ylthiomethyl)-4-morpholino- 2-[3-(2-propenyloxycarbonylamino)benzylamino]pyridine $^1$H-NMR(CDCl$_3$) δ: 1.15–1.30(6H, m), 2.60(4H, m), 3.14 (4H, t, J=5.0 Hz), 3.73(4H, t, J=5.0 Hz), 4.23(2H, s), 4.42(2H, d, J=4.4 Hz), 4.65(2H, d, J=5.7 Hz), 5.05(1H, brs), 5.25(1H, d, J=10.4 Hz), 5.35(1H, d, J=17.2 Hz), 5.55(1H, d, J=2.0 Hz), 5.90–6.00(1H, m), 6.23(1H, d, J=2.0 Hz), 6.70 (1H, brs), 7.00–7.40(4H, m).

EXAMPLE 74

6-(4-hydroxymethyl-1,3-thiazol-2-ylthiomethyl)-4-morpholino-2-[3-(2-propenyloxycarbonylamino)benzylamino]pyridine $^1$H-NMR(CDCl$_3$) δ: 3.16(4H, t, J=5.0 Hz), 3.70(1H, s), 3.76(4H, t, J=5.0 Hz), 4.29(2H, s), 4.41(2H, d, J=5.6 Hz), 4.66(2H, td, J=1.4 Hz, 5.7 Hz), 4.70(2H, s), 5.25(1H, qd, J=1.4 Hz, 10.4 Hz), 5.35(1H, qd, J=1.4 Hz, 17.0 Hz), 5.54(1H, d, J=2.0 Hz), 5.95(1H, ddt, J=5.7 Hz, 10.4 Hz, 17.0 Hz), 6.26(1H, d, J=2.0 Hz), 6.95(1H, s), 7.15(1H, d, J=7.0 Hz), 7.20–7.30(2H, m), 7.35(2H, s).

EXAMPLE 75

6-(4-ethyl-1,3-oxazol-2-ylthiomethyl)-4-morpholino-2-[3 -(2-propenyloxycarbonylamino)benzylamino]pyridine $^1$H-NMR(CDCl$_3$) δ: 1.20(3H, t, J=7.5 Hz), 2.51(2H, q, J=7.6 Hz), 3.15(4H, t, J=4.9 Hz), 3.76(4H, t, J=4.6 Hz), 4.27(2H, s), 4.41(2H, d, J=5.6 Hz), 4.65(2H, d, J=5.6 Hz), 4.90(1H, brs), 5.25(1H, d, J=10.3 Hz), 5.35(1H, d, J=17.1 Hz), 5.55(1H, d, J=1.9 Hz), 5.90–6.00 (1H, m), 6.26(1H, d, J=1.7 Hz), 6.82(1H, brs), 7.05(1H, d, J=7.3 Hz), 7.20–7.40 (4H, m).

EXAMPLE 76

6-(5-ethyl-1,3-oxazol-2-ylthiomethyl)-4-morpholino-2-[3-(2-propenyloxycarbonylamino)benzylamino]pyridine $^1$H-NMR(CDCl$_3$) δ: 1.21(3H, t, J=7.6 Hz), 2.63(2H, q, J=6.7 Hz), 3.15(4H, t, J=4.9 Hz), 3.76(4H, t, J=5.0 Hz), 4.25(2H, s), 4.41(2H, d, J=5.6 Hz), 4.65(2H, d, J=5.6 Hz), 5.00–5.10(1H, brs), 5.25(1H, d, J=10.6 Hz), 5.35(1H, d, J=17.1 Hz), 5.55(1H, d, J=1.9 Hz), 5.90–6.00(1H, m), 6.24(1H, d, J=1.9 Hz), 6.69(1H, s), 6.90(1H, brs), 7.04(1H, d, J=7.6 Hz), 7.20–7.40(3H, m).

EXAMPLE 77

6-(5-ethyl-4-methyl-1,3-oxazol-2-ylthiomethyl)-4-morpholino-2-[3-(2-propenyloxycarbonylamino)benzylamino]pyridine $^1$H-NMR(CDCl$_3$) δ: 1.17(3H, t, J=7.5 Hz), 2.05(3H, s), 2.50–2.60(2H, m), 3.15(4H, t, J=5.1 Hz), 3.76(4H, t, J=4.9 Hz), 4.23(2H, s), 4.41(2H, d, J=5.3 Hz), 4.65(2H, d, J=5.7 Hz), 5.00(1H, brs), 5.24(1H, d, J=10.3 Hz), 5.36(1H, d, J=17.2 Hz), 5.55(1H, d, J=1.8 Hz), 5.90–6.00(1H, m), 6.25(1H, d, J=1.9 Hz), 6.81(1H, brs), 7.00–7.40(4H, m).

EXAMPLE 78

4-morpholino-2-[3-(2-propenyloxycarbonylamino)benzylamino]-6-(5-propyl-1,3-oxazol-2-ylthiomethyl)pyridine $^1$H-NMR(CDCl$_3$) δ: 0.94(3H, t, J=7.4 Hz), 1.20–1.40(2H, m), 2.57(2H, t, J=7.4 Hz), 3.15(4H, t, J=5.0 Hz), 3.76(4H, t, J=4.9 Hz), 4.25(2H, s), 4.41(2H, d, J=4.7 Hz), 4.65(2H, d, J=5.8 Hz), 5.25(1H, d, J=10.0 Hz), 5.36(1H, d, J=18.8 Hz), 5.55(1H, d, J=1.5 Hz), 5.90–6.00(1H, m), 6.24(1H, d, J=1.7 Hz), 6.70(1H, s), 7.00–7.40(4H, m)

EXAMPLE 79

6-(benzothiazol-2-ylthiomethyl)-4-morpholino-2-[3-(2-propenyloxycarbonylamino)benzylamino]pyridine $^1$H-NMR(CDCl$_3$) δ: 3.14(4H, t, J=5.0 Hz), 3.47(4H, t, J=5.0 Hz), 4.42(2H, d, J=5.9 Hz), 4.49(2H, s), 4.65(2H, d, J=6.2 Hz), 4.92(1H, t, J=5.9 Hz), 5.25(1H, dd, J=2.7 Hz, 10.1 Hz), 5.35(1H, dd, J=2.7 Hz, 17.1 Hz), 5.57(1H, d, J=2.0 Hz), 5.96(1H, ddt, J=6.2 Hz, 10.1 Hz, 17.1 Hz), 6.36(1H, d, J=2.0 Hz), 6.71(1H, brs), 7.05(1H, d, J=7.3 Hz), 7.24–7.33 (3H, m), 7.36–7.43(2H, m), 7.74(1H, d, J=7.9 Hz), 7.86 (1H, d, J=8.2 Hz).

EXAMPLE 80

6-(5-ethyl-2-thienylthiomethyl)-4-morpholino-2-[3-(2-propenyloxycarbonylamino)benzylamino]pyridine $^1$H-NMR(CDCl$_3$) δ: 1.26(3H, t, J=7.5 Hz), 2.77(2H, q, J=7.5 Hz), 3.11(4H, t, J=5.0 Hz), 3.75(4H, t, J=5.0 Hz), 3.83(2H, s), 4.41(2H, d, J=5.9 Hz), 4.65(2H, d, J=5.7 Hz), 4.95(1H, brs), 5.26(1H, d, J=10.4 Hz), 5.35(1H, d, J=17.2 Hz), 5.55(1H, d, J=2.0 Hz), 5.90–6.00 (1H, m), 5.95(1H, d, J=1.8 Hz), 6.60(1H. d, J=3.5 Hz), 6.67(1H, brs), 6.86(1H. d, J=3.6 Hz), 7.07(1H, d, J=7.3 Hz), 7.20–7.40(3H, m).

EXAMPLE 81

4-morpholino-2-[3-(2-propenyloxycarbonylamino)benzylamino]-6-(2-pyridylthiomethyl)pyridine $^1$H-NMR(CDCl$_3$) δ: 3.14(4H, t, J=4.9 Hz), 3.74(4H, t, J=4.9 Hz), 4.32(2H, s), 4.40(2H, d, J=5.6 Hz), 4.65(2H, d, J=5.7 Hz), 5.15(1H, brs), 5.25(1H, dd, J=1.3 Hz, 10.4 Hz), 5.35(1H, dd, J=1.3 Hz, 17.2 Hz), 5.53(1H, d, J=2.0 Hz), 5.90–6.00(1H, m), 6.33(1H, d, J=2.0 Hz), 6.68(1H, brs), 6.95–6.99(1H, m), 7.06(1H, d, J=6.9 Hz), 7.20–7.50 (5H, m), 8.40–8.45(1H, m).

EXAMPLE 82

4-morpholino-2-[3-(2-propenyloxycarbonylamino)benzylamino]-6-(2-pyrimidinylthiomethyl)pyridine $^1$H-NMR(CDCl$_3$) δ: 3.15(4H, t, J=4.9 Hz), 3.75(4H, t, J=4.9 Hz), 4.34(2H, s), 4.41(2H, d, J=5.9 Hz), 4.66(2H, d, J=5.6 Hz), 4.95(1H, brs), 5.24(1H, dd, J=1.4 Hz, 10.4 Hz), 5.36(1H, dd, J=1.4 Hz, 17.3 Hz), 5.55(1H, d, J=2.3 Hz), 5.90–6.00(1H, m), 6.35(1H, d, J=2.3 Hz), 6.74(1H, brs), 6.95(1H, t, J=4.8 Hz), 7.07(1H, d, J=6.6 Hz), 7.20–7.40(3H, m), 8.52(2H, d, J=4.8 Hz).

EXAMPLE 83

6-(3-methylphenylthiomethyl)-4-morpholino-2-[3-(2-propenyloxycarbonylamino)benzylamino]pyridine $^1$H-NMR(CDCl$_3$) δ: 2.28(3H, s), 3.12(4H, t, J=5.0 Hz), 3.74(4H, t, J=5.0 Hz), 4.01(2H, s), 4.41(2H, d, J=5.8 Hz), 4.65(2H, d, J=5.6 Hz), 4.95(1H, brs), 5.25(1H, dd, J=1.3 Hz, 10.5 Hz), 5.32(1H, dd, J=1.3 Hz, 17.3 Hz), 5.55(1H, d, J=2.0 Hz), 5.90–6.00(1H, m), 6.16 (1H, d, J=2.0 Hz), 6.65(1H, brs), 6.90–7.40(8H, m).

EXAMPLE 84

6-(5-indanylthiomethyl)-4-morpholino-2-[3-(2-propenyloxycarbonylamino)benzylamino]pyridine $^1$H-NMR(CDCl$_3$) δ: 2.04(2H, quintet, J=7.6 Hz), 2.84 (4H, t, J=7.3 Hz), 3.11(4H, t, J=5.0 Hz), 3.74(4H, t, J=4.7 Hz), 3.99(2H, s), 4.40(2H, d, J=5.7 Hz), 4.65(2H, d, J=5.6 Hz), 5.00(1H, brs), 5.26(1H, d, J=10.4 Hz), 5.36(1H, d, J=17.2 Hz), 5.54(1H, d, J=1.8 Hz), 5.90–6.00(1H, m), 6.12(1H, d, J=1.9 Hz), 6.67(1H, brs), 7.00–7.44(7H, m).

EXAMPLE 85

6-(5-ethyl-2-furylthiomethyl)-4-morpholino-2-[3-(2-propenyloxycarbonylamino)benzylamino]pyridine $^1$H-NMR(CDCl$_3$) δ: 1.19(3H, t, J=7.6 Hz), 2.61(2H, q, J=7.6 Hz), 3.12(4H, t, J=4.9 Hz), 3.75(4H, t, J=4.9 Hz), 3.83(2H, s), 4.40(2H, d, J=5.9 Hz), 4.65(2H, d, J=5.7 Hz), 5.25(1H, dd, J=1.4 Hz, 10.6 Hz), 5.35(1H, dd, J=1.4 Hz, 17.1 Hz), 5.53(1H, d, J=1.9 Hz), 5.91–5.97 (3H, m), 6.34 (1H, d, J=3.1 Hz), 6.65(1H, brs), 7.06(1H, d, J=6.6 Hz), 7.22–7.38(2H, m), 7.39(1H, s).

EXAMPLE 86

6-(5-ethyl-1,3-thiazol-2-ylthiomethyl)-4-morpholino-2-[3-(2-propenyloxycarbonylamino)-5-trifluoromethylbenzylamino]pyridine $^1$H-NMR(CDCl$_3$) δ: 1.26(3H, t, J=7.5 Hz), 2.77(2H, q, J=7.5 Hz), 3.14(4H, dd, J=4.7 Hz, 5.0 Hz), 3.75(4H, dd, J=4.7 Hz, 5.0 Hz), 4.25 (2H, s), 4.49(2H, d, J=5.7 Hz), 4.66(2H, d, J=5.7 Hz), 5.17–5.36 (1H, brs), 5.26(1H, d, J=10.4 Hz), 5.35(1H, d, J=17.2 Hz), 5.53(1H, d, J=1.9 Hz), 5.95(1H, ddt, J=5.7 Hz, 10.4 Hz, 17.2 Hz), 6.21(1H, d, J=1.9 Hz), 7.25–7.26(1H, brs), 7.28(1H, s), 7.33(1H, s), 7.54(1H, s), 7.78(1H, s).

EXAMPLE 87

6-(5-ethyl-4-methyl-1,3-thiazol-2-ylthiomethyl)-4-morpholino-2-[3-(2-propenyloxycarbonylamino)-5-trifluoromethylbenzylamino]pyridine $^1$H-NMR(CDCl$_3$) δ: 1.19(3H, t, J=7.5 Hz), 2.27(3H, s), 2.67(2H, q, J=7.5 Hz), 3.15(4H, dd, J=4.8 Hz, 5.0 Hz), 3.75(4H, dd, J=4.8 Hz, 5.0 Hz), 4.22(2H, s), 4.48(2H, d, J=6.0 Hz), 4.66(2H, d, J=5.6 Hz), 5.21–5.40(1H, brs), 5.26 (1H, d, J=10.4 Hz), 5.35(1H, d, J=17.1 Hz), 5.52(1H, d, J=1.9 Hz), 5.94(1H, ddt, J=5.6 Hz, 10.4 Hz, 17.1 Hz), 6.25 (1H, d, J=1.9 Hz), 7.16(1H, brs), 7.28(1H, s), 7.53(1H, s), 7.76(1H, s).

EXAMPLE 88

6-(2-cyclopenteno[d]thiazolylthiomethyl)-4-morpholino-2-[3-(2-propenyloxycarbonylamino)-5-trifluoromethylbenzylamino]pyridine $^1$H-NMR(CDCl$_3$) δ: 2.42–2.49(2H, m), 2.76–2.86(4H, m), 3.13–3.17(4H, m), 3.74–3.77(4H, m), 4.24(2H, s), 4.48 (2H, d, J=6.2 Hz), 4.66(2H, d, J=5.7 Hz), 5.20–5.35(1H, brs), 5.26(1H, d, J=10.5 Hz), 5.35(1H, d, J=17.2 Hz), 5.53(1H, d, J=2.0 Hz), 5.95 (1H, ddt, J=5.7 Hz, 10.5 Hz, 17.2 Hz), 6.23(1H, d, J=2.0 Hz), 7.12(1H, brs), 7.28(1H, s), 7.54(1H, s), 7.76(1H, s).

EXAMPLE 89

6-(5-ethyl-4-methyl-1,3-thiazol-2-ylthiomethyl)-2-[3-methoxy-5-(2-propenyloxycarbonylamino)benzylamino]-4-morpholinopyridine $^1$H-NMR(CDCl$_3$) δ: 1.20(3H, t, J=7.3 Hz), 2.28(3H, s), 2.68(2H, q, J=7.3 Hz), 3.14(4H, t, J=5.0 Hz), 3.76(4H, t, J=5.0 Hz), 3.78(3H, s), 4.22(2H, s), 4.37(2H, d, J=5.9 Hz), 4.65(2H, d, J=5.6 Hz), 4.90 (1H, brs), 5.10(1H, d, J=10.4 Hz), 5.35(1H, d, J=17.1 Hz), 5.55(1H, d, J=1.9 Hz), 5.90–6.00(1H, m), 6.24(1H, d, J=1.9 Hz), 6.62(1H, s), 6.75(1H, s), 6.88(1H, s), 7.05(1H, s).

EXAMPLE 90

6-(2-cyclopenteno[d]thiazolylthiomethyl)-2-[3-methoxy-5-(2-propenyloxycarbonylamino)benzylamino]-4-morpholinopyridine $^1$H-NMR(CDCl$_3$) δ: 2.40–2.50(2H, m), 2.75–2.90(4H, m), 3.14 (4H, t, J=5.0 Hz), 3.76(4H, t, J=5.0 Hz), 3.78(3H, s), 4.25(2H, s), 4.37(2H, d, J=5.7 Hz), 4.65(2H, d, J=5.6 Hz), 5.00(1H, brs), 5.26 (1H, d, J=11.4 Hz), 5.35(1H, d, J=17.1 Hz), 5.55(1H, d, J=1.8 Hz), 5.90–6.00(1H, m), 6.20(1H, d, J=1.9 Hz), 6.62(1H, s), 6.77(1H, brs), 6.88(1H, s), 7.05(1H, s).

EXAMPLE 91

6-[5-(1-hydroxy)ethyl-1,3-thiazol-2-ylthiomethyl]-2-[3-methoxy-5-(2-propenyloxycarbonylamino)benzylamino]-4-morpholinopyridine $^1$H-NMR(CDCl$_3$) δ: 1.55(3H, d, J=6.4 Hz), 3.16(4H, t, J=4.7 Hz), 3.76(4H, t, J=4.7 Hz), 3.78(3H, s), 4.25(2H, s), 4.36(2H, d, J=5.6 Hz), 4.65(2H, dd, J=1.4 Hz, 5.7 Hz), 5.13(1H, q, J=6.4 Hz), 5.18 (1H, brs), 5.25(1H, dq, J=1.4 Hz, 10.5 Hz), 5.35(1H, dq, J=1.4 Hz, 17.0 Hz), 5.55(1H, s), 5.95(1H, ddt, J=1.4 Hz, 10.5 Hz, 17.0 Hz), 6.23 (1H, s), 6.60(1H, s), 6.85(1H, s), 6.92(1H, brs), 7.08(1H, s), 7.46 (1H, s).

EXAMPLE 92

6-(5-ethyl-1,3-thiazol-2-ylthiomethyl)-2-{1-[3-methoxy-5-(2-propenyloxycarbonylamino)phenyl]propylamino}-4-morpholinopyridine $^1$H-NMR(CDCl$_3$) δ: 0.94(3H, t, J=7.4 Hz), 1.26(3H, t, J=7.5 Hz), 1.72–1.90(2H, m), 2.77(2H, q, J=7.5 Hz), 2.99–3.12(4H, m), 3.68–3.73(4H, m), 3.77(3H, s), 4.20–4.28(1H, m), 4.24(2H, s), 4.64(2H, d, J=5.6 Hz), 4.99–5.09(1H, brs), 5.25(1H, d, J=10.3 Hz), 5.35(1H, d, J=17.1 Hz), 5.42(1H, d, J=2.0 Hz), 5.95(1H, ddt, J=5.6 Hz, 10.3 Hz, 17.1 Hz), 6.16(1H, d, J=2.0 Hz), 6.60(1H, s), 6.70(1H, brs), 6.90(1H, s), 6.97(1H, s), 7.33(1H, s).

EXAMPLE 93

6-(5-ethyl-1,3-thiazol-2-ylthiomethyl)-4-morpholino-2-{1-[3-(2-propenyloxycarbonylamino)phenyl]propylamino}-pyridine $^1$H-NMR(CDCl$_3$) δ: 0.94(3H, t, J=7.3 Hz), 1.28(3H, t, J=7.6 Hz), 1.73–1.93(2H, m), 2.77(2H, q, J=7.6 Hz), 2.96–3.12(4H, m), 3.63–3.77(4H, m), 4.25(2H, s), 4.29(1H, m), 4.65(2H, d, J=5.7 Hz), 5.02 (1H, d, J=2.6 Hz), 5.26(1H, d, J=10.5 Hz), 5.35(1H, d, J=17.2 Hz), 5.39(1H, d, J=2.0 Hz), 5.96(1H, m), 6.16(1H, d, J=2.0 Hz), 6.75(1H, brs), 7.04(1H, m), 7.20–7.30(2H, m), 7.33(1H, s), 7.39(1H, m).

EXAMPLE 94

6-(2-cyclopenteno[d]thiazolylthiomethyl)-2-[3-methyl-5-(2-propenyloxycarbonylamino)benzylamino]-4-morpholinopyridine $^1$H-NMR(CDCl$_3$) δ: 2.30(3H, s), 2.38–2.53(2H, m), 2.76–2.90 (4H, m), 3.10–3.22(4H, m), 3.70–3.85(4H, m), 4.25(2H, s), 4.36 (2H, d, J=5.8 Hz), 4.64(2H, d, J=5.8 Hz), 4.89(1H, t, J=5.8 Hz), 5.25 (1H, d, J=10.0 Hz), 5.34(1H, d, J=17.2 Hz), 5.56(1H, d, J=2.0 Hz), 5.95(1H, ddt, J=5.8 Hz, 10.0 Hz, 17.2 Hz), 6.22(1H, d, J=2.0 Hz), 6.74 (1H, brs), 6.88(1H, m), 7.12–7.20(2H, m).

EXAMPLE 95

6-(5-ethyl-1,3-thiazol-2-ylthiomethyl)-2-[3-methyl-5-(2-propenyloxycarbonylamino)benzylamino]-4-morpholinopyridine $^1$H-NMR(CDCl$_3$) δ: 1.26(3H, t, J=7.6 Hz), 2.30(3H, s), 2.76(2H, q, J=7.6 Hz), 3.10–3.18(4H, m), 3.71–3.80(4H, m), 4.23(2H, s), 4.36(2H, d, J=5.7 Hz), 4.64(2H, d, J=5.7 Hz), 4.95(1H, m), 5.25(1H, d, J=10.5 Hz), 5.35(1H, d, J=15.8 Hz), 5.56(1H, d, J=2.0 Hz), 5.95 (1H, m), 6.22(1H, d, J=2.0 Hz), 6.76(1H, brs), 6.88(1H, m), 7.13–7.22(2H, m), 7.34(1H, s).

EXAMPLE 96

6-(4-ethyl-1,3-thiazol-2-ylthiomethyl)-2-[3-methyl-5-(2-propenyloxycarbonylamino)benzylamino]-4-morpholinopyridine $^1$H-NMR(CDCl$_3$) δ: 1.27(3H, t, J=7.5 Hz), 2.31(3H, s), 2.75(2H, q, J=7.5 Hz), 3.09–3.22(4H, m), 3.70–3.81(4H, m), 4.28(2H, s), 4.36(2H, d, J=5.9 Hz), 4.65(2H, d, J=5.7 Hz), 4.89(1H, t, J=5.9 Hz), 5.24(1H, d, J=9.1 Hz), 5.35(1H, d, J=17.2 Hz), 5.57(1H, d, J=2.1 Hz), 5.95(1H, m), 6.26(1H, d, J=2.1 Hz), 6.68(1H, brs), 6.74 (1H, s), 6.89(1H, m), 7.11–7.22(2H, m).

EXAMPLE 97

6-(5-ethyl-4-methyl-1,3-thiazol-2-ylthiomethyl)-2-[3-methyl-5-(2-propenyloxycarbonylamino)benzylamino]-4-morpholinopyridine $^1$H-NMR(CDCl$_3$) δ: 1.20(3H, t, J=7.5 Hz), 2.28(3H, s), 2.30(3H, s), 2.68(2H, q, J=7.5 Hz), 3.09–3.18(4H, m), 3.70–3.81(4H, m), 4.23(2H, s), 4.36(2H, d, J=5.9 Hz), 4.64(2H, d, J=5.7 Hz), 4.94(1H, t, J=5.9 Hz), 5.23(1H, d, J=10.5 Hz), 5.35(1H, d, J=15.7 Hz), 5.56 (1H, d, J=1.8 Hz), 5.95(1H, m), 6.24(1H, d, J=1.8 Hz), 6.76(1H, brs), 6.88(1H, m), 7.12–7.21(2H, m).

EXAMPLE 98

6-(5-ethyl-1,3,4-thiadiazol-2-ylthiomethyl)-4-morpholino-2-{1-[3-(2-propenyloxycarbonylamino)phenyl]butylamino}pyridine $^1$H-NMR(CDCl$_3$) δ: 0.91(3H, t, J=7.3 Hz), 1.20–1.50(2H, m), 1.37(3H, t, J=7.6 Hz), 1.65–1.85(2H, m), 3.00–3.15(4H, m), 3.06 (2H, q, J=7.6 Hz), 3.65–3.75(4H, m), 4.30–4.45 (1H, m), 4.38(2H, s), 4.65(2H, d, J=5.6 Hz), 5.00(1H, d, J=4.9 Hz), 5.20–5.45(3H, m), 5.90–6.05(1H, m), 6.23(1H, d, J=1.9 Hz), 6.75(1H, s), 7.00–7.10(1H, m), 7.20–7.30(2H, m), 7.40(1H, s).

EXAMPLE 99

6-(5-ethyl-1,3,4-thiadiazol-2-ylthiomethyl)-2-[3-methylthio-5-(2-propenyloxycarbonylamino)benzylamino]-4-morpholinopyridine $^1$H-NMR(CDCl$_3$) δ: 1.37(3H, t, J=7.6 Hz), 2.46(3H, s), 3.05(2H, q, J=7.6 Hz), 3.10–3.20(4H, m), 3.70–3.80(4H, m), 4.38(2H, d, J=5.8 Hz), 4.40(2H, s), 4.65(2H, dd, J=1.3 Hz, 7.3 Hz), 5.08(1H, brs), 5.25(1H, dd, J=1.3 Hz, 10.3 Hz), 5.35(1H, dd, J=1.3 Hz, 10.3 Hz), 5.55 (1H, d, J=1.9 Hz), 5.85–6.05(1H, m), 6.31(1H, d, J=1.9 Hz), 6.85 (1H, s), 6.94(1H, s), 7.07(1H, s), 7.33(1H, s).

EXAMPLE 100

Preparation of 6-(5-ethyl-1,3,4-thiadiazol-2-ylthiomethyl)-4-morpholino-2-[5-(2-propenyloxycarbonylamino)-2-thienylmethylamino]pyridine (1) Preparation of 2-{N-[5-(2-propenyloxycarbonylamino)thiophen-2-ylmethyl]-N-(2-trimethylsilylethoxycarbonyl)]amino-4-morpholino-6-(2-tetrahydropyranyl)oxymethylpyridine To a solution of 2-trimethylsilylethyl N-[4-morpholino-6-(2-tetrahydropyranyloxymethyl)-2-pyridyl]carbamate (212 mg) obtained in the same manner as in Example 51-(2) in dimethylformamide (10 ml), 60% sodium hydride (23 mg) was added under cooling with ice, followed by stirring at the same temperature for 15 minutes. A solution of ethyl 6-bromomethyl-2-thiophenecarboxylate (151 mg) in dimethylformamide (5 ml) was added thereto, followed by stirring for two hours. Water was added to the reaction solution, followed by extraction with ethyl acetate. The organic layer was washed with a saturated sodium chloride aqueous solution and then dried over anhydrous magnesium sulfate. Then, the solvent was distilled off under reduced pressure. The residue was purified by silica gel column chromatography (hexane/ethyl acetate=2:1) to obtain a pale yellow oily substance (170 mg). The obtained oily substance was dissolved in methanol (5 ml), and a 1 N sodium hydroxide aqueous solution (1.4 ml) was added thereto, followed by stirring overnight. Methanol was distilled off under reduced pressure, and the residue was subjected to liquid separation between water and ethyl ether. The aqueous layer was acidified with 1 N hydrochloric acid and then extracted with chloroform. The solvent was distilled off, and the residue obtained was dissolved in dioxane (3 ml), and diphenylphosphoryl azide (45 µl) and triethylamine (37 µl) were added thereto, followed by stirring for two hours under cooling with ice. Then, allyl alcohol (1.5 ml) was added thereto, followed by heating at 110° C. for 2.5 hours. The reaction solution was poured into a saturated sodium hydrogen carbonate aqueous solution, followed by extraction with chloroform. The organic layer was washed with water, and then dried over anhydrous magnesium sulfate. The solvent was distilled off under reduced pressure, and the residue was purified by silica gel column chromatography (hexane/ethyl acetate=3:2) to obtain the above identified compound (64 mg).

(2) Preparation of 6-(5-ethyl-1,3,4-thiadiazol-2-ylthiomethyl)-4-morpholino-2-[5-(2-propenyloxycarbonylamino)-2-thienylmethylamino]pyridine 2-{N-[5-(2-propenyloxycarbonylamino)-2-thienylmethyl]-N-(2-trimethylsilylethoxycarbonyl)]amino}-4-morpholino-6-(2-tetrahydropyranyl)oxymethylpyridine (63 mg) was dissolved in ethanol (2 ml), and p-toluenesulfonic acid monohydrate (23 mg) was added thereto, followed by stirring at 50° C. for two hours. After cooling naturally, the reaction solution was diluted with ethyl acetate, washed with a saturated sodium hydrogen carbonate aqueous solution and a saturated sodium chloride aqueous solution and then dried over anhydrous magnesium sulfate. The solvent was distilled off under reduced pressure, and the residue was purified by silica gel column chromatography (ethyl acetate/heptane=2/1) to obtain a white amorphous solid (48 mg). The product was dissolved in chloroform (1 ml), and methanesulfonyl chloride (9.5 µl) was added under cooling with ice, followed by stirring at room temperature for two hours. The reaction solution was diluted with ethyl acetate, washed sequentially with water, a saturated sodium hydrogen carbonate aqueous solution and a saturated sodium chloride aqueous solution and dried over anhydrous magnesium sulfate. The solvent was distilled off under reduced pressure, and the residue was dissolved in dimethylformamide (1 ml). Potassium carbonate (16 mg) and 5-ethyl-2-mercapto-1,3,4-thiadiazole (8 mg) were added thereto, followed by stirring at room temperature for two hours. Ethyl acetate was added to the reaction solution, and the mixture was washed sequentially with water and a saturated sodium chloride aqueous solution and then dried over anhydrous magnesium sulfate. The solvent was distilled off under reduced pressure. The residue obtained was dissolved in tetrahydrofuran (1 ml), and a 1 M tetrabutylammonium fluoride-tetrahydrofuran solution (62 µl) was added thereto, followed by stirring at room temperature for 1.5 hours. The reaction solution was poured into a saturated ammonium chloride aqueous solution and extracted with ethyl acetate. The organic layer was dried over anhydrous magnesium sulfate. The solvent was distilled off under reduced pressure, and the residue was purified by silica gel column chromatography (chloroform/methanol=50/1→20/1) to obtain the above identified compound (15 mg) as a pale yellow oily substance.

$^1$H-NMR(CDCl$_3$) δ: 1.40(3H, t, J=7.6 Hz), 3.08(2H, q, J=7.6 Hz), 3.21(4H, t, J=5.0 Hz), 3.80(4H, t,J=5.0 Hz), 4.45(2H, s), 4.55(2H, d, J=5.3 Hz), 4.68(2H, dd, J=1.4 Hz, 5.7 Hz), 4.91(1H, d, J=5.3 Hz), 5.27(1H, dd, J=1.4 Hz, 10.4 Hz), 5.36(1H, dd, J=1.4 Hz, 17.2 Hz), 5.65 (1H, d, J=2.0 Hz), 5.97(1H, ddt, J=5.7 Hz, 10.4 Hz, 17.2 Hz), 6.35(1H, d, J=2.0 Hz), 6.48(1H, d, J=3.7 Hz), 6.73(1H, d, J=3.7 Hz), 7.27(1H, brs).

EXAMPLE 101

Preparation of 6-(5-ethyl-1,3,4-thiadiazol-2-ylthiomethyl)-2-[3-methyl-5-(2-propenyloxycarbonylamino)benzylamino]-4-morpholinopyridine (1) Preparation of 2-[N-tert-butoxycarbonyl-N-(3-methyl-5-nitrobenzyl)amino]-6-(5-ethyl-1,3,4-thiadiazol-2-ylthiomethyl)-4-morpholinopyridine To a solution of tert-butyl N-[6-(5-ethyl-1,3,4-thiadiazol-2-ylthiomethyl)-4-morpholino-2-pyridyl]carbamate (200 mg) obtained in Example 1-(5) in dimethylformamide (2 ml), 60% sodium hydride (30 mg) was added under cooling with ice, followed by stirring at the same temperature for 30 minutes. A solution of 3-methyl-5-nitrobenzyl methanesulfonate (283 mg) in dimethylformamide (1 ml), was added to the reaction solution, followed by stirring at room temperature overnight. The reaction solution was diluted with ethyl acetate, washed with water and a saturated sodium hydrogen carbonate aqueous solution and dried over anhydrous magnesium sulfate. Then, the solvent was distilled off under reduced pressure. The residue was purified by silica gel column chromatography (heptane/ethyl acetate=1:1) to obtain the above identified compound (314 mg) as a pale yellow oily substance.

(2) Preparation of 2-{N-tert-butoxycarbonyl-N-[3-methyl-5-(2-propenyloxycarbonylamino)benzyl]amino}-6-(5-ethyl-1,3,4-thiadiazol-2-ylthiomethyl)-4-morpholinopyridine A mixture comprising 2-[N-tert-butoxycarbonyl-N-(3-methyl-5-nitrobenzyl)amino]-6-(5-ethyl-1,3,4-thiadiazol-2- ylthiomethyl)-4-morpholinopyridine (110 mg), iron powder (53 mg) and ammonium chloride (100 mg), was refluxed for 2.5 hours in methanol (6 ml)-water (3 ml). The reaction solution was subjected to celite filtration, and ethyl acetate was added to the filtrate, followed by washing with a saturated sodium hydrogen carbonate aqueous solution. The organic layer was washed with a saturated sodium chloride aqueous solution and then, dried over anhydrous magnesium sulfate. The solvent was distilled off under reduced pressure. The residue was dissolved in chloroform (1 ml), and 4-dimethylaminopyridine (34 mg) and allyl chloroformate (0.030 ml) were added thereto, followed by stirring at room temperature overnight. The reaction solution was diluted with ethyl acetate, washed with water and a saturated sodium chloride aqueous solution and then, dried over anhydrous magnesium sulfate. Then, the solvent was distilled off under reduced pressure. The residue was purified by silica gel column chromatography (ethyl acetate/hexane= 1/1) to obtain the above identified compound (92 mg) as a yellow amorphous solid.

(3) Preparation of 6-(5-ethyl-1,3,4-thiadiazol-2-ylthiomethyl)-2-[3-methyl-5-(2-propenyloxycarbonylamino)benzylamino]-4-morpholinopyridine 2-{N-tert-butoxycarbonyl-N-[3-methyl-5-(2-propenyloxycarbonylamino)benzyl]amino}-6-(5-ethyl-1,3,4-thiadiazol-2-ylthiomethyl)-4-morpholinopyridine (92 mg) was dissolved in trifluoroacetic acid (1 ml), followed by stirring at room temperature for one hour. The reaction solution was concentrated under reduced pressure, and the residue was subjected to liquid separation with ethyl acetate-a saturated sodium hydrogen carbonate aqueous solution. The organic layer was washed with a saturated sodium chloride aqueous solution and then dried over anhydrous magnesium sulfate. The solvent was distilled off under reduced pressure, and the residue was purified by silica gel column chromatography (chloroform/methanol=50/1) to obtain the above identified compound (55 mg) as a pale yellow solid.

$^1$H-NMR(CDCl$_3$) δ: 1.37(3H, t, J=7.6 Hz), 2.31(3H, s), 3.06(2H, q, J=7.6 Hz), 3.10–3.20(4H, m), 3.70–3.80(4H, m), 4.37(2H, d, J=5.6 Hz), 4.41(2H, s), 4.65(2H, dd, J=1.2 Hz, 5.7 Hz), 4.94(1H, brs), 5.20–5.30(1H, m), 5.30–5.40(1H, m), 5.57(1H, d, J=1.9 Hz), 5.85–6.05(1H, m), 6.31(1H, d, J=1.9 Hz), 6.73(1H, brs), 6.89(1H, s), 7.16(2H, s).

EXAMPLE 102

Preparation of 6-(5-ethyl-1,3,4-thiadiazol-2-ylthiomethyl)-2-[3-methoxymethyl-5-(2-propenyloxycarbonylamino)benzylamino]-4-morpholinopyridine The above identified compound was obtained in the same manner as in Example 101 except that 3-methyl-5-nitrobenzyl methanesulfonate used in Example 101-(1) was changed to 3-methoxymethyl-5-nitrobenzyl methanesulfonate.

$^1$H-NMR(CDCl$_3$) δ: 1.37(3H, t, J=7.5 Hz), 3.06(2H, q, J=7.5 Hz), 3.10–3.19(4H, m), 3.38(3H, s), 3.72–3.79(4H, m), 4.38–4.46(6H, m), 4.65(2H, d, J=5.7 Hz), 4.92(1H, m), 5.25(1H, d, J=13.4 Hz), 5.35(1H, d, J=17.3 Hz), 5.56(1H, brs), 5.95(1H, m), 6.30(1H, brs), 6.80(1H, m), 7.05(1H, brs), 7.27–7.36(2H, m).

EXAMPLE 103

Preparation of 6-(5-ethyl-1,3,4-thiadiazol-2-ylthiomethyl)-2-[3-hydroxymethyl-5-(2-propenyloxycarbonylamino)benzylamino]-4-morpholinopyridine (1) Preparation of 2-{N-tert-butoxycarbonyl-N-[3-(2-propenyloxycarbonylamino)-5-(2-tetrahydropyranyl)oxymethylbenzyl]amino}-6-(5-ethyl-1,3,4-thiadiazol-2-ylthiomethyl)-4-morpholinopyridine The above identified compound was obtained in the same manner as in Example 101-(1) and (2) except that 3-methyl-5-nitrobenzyl methanesulfonate used in Example 101-(1) was changed to 3-(2-tetrahydropyranyl)oxymethyl-5-nitrobenzyl methanesulfonate.

(2) Preparation of 6-(5-ethyl-1,3,4-thiadiazol-2-ylthiomethyl)-2-[3-hydroxymethyl-5-(2-propenyloxycarbonylamino)benzylamino]-4-morpholinopyridine 2-{N-tert-butoxycarbonyl-N-[3-(2-propenyloxycarbonylamino)-5-(2-tetrahydropyranyl)oxymethylbenzyl]amino}-6-(5-ethyl-1,3,4-thiadiazol-2-ylthiomethyl)-4-morpholinopyridine (51 mg) was dissolved in 10% hydrogen chloride-methanol (2 ml), followed by stirring at 60° C. for two hours. After cooling naturally, the reaction solution was diluted with ethyl acetate, washed with a saturated sodium hydrogen carbonate aqueous solution and a saturated sodium chloride aqueous solution and then, dried over anhydrous sodium sulfate. The solvent was distilled off under reduced pressure, and the residue was purified by thin layer chromatography for separation (chloroform/methanol=10/1) to obtain the above identified compound (55 mg) as a pale yellow amorphous solid.

$^1$H-NMR(CDCl$_3$) δ: 1.36(3H, t, J=7.6 Hz), 3.04(2H, q, J=7.6 Hz), 3.16(4H, dd, J=4.7 Hz, 4.9 Hz), 3.76(4H, dd, J=4.7 Hz, 4.9 Hz), 4.39 (4H, m), 4.64–4.66(4H, m), 5.02–5.15(1H, brs), 5.25(1H, d, J=10.5 Hz), 5.35(1H, d, J=17.2 Hz), 5.56(1H, d, J=1.8 Hz), 5.95(1H, ddt, J=5.6 Hz, 10.5 Hz, 17.2 Hz), 6.30(1H, d, J=1.8 Hz), 6.90–7.00 (1H, brs), 7.06(1H, s), 7.29(1H, s), 7.32(1H, s).

EXAMPLE 104

Preparation of 6-(2-cyclopenteno[d]thiazolylthiomethyl)-2-[3-hydroxymethyl-5-(2-propenyloxycarbonylamino)benzylamino]-4-morpholinopyridine The same operation as in Example 101-(1) and (2) was carried out except that 3-methyl-5-nitrobenzyl methanesulfonate used in Example 101-(1) was changed to 3-(2-tetrahydropyranyl)oxymethyl-5-nitrobenzyl methanesulfonate, and tert-butyl N-[6-(5-ethyl-1,3,4-thiadiazol-2-ylthiomethyl)-4-morpholino-2-pyridyl] carbamate was changed to tert-butyl N-[6-(2 -cyclopenteno[d]thiazolylthiomethyl)-4-morpholino-2-pyridyl]carbamate, followed by the same operation as in Example 103-(2) to obtain the above identified compound.

$^1$H-NMR(CDCl$_3$) δ: 2.38–2.50(2H, m), 2.75–2.90(4H, m), 3.15 (4H, t, J=5.0 Hz), 3.75(4H, t, J=5.0 Hz), 4.24(2H, s), 4.37(2H, d, J=4.7 Hz), 4.63(2H, s), 4.64(2H, dt, J=1.4 Hz, 5.6 Hz), 5.25(1H, dq, J=1.4 Hz, 10.7 Hz), 5.35(1H, dq, J=1.4 Hz, 17.0 Hz), 5.55(1H, d, J=2.0 Hz), 5.95(1H, ddt, J=5.6 Hz, 10.7 Hz, 17.0 Hz), 6.20(1H, d, J=2.0 Hz), 6.96(1H, s), 7.07(1H, s), 7.30(1H, s), 7.32(1H, s).

Compounds of Examples 105 to 108 were obtained in the same manner as in Example 64 except that the material used in Example 64 was changed to the materials corresponding to the respective desired compounds.

EXAMPLE 105

2-[3-chloro-5-(2-propenyloxycarbonylamino)benzylamino]-6-(5-ethyl-1,3-thiazol-2-ylthiomethyl)-4-morpholinopyridine $^1$H-NMR(CDCl$_3$) δ: 1.26(3H, t, J=7.5 Hz), 2.77(2H, q, J=7.5 Hz), 3.14(4H, t, J=4.9 Hz), 3.76(4H, t, J=4.9 Hz), 4.26(2H, s), 4.41(2H, d, J=5.8 Hz), 4.65(2H, d, J=5.6 Hz), 5.26(1H, dd, J=1.3 Hz, 10.4 Hz), 5.35(1H, dd, J=1.3 Hz, 17.4 Hz), 5.52(1H, d, J=1.9 Hz), 5.85–6.05 (1H, m), 6.21 (1H, d, J=1.9 Hz), 6.95(1H, s), 7.03(1H, s), 7.25(1H, s), 7.34(1H, s), 7.50(1H, s).

EXAMPLE 106

2-[3-chloro-5-(2-propenyloxycarbonylamino) benzylamino]-6-(5-ethyl-4-methyl-1,3-thiazol-2-ylthiomethyl)-4-morpholinopyridine $^1$H-NMR(CDCl$_3$) δ: 1.20(3H, t, J=7.5 Hz), 2.28(3H, s), 2.68(2H, q, J=7.5 Hz), 3.15(4H, t, J=4.8 Hz), 3.77(4H, t, J=4.8 Hz), 4.22(2H, s), 4.41(2H, d, J=5.9 Hz), 4.65(2H, d, J=5.8 Hz), 4.95(1H, brs), 5.25(1H, dd, J=1.0 Hz, 10.4 Hz), 5.35(1H, dd, J=1.0 Hz, 17.3 Hz), 5.53 (1H, d, J=1.9 Hz), 5.90–6.00(1H, m), 6.24(1H, d, J=1.9 Hz), 6.90 (1H, brs), 7.04(1H, s), 7.21(1H, s), 7.49(1H, s).

EXAMPLE 107

2-[3-chloro-5-(2-propenyloxycarbonylamino) benzylamino]-6-(2-cyclopenteno[d] thiazolylthiomethyl)-4-morpholinopyridine $^1$H-NMR(CDCl$_3$) δ: 2.42–2.49(2H, m), 2.77–2.87(4H, m), 3.14 (4H, t, J=4.9 Hz), 3.76(4H, t, J=4.9 Hz), 4.24(2H, s), 4.40(2H, d, J=6.3 Hz), 4.65(2H, d, J=5.8 Hz), 5.25(1H, dd, J=1.3 Hz, 10.4 Hz), 5.34(1H, dd, J=1.3 Hz, 17.2 Hz), 5.51(1H, d, J=2.0 Hz), 5.88–5.99 (1H, m), 6.22(1H, d, J=2.0 Hz), 6.90(1H, brs), 7.03(1H, s), 7.21(1H, s), 7.48(1H, s).

EXAMPLE 108

2-[3-chloro-5-(2-propenyloxycarbonylamino) benzylamino]-6-(5-methyl-4-propyl-1,3-thiazol-2-ylthiomethyl)-4-morpholinopyridine $^1$H-NMR(CDCl$_3$) δ: 0.94(3H, t, J=7.5 Hz), 1.57(2H, q, J=7.5 Hz), 2.28(3H, s), 2.62(2H, q, J=7.5 Hz), 3.14(4H, t, J=4.9 Hz), 3.76(4H, t, J=4.9 Hz), 4.23(2H, s), 4.39(2H, d, J=5.9 Hz), 4.65(2H, d, J=5.7 Hz), 4.90(1H, brs), 5.26(1H, d, J=10.4 Hz), 5.35(1H, d, J=17.2 Hz), 5.52(1H, d, J=2.0 Hz), 5.90–6.00(1H, m), 6.23(1H, d, J=2.0 Hz), 6.97(1H, brs), 7.03(1H, s), 7.20(1H, s), 7.49(1H, s).

EXAMPLE 109

Preparation of 6-[2-(5-ethyl-4-methyl-1,3-thiazol-2-yl)ethyl]-4-morpholino-2-[3-(2-propenyloxycarbonylamino)benzylamino]pyridine (1) Preparation of 2-tert-butoxycarbonylamino-6-[2-(5-ethyl-4-methyl-1,3-thiazol-2-yl)ethyl]-4-morpholinopyridine 6-tert-butoxycarbonylamino-4-morpholinopyridine-2-ylpropionic acid (17.57 g) obtained by alkali hydrolysis of the compound obtained in Example 22-(3) and 2-amino-3-pentanone hydrochloride (8.25 g) were dissolved in methylene chloride (200 ml), and a solution of benzotriazol-1-yloxy-tris-pyrrolidinophosphoniumhexafluorophosphate (31.2 g) in methylene chloride (50 ml) and diisopropylethylamine (35 ml) were added thereto, followed by stirring at room temperature for one hour. The reaction solution was concentrated under reduced pressure, and the residue was dissolved in ethyl acetate, washed with a saturated sodium hydrogen carbonate aqueous solution and a saturated sodium chloride aqueous solution and dried over anhydrous magnesium sulfate. The solvent was distilled off under reduced pressure, and the residue was purified by silica gel column chromatography (ethyl acetate). The product was dissolved in tetrahydrofuran (500 ml), and Lawesson's reagent (24.3 g) was added thereto, followed by refluxing under heating for 2.5 hours. Further, Lawesson's reagent (20 g) was additionally added, followed by refluxing for two hours. The reaction solution was concentrated under reduced pressure, and the residue was purified by silica gel column chromatography (hexane/ethyl acetate=1/2) to obtain the above identified compound (5.78 g).

(2) Preparation of 2-(N-tert-butoxycarbonyl-N-3-nitrobenzyl)amino-6-[2-(5-ethyl-4-methyl-1,3-thiazol-2-yl) ethyl]-4-morpholinopyridine 2-tert-butoxycarbonylamino-6-[2-(5-ethyl-4-methyl-1,3-thiazol-2-yl)ethyl]-4-morpholinopyridine (1.0 g) was dissolved in dimethylformamide (20 ml), and 60% sodium hydride (102 mg) was added under cooling with ice, followed by stirring at room temperature for one hour. The reaction solution was cooled with ice, and a solution of 3-nitrobenzyl chloride (476 mg) in dimethylformamide (5 ml), was added thereto, followed by stirring at room temperature for 15 hours. The reaction solution was diluted with ethyl acetate, washed with water and a saturated sodium chloride aqueous solution and dried over anhydrous magnesium sulfate. Then, the solvent was distilled off under reduced pressure. The residue was purified by silica gel column chromatography (hexane/ethyl acetate=1/2) to obtain the above identified compound (1.15 g)

(3) Preparation of 2-[N-tert-butoxycarbonyl-N-3-(2-propenyloxycarbonylamino)benzylamino]-6-[2-(5-ethyl-4-methyl-1,3-thiazol-2-yl)ethyl]-4-morpholinopyridine A mixture comprising 2-(N-tert-butoxycarbonyl-N-3-nitrobenzyl)amino-6-[2-(5-ethyl-4-methyl-1,3-thiazol-2-yl)ethyl]-4-morpholinopyridine (1.15 g), iron powder (335 mg) and ammonium chloride (642 mg), was refluxed for two hours in methanol (40 ml)-water (20 ml). The reaction solution was subjected to celite filtration, and the filtrate was concentrated under reduced pressure. The residue was dissolved in ethyl acetate, washed with a saturated sodium chloride aqueous solution and dried over anhydrous magnesium sulfate. Then, the solvent was distilled off under reduced pressure. The residue was dissolved in chloroform (20 ml), and 4-dimethylaminopyridine (293 mg) and allyl chloroformate (0.25 ml) were added, followed by stirring at room temperature for one hour. The reaction solution was washed with water and a saturated sodium chloride aqueous solution and then dried over anhydrous magnesium sulfate. Then, the solvent was distilled off under reduced pressure. The residue was purified by silica gel column chromatography (ethyl acetate/hexane=3/1) to obtain the above identified compound (1.0 g).

(4) Preparation of 6-[2-(5-ethyl-4-methyl-1,3-thiazol-2-yl) ethyl]-4-morpholino-2-[3-(2-propenyloxycarbonylamino) benzylamino]pyridine 2-[N-tert-butoxycarbonyl-N-3-(2-propenyloxycarbonylamino)benzylamino]-6-[2-(5-ethyl-4-methyl-1,3-thiazol-2-yl)ethyl]-4-morpholinopyridine (1.0 g) was dissolved in trifluoroacetic acid (5 ml), followed by stirring at room temperature for one hour. The reaction solution was concentrated under reduced pressure, and the residue was dissolved in ethyl acetate, washed with a saturated sodium hydrogen carbonate aqueous solution and a saturated sodium chloride aqueous solution and dried over anhydrous magnesium sulfate. The solvent was distilled off under reduced pressure, and the residue was purified by silica gel column chromatography (chloroform/methanol=50/1→20/1) to obtain the above identified compound (818 mg) as a pale yellow oily substance.

$^1$H-NMR(CDCl$_3$) δ: 1.21(3H, t, J=7.6 Hz), 2.29(3H, s), 2.69(2H, q, J=7.6 Hz), 2.96(2H, t, J=7.9 Hz), 3.15(4H, t, J=5.0 Hz), 3.29(2H, t, J=7.9 Hz), 3.76(4H, t, J=5.0 Hz), 4.43(2H, d, J=5.6 Hz), 4.65(2H, dd, J=1.5 Hz, 6.2 Hz), 5.15(1H, d, J=5.6 Hz), 5.25(1H, dd, J=1.5 Hz, 11.0 Hz), 5.35(1H, dd, J=1.5 Hz, 17.1 Hz), 5.54(1H, d, J=2.0 Hz), 5.95 (1H, ddt, J=6.2 Hz, 11.0 Hz, 17.1 Hz), 6.03(1H, d, J=2.0 Hz), 6.82(1H, brs), 7.06(1H, d, J=7.2 Hz), 7.23–7.34(2H, m), 7.37–7.39(1H, m).

Compounds of Examples 110 to 132 were obtained in the same manner as in Example 109 except that the material used in Example 109 was changed to the materials corresponding to the respective desired compounds.

EXAMPLE 110

6-[2-(5-ethyl-1,3-thiazol-2-yl)ethyl]-4-morpholino-2-[3-(2-propenyloxycarbonylamino)benzylamino]pyridine $^1$H-NMR(CDCl$_3$) δ: 1.27(3H, t, J=7.6 Hz), 2.78(2H, q, J=7.6 Hz), 3.01(2H, t, J=7.7 Hz), 3.16(4H, t, J=4.9 Hz), 3.36(2H, t, J=7.7 Hz), 3.76(4H, t, J=4.9 Hz), 4.44(2H, d, J=5.6 Hz), 4.65(2H, d, J=5.7 Hz), 5.25(1H, dd, J=1.3 Hz, 10.5 Hz), 5.35(1H, dd, J=1.6 Hz, 17.3 Hz), 5.53 (1H, d, J=1.8 Hz), 5.90–6.00(1H, m), 6.01 (1H. d, J=1.8 Hz), 7.00–7.10(2H, m), 7.20–7.40(3H, m).

EXAMPLE 111

2-[1-(3-cyclopropylmethyloxycarbonylamino-5-trifluoromethylphenyl)propylamino]-6-[2-(5-ethyl-1,3-thiazol-2-yl)ethyl]-4-morpholinopyridine $^1$H-NMR(CDCl$_3$) δ: 0.25–0.35(2H, m), 0.50–0.65(2H, m), 0.95 (3H, t, J=7.4 Hz), 1.0–1.20(1H, m), 1.26(3H, q, J=7.4 Hz), 1.75–1.95(1H, m), 2.00–2.20(2H, m), 2.79(2H, q, J=7.4 Hz), 3.00–3.30 (6H, m), 3.33(2H, t, J=7.4 Hz), 3.60–3.80(4H, m), 4.99(2H, d, J=7.3 Hz), 4.15–4.30(1H, m), 5.31(1H, d, J=2.0 Hz), 5.95(1H, d, J=2.0 Hz), 7.20–7.40(2H, m), 7.48(1H, s), 7.83(1H, s), 8.45(1H, brs).

EXAMPLE 112

2-[1-(3-cyclopropylmethyloxycarbonylamino-5-methoxyphenyl)propylamino]-6-[2-(5-ethyl-1,3-thiazol-2-yl)ethyl]-4-morpholinopyridine $^1$H-NMR(CDCl$_3$) δ: 0.26–0.33(2H, m), 0.54–0.61 (2H, m), 0.95 (3H, t, J=7.4 Hz), 1.10–1.21(1H, m), 1.27(3H, t, J=7.5 Hz), 1.75–1.82(2H, m), 2.78(2H, q, J=7.5 Hz), 2.92–3.01(2H, m), 3.01–3.18 (4H, m), 3.28–3.35(2H, m), 3.68–3.76(4H, m), 3.77(3H, s), 3.97 (2H, d, J=7.3 Hz), 4.19–4.30(1H, m), 5.42(1H, d, J=2.0 Hz), 5.95 (1H, d, J=2.0 Hz), 6.61(1H, s), 6.83(1H, brs), 6.92(1H, s), 6.98(1H, s), 7.31(1H, s).

EXAMPLE 113

2-[1-(3-cyclopropylmethyloxycarbonylaminophenyl)propylamino]-6-[2-(5-ethyl-1,3-thiazol-2-yl)ethyl]-4-morpholinopyridine $^1$H-NMR(CDCl$_3$) δ: 0.28–0.36(2H, m), 0.55–0.64(2H, m), 0.95 (3H, t, J=7.4 Hz), 1.10–1.20(1H, m), 1.27(3H, t, J=7.5 Hz), 1.76–2.00(2H, m), 2.79(2H, dq, J=1.0 Hz, 7.5 Hz), 3.01(2H, t, J=7.6 Hz), 3.05–3.19(4H, m), 3.33(2H, t, J=7.6 Hz), 3.71(4H, t, J=4.8 Hz), 3.97(2H, d, J=7.3 Hz), 4.26(1H, dd, J=6.5 Hz, 12.9 Hz), 5.39(1H, d, J=2.0 Hz), 5.94(1H, d, J=2.0 Hz), 6.94(1H, s), 7.03–7.06(1H, m), 7.25(1H, s), 7.31(1H, s), 7.41(1H, s).

EXAMPLE 114

6-[2-(5-ethyl-1,3-thiazol-2-yl)ethyl]-4-morpholino-2-{1-[3-(2-propenyloxycarbonylamino)phenyl]propylamino}pyridine $^1$H-NMR(CDCl$_3$) δ: 0.95(3H, t, J=7.3 Hz), 1.27(3H, t, J=7.4 Hz), 1.77–1.97(2H, m), 2.79(2H, q, J=7.4 Hz), 2.99 (2H, t, J=7.8 Hz), 3.03–3.16(4H, m), 3.32(2H, t, J=7.8 Hz), 3.71(4H, t, J=4.9 Hz), 4.28(1H, dd, J=6.8 Hz, 13.1 Hz), 4.64(2H, d, J=5.6 Hz), 5.29(1H, dd, J=1.4 Hz, 10.4 Hz), 5.35(1H, dd, J=1.4 Hz, 17.2 Hz), 5.88–6.01 (1H, m), 5.40 (1H, d, J=1.9 Hz), 5.94(1H, d, J=1.9 Hz), 7.03–7.06 (2H, m), 7.20–7.33(2H, m), 7.40(1H, s).

EXAMPLE 115

6-[2-(4-ethyl-5-methyl-1,3-thiazol-2-yl)ethyl]-4-morpholino-2-[3-(2-propenyloxycarbonylamino)-5-trifluoromethylbenzylamino]pyridine $^1$H-NMR(CDCl$_3$) δ: 1.18(3H, t, J=7.5 Hz), 2.29(3H, s), 2.62(2H, q, J=7.5 Hz), 2.99(2H, t, J=7.8 Hz), 3.16(4H, t, J=5.0 Hz), 3.29(2H, t, J=7.8 Hz), 3.76(4H, t, J=5.0 Hz), 4.49(2H, d, J=5.9 Hz), 4.65(2H, d, J=5.7 Hz), 5.26(1H, d, J=10.0 Hz), 5.34(1H, d, J=17.0 Hz), 5.49 (1H, d, J=1.7 Hz), 5.95(1H, ddt, J=5.7 Hz, 10.0 Hz, 17.1 Hz), 6.02(1H, d, J=1.7 Hz), 7.19(1H, brs), 7.29–7.31(1H, m), 7.52–7.54(1H, m), 7.75–7.77(1H, m).

EXAMPLE 116

6-[2-(4-ethyl-5-methyl-1,3-thiazol-2-yl)ethyl]-2-[3-methoxy-5-(2-propenyloxycarbonylamino)benzylamino]-4-morpholinopyridine $^1$H-NMR(CDCl$_3$) δ: 1.19(3H, t, J=7.6 Hz), 2.28(3H, s), 2.62(2H, q, J=7.6 Hz), 2.93(2H, t, J=7.8 Hz), 3.17(4H, t, J=5.0 Hz), 3.30(2H, t, J=7.8 Hz), 3.76(4H, t, J=5.0 Hz), 3.78(3H, s), 4.38(2H,. d, J=5.6 Hz), 4.65(2H, d, J=5.5 Hz), 5.25(1H, d, J=11.8 Hz), 5.35(1H, d, J=15.3 Hz), 5.53(1H, d, J=1.8 Hz), 5.95(1H, ddt, J=5.5 Hz, 11.8 Hz, 15.3 Hz), 6.03(1H, d, J=1.8 Hz), 6.61–6.63(1H, m), 6.78–6.82(1H, m), 6.89–6.91(1H, m), 7.02–7.05(1H, m).

EXAMPLE 117

6-[2-(4-ethyl-5-methyl-1,3-thiazol-2-yl)ethyl]-2-(3-isobutyloxycarbonylamino-5-trifluoromethylbenzylamino)-4-morpholinopyridine $^1$H-NMR(CDCl$_3$) δ: 0.94(6H, d, J=6.7 Hz), 1.18(3H, t, J=7.6 Hz), 1.87–2.00(1H, m), 2.29(3H, s), 2.62(2H, q, J=7.6 Hz), 2.97(2H, t, J=7.7 Hz), 3.15(4H, t, J=4.9 Hz), 3.29(2H, t, J=7.7 Hz), 3.76(4H, t, J=4.9 Hz), 3.94(2H, d, J=6.6 Hz), 4.49(2H, d, J=5.7 Hz), 5.49(1H, brs), 5.51(1H, d, J=1.8 Hz), 6.02(1H, d, J=1.8 Hz), 7.21(1H, s), 7.29(1H, s), 7.54(1H, s), 7.75(1H, s).

EXAMPLE 118

6-[2-(4-ethyl-5-methyl-1,3-thiazol-2-yl)ethyl]-2-(3-isobutyloxycarbonylamino-5-methoxybenzylamino)-4-morpholinopyridine $^1$H-NMR(CDCl$_3$) δ: 0.94(6H, d, J=6.7 Hz), 1.20(3H, t, J=7.5 Hz), 1.88–2.00(1H, m), 2.29(3H, s), 2.63(2H, q, J=7.5

Hz), 2.97(2H, t, J=7.8 Hz), 3.16(4H, t, J=5.0 Hz), 3.29(2H, t, J=7.8 Hz), 3.75(4H, t, J=5.0 Hz), 3.77(3H, s), 3.92(2H, d, J=6.7 Hz), 4.37(2H, d, J=5.8 Hz), 5.53(1H, d, J=1.9 Hz), 6.01(1H, d, J=1.9 Hz), 5.63(1H, brs), 6.61(1H, s), 6.90(1H, s), 7.04(1H, s), 7.06(1H, s).

EXAMPLE 119

2-[1-(3-cyclopropylmethyloxycarbonylamino-5-methylphenyl)propylamino]-6-[2-(4-ethyl-5-methyl-1,3-thiazol-2-yl)ethyl]-4-morpholinopyridine $^1$H-NMR(CDCl$_3$) δ: 0.29–0.35(2H, m), 0.56–0.61(2H, m), 0.95 (3H, t, J=7.4 Hz), 1.15–1.31(1H, m), 1.21(3H, t, J=7.5 Hz), 1.81–1.93(2H, m), 2.31(6H, s), 2.64(2H, q, J=7.5 Hz), 2.97(2H, t, J=7.7 Hz), 3.05–3.17(4H, m), 3.23–3.31 (2H, m), 3.73(4H, t, J=4.8 Hz), 3.98(2H, d, J=7.3 Hz), 4.21–4.24(1H, m), 5.43(1H, s), 5.97 (1H, s), 6.68(1H, brs), 6.88(1H, s), 7.08(1H, s), 7.21(1H, s).

EXAMPLE 120

2-[1-(3-cyclopropylmethyloxycarbonylamino-5-hydroxymethylphenyl)propylamino]-6-[2-(4-ethyl-5-methyl-1,3-thiazol-2-yl)ethyl]-4-morpholinopyridine $^1$H-NMR(CDCl$_3$) δ: 0.25–0.35(2H, m), 0.55–0.65(2H, m), 0.94 (3H, t, J=7.2 Hz), 1.09–1.21(1H, m), 1.19(3H, t, J=7.5 Hz), 1.75–1.90(2H, m), 2.29(3H, s), 2.63(2H, q, J=7.2 Hz), 2.95–3.05(2H, m), 3.10–3.30(6H, m), 3.72(4H, t, J=5.0 Hz), 3.96(2H, d, J=7.3 Hz), 4.20–4.30(1H, m), 4.67(2H, s), 5.43(1H, d, J=2.0 Hz), 5.95(1H, d, J=2.0 Hz), 6.71(1H, s), 7.12(1H, s), 7.22(1H, s), 7.34(1H, s).

EXAMPLE 121

6-[2-(4-ethyl-5-methyl-1,3-thiazol-2-yl)ethyl]-2-{1-[3methyl-5-(2-propenyloxycarbonylamino)-phenyl]propylamino}-4-morpholinopyridine $^1$H-NMR(CDCl$_3$) δ: 0.94(3H, t, J=7.4 Hz), 1.20(3H, t, J=7.6 Hz), 1.75–1.91(2H, m), 2.29(6H, s), 2.63(2H, q, J=7.6 Hz), 2.95(2H, t, J=7.9 Hz), 3.02–3.17(4H, m), 3.24–3.29 (2H, m), 3.71(4H, t, J=4.9 Hz), 4.18–4.25(1H, m), 4.63(2H, d, J=5.6 Hz), 5.25(1H, d, J=10.4 Hz), 5.35(1H, d, J=17.2 Hz), 5.42(1H, d, J=2.0 Hz), 5.89–6.02(1H, m), 5.97(1H, d, J=2.0 Hz), 6.72(1H, brs), 6.88(1H, s), 7.07(1H, s), 7.20(1H, s).

EXAMPLE 122

6-[2-(5-ethyl-4-methyl-1,3-thiazol-2-yl)ethyl]-2-[3-methoxy-5-(2-propenyloxycarbonylamino)benzylamino]-4-morpholinopyridine $^1$H-NMR(CDCl$_3$) δ: 1.21(3H, t, J=7.6 Hz), 2.28(3H, s), 2.69(2H, q, J=7.6 Hz), 3.01(2H, t, J=7.8 Hz), 3.19(4H, t, J=4.9 Hz), 3.31(2H, t, J=7.8 Hz), 3.76(4H, t, J=4.9 Hz), 3.78(3H, s), 4.37(2H, d, J=5.9 Hz), 4.64(2H, dd, J=1.4 Hz, 5.6 Hz), 5.25(1H, dd, J=1.5 Hz, 10.4 Hz), 5.35(1H, dd, J=1.5 Hz, 17.2 Hz), 5.52(1H, d, J=2.0 Hz), 5.95 (1H, ddt, J=5.6 Hz, 10.4 Hz, 17.2 Hz), 6.03(1H, d, J=2.0 Hz), 6.62(1H, brs), 6.89–6.92(2H, m), 7.01–7.03(1H, m).

EXAMPLE 123

6-[2-(5-ethyl-1,3-thiazol-2-yl)ethyl]-2-[3-methoxy-5-(2-propenyloxycarbonylamino)benzylamino]-4-morpholinopyridine $^1$H-NMR(CDCl$_3$) δ: 1.28(3H, t, J=7.4 Hz), 2.80(2H, q, J=7.4 Hz), 3.12(2H, t, J=7.3 Hz), 3.26(4H, t, J=4.9 Hz), 3.35(2H, t, J=7.3 Hz), 3.73(4H, t, J=4.9 Hz), 3.78(3H, s), 4.32(2H, d, J=5.9 Hz), 4.63(2H, d, J=5.6 Hz), 5.26(1H, dd, J=1.3 Hz, 10.4 Hz), 5.35(1H, dd, J=1.3 Hz, 17.2 Hz), 5.43(1H, d, J=2.0 Hz), 5.90–5.99(2H, m), 6.61 (1H, s), 6.89–6.98(3H, m), 7.32(1H, s).

EXAMPLE 124

2-[1-(3-cyclopropylmethyloxycarbonylaminophenyl)propylamino]-6-[2-(5-ethyl-4-methyl-1,3-thiazol-2-yl)ethyl]-4-morpholinopyridine $^1$H-NMR(CDCl$_3$) δ: 0.28–0.34(2H, m), 0.55–0.62(2H, m),0.95 (3H, t, J=7.4 Hz), 1.10–1.30(1H, m), 1.21(3H, t, J=7.5 Hz), 1.80–2.05(2H, m), 2.28(3H, s), 2.69(2H, q, J=7.5 Hz), 3.02(2H, t, J=7.6 Hz), 3.05–3.25(4H, m), 3.28(2H, t, J=7.6 Hz), 3.71(4H, t, J=4.7 Hz), 3.97(2H, d, J=7.3 Hz), 4.15–4.22(1H, m), 5.38(1H, d, J=2.1 Hz), 5.96(1H, d, J=2.1 Hz), 6.88(1H, s), 7.03–7.06(1H, m), 7.22–7.26(1H, m), 7.42(1H, s).

EXAMPLE 125

2-[3-methoxy-5-(2-propenyloxycarbonylamino)benzylamino]-6-[2-(4-methyl-5-propyl-1,3-thiazol-2-yl)ethyl]-4-morpholinopyridine $^1$H-NMR(CDCl$_3$) δ: 0.94(3H, t, J=7.3 Hz), 1.52–1.66(2H, m), 2.28(3H, s), 2.63(2H, t, J=7.5 Hz), 3.02(2H, t, J=7.6 Hz), 3.20(4H, t, J=4.9 Hz), 3.30(2H, t, J=7.6 Hz), 3.75(4H, t, J=4.9 Hz), 3.78(3H, s), 4.35(2H, d, J=5.7 Hz), 4.64(2H, d, J=5.6 Hz), 5.25(1H, dd, J=1.4 Hz, 10.4 Hz), 5.34(1H, dd, J=1.4 Hz, 17.2 Hz), 5.50(1H, d, J=2.1 Hz), 5.87–6.00(1H, m), 6.01(1H, d, J=2.1 Hz), 6.62(1H, d, J=1.6 Hz), 6.94(1H, s), 6.97(1H, s), 7.00(1H, s), 7.01(1H, s).

EXAMPLE 126

6-[2-(4-methyl-5-propyl-1,3-thiazol-2-yl)ethyl]-4-morpholino-2-[3-(2-propenyloxycarbonylamino)benzylamino]pyridine $^1$H-NMR(CDCl$_3$) δ: 0.94(3H, t, J=6.8 Hz), 1.53–1.66(2H, m), 2.29(3H, s), 2.61–2.66(2H, m), 2.96(2H, t, J=7.5 Hz), 3.15(4H, t, J=4.9 Hz), 3.29(2H, t, J=7.5 Hz), 3.76(4H, t, J=4.9 Hz), 4.43(2H, d, J=5.6 Hz), 4.65(2H, d, J=5.7 Hz), 5.26(1H, dd, J=1.3 Hz, 10.5 Hz), 5.35(1H, dd, J=1.3 Hz, 17.3 Hz), 5.54(1H, d, J=1.9 Hz), 5.88–6.00 (1H, m), 6.03 (1H, d, J=1.9 Hz), 6.82(1H, brs), 7.07(1H, d, J=7.6 Hz), 7.23–7.39(3H, m).

EXAMPLE 127

2-[3-(isobutyloxycarbonylamino)-5-methoxybenzylamino]-6-[2-(4-methyl-5-propyl-1,3-thiazol-2-yl)ethyl]-4-morpholinopyridine $^1$H-NMR(CDCl$_3$) δ: 0.94(3H, t, J=7.3 Hz), 0.94(6H, d, J=6.8 Hz), 1.53–1.68(2H, m), 1.95(1H, m), 2.28(3H, s), 2.63(2H, t, J=7.5 Hz), 2.85(1H, brs), 2.98(2H, t, J=7.8 Hz), 3.16(4H, t,. J=4.9 Hz), 3.29 (2H, t, J=7.8 Hz), 3.76(4H, t, J=4.9 Hz), 3.77(3H, s), 3.94(2H, d, J=6.6 Hz), 4.49(2H, d, J=5.9 Hz), 5.50(1H, d, J=2.0 Hz), 5.64(1H, brs), 6.03(1H, d, J=2.0 Hz), 6.62(1H, s), 6.90(1H, s), 7.04(1H, s).

EXAMPLE 128

2-[3-(cyclopropylmethyloxycarbonylamino)-5-methoxybenzylamino]-6-[2-(4-methyl-5-propyl-1,3-thiazol-2-yl)ethyl]-4-morpholinopyridine $^1$H-NMR(CDCl$_3$) δ: 0.28–0.33(2H, m), 0.55–0.61(2H, m), 0.94 (3H, t, J=7.3 Hz), 1.08–1.21(1H, m), 1.54–1.67(2H, m), 2.29(3H, s), 2.63(2H, t, J=7.4 Hz), 2.98(2H, t, J=7.9 Hz), 3.16(4H, t, J=4.9 Hz), 3.30(2H, t, J=7.9 Hz), 3.76(4H, t, J=4.9 Hz), 3.77(3H, s), 3.97(2H, d, J=7.3 Hz), 4.37(2H, d, J=5.6 Hz), 5.53(1H, d, J=2.0 Hz), 5.60(1H, brs), 6.02(1H, d, J=2.0 Hz), 6.62(1H, s), 6.90(1H, s), 6.92 (1H, s), 7.03(1H, s), 7.04(1H, s).

EXAMPLE 129

2-[3-(cyclopropylmethyloxycarbonylamino)-5-trifluoromethylbenzylamino]-6-[2-(4-methyl-5-propyl-1,3-thiazol-2-yl)ethyl]-4-morpholinopyridine $^1$H-NMR(CDCl$_3$) δ: 0.28–0.33(2H, m), 0.55–0.59(2H, m), 0.94 (3H, t, J=7.3 Hz), 1.08–1.20(1H, m), 1.53–1.67(2H, m), 2.28(3H, s), 2.63(2H, t, J=7.5 Hz), 2.98(2H, t, J=7.8 Hz), 3.10(1H, brs), 3.16 (4H, t, J=4.9 Hz), 3.29(2H, t, J=7.8 Hz), 3.76(4H, t, J=4.9 Hz), 3.98 (2H, d, J=7.3 Hz), 4.48(2H, d, J=5.9 Hz), 5.51(1H, d, J=2.0 Hz), 5.60(1H, brs), 6.03(1H, d, J=2.0 Hz), 7.28(1H, s), 7.53(1H, s), 7.75 (1H, s).

EXAMPLE 130

2-{1-[3-methoxy-5-(2-propenyloxycarbonylamino) phenyl]ethylamino}-6-[2-(4methyl-5-propyl-1,3-thiazol-2-yl)ethyl]-4-morpholinopyridine $^1$H-NMR(CDCl$_3$) δ: 0.94(3H, t, J=7.8 Hz), 1.55(3H, d, J=6.9 Hz), 1.54–1.63(2H, m), 2.28(3H, s), 2.63(2H, t, J=7.2 Hz), 3.01(2H, t, J=7.7 Hz), 3.06–3.19(4H, m), 3.29–3.34 (2H, m), 3.71(4H, t, J=4.6 Hz), 3.78(3H, s), 4.43–4.53(1H, m), 4.64(2H, d, J=5.7 Hz), 5.24–5.38(2H, m), 5.38(1H, s), 5.88–5.99(1H, m), 5.97(1H, s), 6.64(1H, s), 6.84(1H, s), 6.94(1H, s), 7.00(1H, s).

EXAMPLE 131

2-[1-(3-cyclopropylmethyloxycarbonylamino-5methoxyphenyl)ethylamino]-6-[2-(4-methyl-5-propyl-1,3-thiazol-2-yl)ethyl]-4-morpholinopyridine $^1$H-NMR(CDCl$_3$) δ: 0.28–0.34(2H, m), 0.56–0.61(2H, m), 0.94 (3H, t, J=7.5 Hz), 1.10–1.21(1H, m), 1.55(3H, d, J=6.6 Hz), 1.54–1.63(2H, m), 2.29(3H, s), 2.63(2H, t, J=7.2 Hz), 3.00(2H, t, J=8.1 Hz), 3.07–3.18(4H, m), 3.11(2H, t, J=8.1 Hz), 3.71(4H, t, J=4.8 Hz), 3.78(3H, s), 3.97(2H, d, J=9.6 Hz), 4.63(1H, m), 5.39(1H, s), 5.98(1H, s), 6.64(1H, s), 6.75(1H, s), 6.94(1H, s), 7.00(1H, s).

EXAMPLE 132

6-[2-(2-cyclopenteno[d]thiaiolyl)ethyl]-4-morpholino-2-[3-(2-propenyloxycarbonylamino) benzylamino]pyridine $^1$H-NMR(CDCl$_3$) δ: 2.41–2.50(2H, m), 2.78–2.87(4H, m), 3.03 (2H, t, J=7.8 Hz), 3.17(4H, t, J=4.8 Hz), 3.37(2H, t, J=7.8 Hz), 3.76 (4H, t, J=4.8 Hz), 4.42(2H, d, J=6.0 Hz), 4.65(2H, d, J=5.7 Hz), 5.25 (1H, dd, J=1.2 Hz, 10.5 Hz), 5.35(1H, dd, J=1.2 Hz, 17.4 Hz), 5.52(1H, d, J=2.1 Hz), 5.89–6.02(1H, m), 6.03(1H, d, J=2.1 Hz), 6.89(1H, brs), 7.06(1H, d, J=7.2 Hz), 7.23–7.33(2H, m), 7.40(1H, s).

EXAMPLE 133

Preparation of 2-[3-chloro-5-(2-propenyloxycarbonylamino)benzylamino]-6-[2-(5-ethyl-4-methyl-1,3-thiazol-2-yl)ethyl]-4-morpholinopyridine (1) Preparation of 2-[N-tert-butoxycarbonyl-N-(3-chloro-5-methoxycarbonylbenzyl)amino]-6-[2-(5-ethyl-4-methyl-1,3-thiazol-2-yl)ethyl]-4-morpholinopyridine 2-tert-butoxycarbonylamino-6-[2-(5-ethyl-4-methyl-1,3-thiazol-2-yl)ethyl]-4-morpholinopyridine (500 mg) obtained in Example 109-(1) was dissolved in dimethylformamide (12 ml), and 60% sodium hydride (58 mg) was added under cooling with ice, followed by stirring at room temperature for one hour. The reaction solution was cooled with ice, and a solution of methyl 3-chloro-5-chloromethylbenzoate (438 mg) in dimethylformamide (5 ml), was added thereto, followed by stirring at room temperature for 13 hours. The reaction solution was diluted with ethyl acetate, washed with water and a saturated sodium chloride aqueous solution and then, dried over anhydrous magnesium sulfate. Then, the solvent was distilled off under reduced pressure. The residue was purified by silica gel column chromatography (hexane/ethyl acetate=1/2) to obtain the above identified compound (628 mg).

(2) Preparation of 2-{N-tert-butoxycarbonyl-N-[3-chloro-5-(2-propenyloxycarbonylamino)benzyl]amino}-6-[2-(5-ethyl-4-methyl-1,3-thiazol-2-yl)ethyl]-4-morpholinopyridine 2-[N-tert-butoxycarbonyl-N-(3-chloro-5-methoxycarbonylbenzyl)amino]-6-[2-(5-ethyl-4-methyl-1,3-thiazol-2-yl)ethyl]-4-morpholinopyridine (628 mg) was dissolved in methanol (10 ml), and a 1 N sodium hydroxide aqueous solution (2 ml) was added thereto, followed by stirring at 45° C. for 1.5 hours. The reaction solution was diluted with water, neutralized with a 1 N potassium hydrogen sulfate aqueous solution and extracted with ethyl acetate. The organic layer was washed with a saturated sodium chloride aqueous solution and then, dried over anhydrous magnesium sulfate. Then, the solvent was distilled off under reduced pressure. The residue was dissolved in dioxane (10 ml), and diphenylphosphoryl azide (280 µl) and triethylamine (209 µl) were added thereto, followed by stirring at room temperature for 50 minutes. Then, allyl alcohol (20 ml) was added thereto, followed by refluxing under heating for one hour. The reaction solution was diluted with ethyl acetate, washed with water and a saturated sodium chloride aqueous solution and then, dried over anhydrous magnesium sulfate. The solvent was distilled off under reduced pressure, and the residue was purified by silica gel column chromatography (hexane/ethyl acetate=1/2) to obtain the above identified compound (470 mg).

(3) Preparation of 2-[3-chloro-5-(2-propenyloxycarbonylamino)benzylamino]-6-[2-(5-ethyl-4-methyl-1,3-thiazol-2-yl)ethyl]-4-morpholinopyridine 2-{N-tert-butoxycarbonyl-N-[3-chloro-5-(2-propenyloxycarbonylamino)benzyl]amino}-6-[2-(5-ethyl-4-methyl-1,3-thiazol-2-yl)ethyl]-4-morpholinopyridine (470 mg) was dissolved in trifluoroacetic acid (5 ml), followed by stirring at room temperature for 30 minutes. The reaction solution was concentrated under reduced pressure, and the residue was dissolved in ethyl acetate, washed with a saturated sodium hydrogen carbonate aqueous solution and a saturated sodium chloride aqueous solution and then, dried over anhydrous magnesium sulfate. The solvent was distilled off under reduced pressure, and the residue was purified by silica gel column chromatography (chloroform/methanol=50/1→20/1) to obtain the above identified compound (307 mg) as a white solid.

$^1$H-NMR(CDCl$_3$) δ: 1.26(3H, t, J=7.6 Hz), 2.78(2H, q, J=7.6 Hz), 3.05(2H, t, J=5.1 Hz), 3.16(4H, t, J=4.9 Hz), 3.37(2H, t, J=5.1 Hz), 3.76(4H, t, J=4.9 Hz), 4.42(2H, d, J=5.3 Hz), 4.65(2H, d, J=5.7 Hz), 5.25(1H, dd, J=1.3 Hz, 10.4 Hz), 5.34(1H, dd, J=1.3 Hz, 17.2 Hz), 5.49 (1H, d, J=2.0 Hz), 5.90–5.98(1H, m), 6.00 (1H, d, J=2.0 Hz), 7.02 (1H, s), 7.23(1H, s), 7.31(1H, s), 7.44(1H, s), 7.56(1H, s).

Compounds of Examples 134 and 135 were obtained in the same manner as in Example 133 except that the material used in Example 133 was changed to the materials corresponding to the respective desired compounds.

EXAMPLE 134

2-[3-chloro-5-(2-propenyloxycarbonylamino) benzylamino]-6-[2-(5-ethyl-1,3-thiazol-2-yl)ethyl]-4-morpholinopyridine $^1$H-NMR(CDCl$_3$) δ: 1.21 (3H, t, J=7.4 Hz), 2.28(3H, s), 2.69(2H, q, J=7.4 Hz), 2.98(2H, t, J=7.8 Hz), 3.17(4H, t, J=4.9 Hz), 3.29(2H, t, J=7.8 Hz), 3.77(4H, t, J=4.9 Hz), 4.41(2H, d, J=4.9 Hz), 4.65(2H, d, J=5.7 Hz), 5.25(1H, d, J=10.0 Hz), 5.34(1H, d, J=17.2 Hz), 5.49 (1H, d, J=1.9 Hz), 5.72(1H, brs), 5.94(1H, ddt, J=5.7 Hz, 10.0 Hz, 17.2 Hz), 6.03(1H, d, J=1.9 Hz), 7.02–7.04(1H, m), 7.08–7.10(1H, m), 7.22–7.26(1H, m), 7.47–7.49(1H, m).

EXAMPLE 135

2-[1-(3-chloro-5-(cyclopropylmethyloxycarbonylaminophenyl) propylamino]-6-[2-(5-ethyl-4-methyl-1,3-thiazol-2-yl)ethyl]-4-morpholinopyridine $^1$H-NMR(CDCl$_3$) δ: 0.28–0.33(2H, m), 0. 55–0.61 (2H, m), 0.98 (3H, t, J=7.4 Hz), 1.07–1.35(1H, m), 1.21(3H, t, J=7.5 Hz), 1.76–1.98(2H, m), 2.28(3H, s), 2.69(2H, q, J=7.5 Hz), 3.02(2H, t, J=7.7 Hz), 3.13–3.24(4H, m), 3.26–3.35 (2H, m), 3.73(4H, t, J=4.8 Hz), 3.97(2H, d, J=7.3 Hz), 4.22(1H, dd, J=6.6 Hz, 13.2 Hz), 5.35 (1H, d, J=2.0 Hz), 5.98(1H, d, J=2.0 Hz), 6.99–7.02(1H, m), 7.02 (1H, s), 7.21–7.24(1H, m), 7.44–7.47(1H, m).

EXAMPLE 136

Preparation of 6-[2-(5-ethyl-1,3-oxazol-2-yl)ethyl]-4-morpholino-2-[3-(2-propenyloxycarbonylamino) benzylamino]pyridine (1) Preparation of 2-tert-butoxycarbonylamino-6-[2-(5-ethyl-1,3-oxazol-2-yl)ethyl]-4-morpholinopyridine An amide (200 mg) obtained by condensing 6-tert-butoxycarbonylamino-4-morpholinopyridine-2-ylpropionic acid obtained by alkali hydrolysis of the compound obtained in Example 22-(3), with 1-amino-2-butanone hydrochloride (272 mg), under the same condition as in Example 109-(1), was dissolved in dimethylformamide (5 ml), and thionyl chloride (0.04 ml) was added thereto, followed by stirring at 0° C. for one hour and at 40° C. for one hour. The reaction solution was poured into water (50 ml) and extracted three time with ethyl acetate (30 ml). The organic layers were put together, washed with 30 ml each of water and a saturated sodium chloride aqueous solution and then, dried over anhydrous magnesium sulfate. Then, the solvent was distilled off under reduced pressure. The residue was purified by silica gel column chromatography (ethyl acetate) to obtain the above identified compound (40 mg).

(2) Preparation of 6-[2-(5-ethyl-1,3-oxazol-2-yl)ethyl]-4-morpholino-2-[3-(2-propenyloxycarbonylamino) benzylamino]pyridine Using the compound obtained by the above reaction, the above identified compound was obtained in the same manner as in Example 109-(2), (3) and (4).

$^1$H-NMR(CDCl$_3$) δ: 1.21(3H, t, J=7.5 Hz), 2.62(2H, q, J=7.5 Hz), 3.00(2H, t, J=7.4 Hz), 3.12–3.17 (6H, m), 3.75 (4H, t, J=4.9 Hz), 4.44(2H, d, J=5.6 Hz), 4.65(2H, d, J=5.6 Hz), 5.25(1H, dd, J=1.3 Hz, 10.6 Hz), 5.35(1H, dd, J=1.3 Hz, 15.8 Hz), 5.51(1H, d, J=2.0 Hz), 5.91–5.99(1H, m), 6.00(1H, d, J=2.0 Hz), 6.59(1H, s), 7.03(1H, d, J=7.4 Hz), 7.23–7.41 (3H, m).

EXAMPLE 137

Preparation of 6-(5-ethyl-1,3-thiazol-2-yloxymethyl)-4-morpholino-2-[3-(2-propenyloxycarbonylamino)benzylamino]pyridine (1) Preparation of 2-[N-tert-butoxycarbonyl-N-3-(2-propenyloxycarbonylamino)benzylamino]-6-(5-ethyl-1,3-thiazol-2-yloxymethyl)-4-morpholinopyridine A solution of 2-[N-tert-butoxycarbonyl-N-3-(2-propenyloxycarbonylamino)benzylamino]-4-morpholino-6-pyridinemethanol (111 mg) obtained by deprotecting by the method of Example 66-(4) the tetrahydropyranyl group of the compound obtained in Example 66-(1), and 2-bromo-5-ethyl-1,3-thiazole (48 mg) in dimethylformamide (1 ml), was added to a suspension of 60% sodium hydride (6 mg) in dimethylformamide (1 ml), followed by stirring at room temperature for two hours. Further, 60% sodium hydride (12 mg) was additionally added, followed by stirring at 50° C. overnight. The reaction solution was poured into water and extracted with ethyl acetate. The organic layer was washed with water, a saturated sodium hydrogen carbonate aqueous solution and a saturated sodium chloride aqueous solution and then, dried over anhydrous magnesium sulfate. Then, the solvent was distilled off under reduced pressure. The residue was purified by silica gel column chromatography (ethyl acetate) to obtain the above identified compound (17 mg).

(2) Preparation of 6-(5-ethyl-1,3-thiazol-2-yloxymethyl)-4-morpholino-2-[3-(2-propenyloxycarbonylamino) benzylamino]pyridine Using the compound obtained by the above reaction, the above identified compound was obtained by reduction of a nitro group, 2-propenyloxycarbonylation and deprotecting a tert-butoxycarbonyl group, in accordance with the above described method.

$^1$H-NMR(CDCl$_3$) δ: 1.25(3H, t, J=7.4 Hz), 2.68(2H, dq, J=1.5 Hz, 7.4 Hz), 3.19(4H, t, J=4.9 Hz), 3.77(4H, t, J=4.9 Hz), 4.42(2H, d, J=5.0 Hz), 4.65(2H, dd, J=2.0 Hz, 6.2 Hz), 5.20–5.40(1H, brs), 5.24 (2H, s), 5.26(1H, dd, J=1.4 Hz, 10.0 Hz), 5.36(1H, dd, J=1.4 Hz, 17.1 Hz), 5.59(1H, d, J=2.0 Hz), 5.96(1H, ddt, J=6.2 Hz, 10.0 Hz, 17.1 Hz), 6.31(1H, d, J=2.0 Hz), 6.70(1H, brs), 6.79(1H, d, J=1.5 Hz), 7.06(1H, d, J=6.7 Hz), 7.24–7.32(2H, m), 7.36–7.40(1H, m).

EXAMPLE 138

Preparation of 6-(5-ethyl-1,3,4-thiadiazol-2-ylthiomethyl)-2-{3-methoxycarbonyl-1-[3-(2-propenyloxycarbonylamino)phenyl]propylamino}-4-morpholinopyridine (1) Preparation of 2-{N-tert-butoxycarbonyl-N-[3-methoxycarbonyl-1-(3-nitrophenyl)propyl]amino}-6-(5-ethyl-1,3,4-thiadiazol-2-ylthiomethyl)-4-morpholinopyridine Tert-butyl N-[6-(5-ethyl-1,3,4-thiadiazol-2-ylthiomethyl)-4-morpholino-2-pyridyl]carbamate obtained in Example 1-(5) and ethyl 4-bromo-4-(3-nitrophenyl) butylate, were reacted under the same condition as in Example 1-(6) to obtain the above identified compound.

(2) Preparation of 2-[N-tert-butoxycarbonyl-N-{3-methoxycarbonyl-1-[3-(2-propenyloxycarbonylamino) phenyl]propyl}amino]-6-(5-ethyl- 1,3,4-thiadiazol-2-ylthiomethyl)-4-morpholinopyridine Using the compound obtained by the above reaction, the above identified compound was obtained by reduction of a nitro group and 2-propenyloxycarbonylation, in accordance with the above described method.

(3) Preparation of 6-(5-ethyl-1,3,4-thiadiazol-2-ylthiomethyl)-2-{3-methoxycarbonyl-1-[3-(2-propenyloxycarbonylamino)phenyl]propylamino}-4-morpholinopyridine Using the compound obtained by the above reaction, the above identified compound was obtained by deprotecting a tert-butoxycarbonyl group in accordance with the above described method.

$^1$H-NMR(CDCl$_3$) δ: 1.37(3H, t, J=7.5 Hz), 2.07–2.20(2H, m), 2.39(2H, t, J=7.3 Hz), 3.02–3.16(6H, m), 3.65(3H, s), 3.70–3.74 (4H, m), 4.37(2H, s), 4.50–4.60(1H, m), 4.65(2H, d, J=5.6 Hz), 4.95–5.05(1H, brs), 5.25(1H, d, J=10.4 Hz), 5.35(1H, d, J=17.2 Hz), 5.48(1H, d, J=1.8 Hz), 5.95(1H, ddt, J=5.6 Hz, 10.4 Hz, 7.2 Hz), 6.25 (1H, d, J=1.8 Hz), 6.76(1H, brs), 7.04(1H, d, J=6.5 Hz), 7.25–7.27 (2H, m), 7.38(1H, s).

EXAMPLE 139

Preparation of 6-(5-ethyl-1,3,4-thiadiazol-2-ylthiomethyl)-2-{4-hydroxy-1-[3-(2-propenyloxycarbonylamino)phenyl]butylamino}-4-morpholinopyridine (1) Preparation of 2-[N-tert-butoxycarbonyl-N-{4-hydroxy-1-[3-(2 -propenyloxycarbonylamino)phenyl]butyl}amino]-6-(5-ethyl-1,3,4-thiadiazol-2-ylthiomethyl)-4-morpholinopyridine 2-[N-tert-butoxycarbonyl-N-{3-methoxycarbonyl-1-[3-(2-propenyloxycarbonylamino)phenyl]propyl}amino]-6-(5-ethyl-1,3,4-thiadiazol-2-ylthiomethyl)-4-morpholinopyridine (100 mg) obtained in Example 138-(2) was dissolved in tetrahydrofuran (3 ml), and a 2 M lithium borohydride-tetrahydrofuran solution (0.1 ml) was added thereto, followed by stirring at room temperature for 15 hours. The reaction solution was diluted with ethyl acetate, washed with a saturated sodium chloride aqueous solution and then, dried over anhydrous magnesium sulfate. The solvent was distilled off under reduced pressure, and the residue was purified by silica gel column chromatography (hexane/ethyl acetate=1/2) to obtain the above identified compound (66 mg).

(2) Preparation of 6-(5-ethyl-1,3,4-thiadiazol-2-ylthiomethyl)-2-{4-hydroxy-1-[3-(2-propenyloxycarbonylamino)phenyl]butylamino}-4-morpholinopyridine Using the compound obtained by the above reaction, the above identified compound was obtained by deprotecting a tert-butoxycarbonyl group in accordance with the above described method.

$^1$H-NMR(CDCl$_3$) δ: 1.37(3H, t, J=7.5 Hz), 1.52–1.82(2H, m), 1.82–2.09(2H, m), 3.00–3.24(6H, m), 3.60–3.78(6H, m), 4.36–4.48(3H, m), 4.64(2H, d, J=5.6 Hz), 5.25(1H, d, J=10.4 Hz), 5.35 (1H, d, J=17.1 Hz), 5.41(1H, d, J=1.9 Hz), 5.87–6.01(2H, m), 6.34 (1H, d, J=1.9 Hz), 6.88–7.00(1H, brs), 7.02–7.08(1H, m), 7.29–7.30(2H, m), 7.41 (1H, s).

EXAMPLE 140

Preparation of 2-{3-carbamoyl-1-[3-(2-propenyloxycarbonylamino)phenyl]propylamino}-6-(5-ethyl-1,3,4-thiadiazol-2-ylthiomethyl)-4-morpholinopyridine (1) Preparation of 2-[N-tert-butoxycarbonyl-N-{3-carbamoyl-1-[3-(2-propenyloxycarbonylamino)phenyl]propyl}amino]-6-(5-ethyl-1,3,4-thiadiazol-2-ylthiomethyl)-4-morpholinopyridine The compound (60 mg) obtained in Example 138-(2) was dissolved in methanol (2 ml), and a 1 N sodium hydroxide aqueous solution (0.1 ml) was added thereto, followed by stirring at room temperature for 16 hours. To the reaction solution, a 10% citric acid aqueous solution was added, followed by extraction with ethyl acetate. The organic layer was washed with a saturated sodium chloride aqueous solution and then, dried over anhydrous magnesium sulfate. Then, the solvent was distilled off. The residue was dissolved in dimethylformamide (2 ml), and N-hydroxysuccinimide (20 mg) and 1-ethyl-3-(3-dimethylaminopropyl)carbodiimide hydrochloride (80 mg) were added thereto, followed by stirring at room temperature overnight. To the reaction solution, concentrated aqueous ammonia (0.3 ml) was added, followed by stirring at 40° C. overnight. To the reaction solution, water was added, followed by extraction with ethyl acetate. The organic layer was washed with water and a saturated sodium chloride aqueous solution and then, dried over anhydrous magnesium sulfate. Then, the solvent was distilled off, and the residue was purified by silica gel column chromatography (chloroform/methanol=30/1) to obtain the above identified compound (55 mg).

(2) Preparation of 2-{3-carbamoyl-1-[3-(2-propenyloxycarbonylamino)phenyl]propylamino}-6-(5-ethyl-1,3,4-thiadiazol-2-ylthiomethyl)-4-morpholinopyridine Using the compound obtained by the above reaction, the above identified compound was obtained by deprotecting a tert-butoxycarbonyl group in accordance with the above described method.

$^1$H-NMR(CDCl$_3$) δ: 1.37(3H, t, J=7.5 Hz), 2.02–2.16(1H, m), 2.16–2.40(3H, m), 3.00–3.18(6H, m), 3.68–3.76(4H, m), 4.36(2H, s), 4.59–4.68(3H, m), 5.08–5.20(1H, brs), 5.25(1H, d, J=10.2 Hz), 5.35(1H, d, J=16.4 Hz), 5.42–5.56 (2H, m), 5.95(1H, ddt, J=5.6 Hz, 10.2 Hz, 16.4 Hz), 6.08–6.20(1H, brs), 6.24(1H, d, J=1.8 Hz), 6.93 (1H, brs), 7.05(1H, d, J=6.3 Hz), 7.22–7.27(2H, m), 7.39(1H, s).

EXAMPLE 141

Preparation of 2-{4-amino-1-[3-(2-propenyloxycarbonylamino)phenyl]butylamino}-6-(5-ethyl-1,3,4-thiadiazol-2-ylthiomethyl)-4-morpholinopyridine The compound (90 mg) obtained in Example 139-(1) was dissolved in tetrahydrofuran (3 ml), and triethylamine (36 μl) and methanesulfonyl chloride (16 μl) were added thereto, followed by stirring at room temperature for 3 hours. To the reaction solution, water was added, followed by extraction with ethyl acetate. The organic layer was washed with a saturated sodium chloride aqueous solution and then, dried over anhydrous magnesium sulfate. The solvent was distilled off, and the residue was purified by silica gel column chromatography (chloroform/methanol=30/1) to obtain the corresponding mesylate (59 mg). The obtained mesylate was dissolved in dimethylformamide (2 ml), and sodium azide (15 mg) was added thereto, followed by stirring at room temperature for 14 hours. By carrying out post treatment in the same manner as the above and purification by silica gel column chromatography (hexane/ethyl acetate=3/2), the corresponding azide (37 mg) was obtained. The obtained azide was dissolved in tetrahydrofuran (2 ml)-water (0.2 ml), and triphenylphosphine (20 mg) was added thereto, followed by stirring at 40° C. for 20 hours. After carrying out post treatment in the same manner as described above, the tert-butoxycarbonyl group was deprotected by a trifluoroacetic acid to obtain the above identified compound (19 mg).

$^1$H-NMR(CDCl$_3$) δ: 1.36(3H, t, J=7.7 Hz), 1.40–1.98(4H, m), 2.50–2.70(2H, brs), 2.70–2.81(2H, m), 2.98–3.14(6H, m), 3.65–3.76(4H, m), 4.38(2H, s), 4.40–4.50(1H, m), 4.63 (2H, d, J=5.6 Hz), 5.18–5.32(1H, brs), 5.24(1H, d, J=10.4 Hz), 5.35(1H, d, J=17.2 Hz), 5.44(1H, s), 5.95(1H, ddt, J=5.6 Hz, 10.4 Hz, 17.2 Hz), 6.22(1H, s), 7.03(1H, d, J=7.2 Hz), 7.00–7.17(1H, brs), 7.18–7.30(2H, m), 7.40 (1H, s).

INDUSTRIAL APPLICABILITY

The compound of the present invention has a NPY antagonistic activity and thus is useful as a treating agent for various diseases associated with NPY, for example, cardiovascular diseases, such as hypertension, renal diseases, cardiac diseases or vasospasm, central diseases, such as hyperphagia, depression, epilepsy or dementia, metabolic diseases, such as obesity, diabetes or hormone unbalance, or glaucoma.

What is claimed is:

1. A compound represented by the formula (I) or a pharmaceutically acceptable salt thereof:

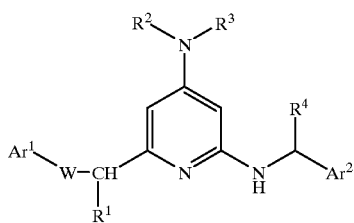

(I)

wherein $Ar^1$ is an aryl group or an aromatic heterocyclic group, which may be substituted by a group selected from the group consisting of a lower alkyl group, a lower hydroxyalkyl group, a lower alkylene group and a group represented by —$NR^aR^b$; each of $R^a$ and $R^b$ which are the same or different, is a hydrogen atom or a lower alkyl group; $R^1$ is a hydrogen atom or a lower alkyl group; each of $R^2$ and $R^3$ which are the same or different, is a lower alkyl group, or both of $R^2$ and $R^3$ are bonded to each other to form an alkylene group which may have an oxygen atom or a sulfur atom interposed, said alkylene group being a group which may be substituted by one or two lower alkyl groups; $R^4$ is a hydrogen atom, or a lower alkyl group which may be substituted by a group selected from the group consisting of a hydroxyl group, an amino group, a carbamoyl group and a lower alkoxycarbonyl group; $Ar^2$ is an aryl group or an aromatic heterocyclic group, which may be substituted by a group selected from the group consisting of a halogen atom, a hydroxyl group, a lower alkyl group, a lower haloalkyl group, a lower alkoxy group, a lower alkylthio group, a lower hydroxyalkyl group, a lower alkoxy-lower alkyl group, a group represented by —$NR^cR^d$ and a group represented by —$NR^e$—CO—$NR^fR^g$; $R^c$ is a hydrogen atom or a lower alkyl group; $R^d$ is a hydrogen atom, a lower alkyl group, a group represented by —CO—$R^h$ or —$SO_2$—$R^i$, or a heterocyclic group which may be substituted by a group selected from the group consisting of a halogen atom, a hydroxyl group, a lower alkyl group and a lower alkoxy group; each of $R^e$ and $R^f$ which are the same or different, is a hydrogen atom or a lower alkyl group; $R^g$ is a hydrogen atom, a lower alkyl group, a lower alkenyl group, or an aryl group or an aromatic heterocyclic group, which may be substituted by a group selected from the group consisting of a halogen atom, a hydroxyl group, a lower alkyl group and a lower alkoxy group; $R^h$ is a lower alkyl group, a lower alkoxy group, a lower alkoxy-lower alkyloxy group, a lower alkenyloxy group, a lower alkynyloxy group, or a group represented by —O—$(CH_2)_n$-Het; $R^i$ is a lower alkyl group, or a lower alkenyl group; Het is a heterocyclic group; n is an integer of from 1 to 3; W is an oxygen atom, a sulfur atom, or a group represented by —$CHR^j$— or —$NR^k$—; and each of $R^j$ and $R^k$ which are the same or different, is a hydrogen atom, or a lower alkyl group.

2. The compound according to claim 1, which is a compound represented by the formula (I-a):

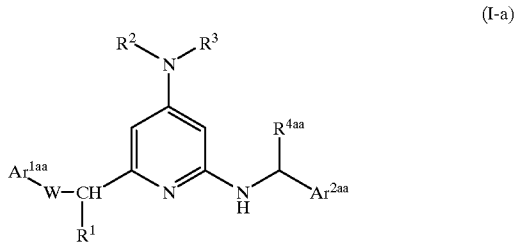

(I-a)

wherein $Ar^{1aa}$ is an aryl group or an aromatic heterocyclic group, which may be substituted by a group selected from the group consisting of a lower alkyl group and a group represented by —$NR^aR^b$; each of $R^a$ and $R^b$ which are the same or different, is a hydrogen atom or a lower alkyl group; each of $R^1$ and $R^{4aa}$ which are the same or different, is a hydrogen atom or a lower alkyl group; each of $R^2$ and $R^3$ which are the same or different, is a lower alkyl group, or both of $R^2$ and $R^3$ are bonded to each other to form an alkylene group which may have an oxygen atom or a sulfur atom interposed, said alkylene group being a group which may be substituted by one or two lower alkyl groups; $Ar^{2aa}$ is an aryl group or an aromatic heterocyclic group, which may be substituted by a group selected from the group consisting of a halogen atom, a hydroxyl group, a lower alkyl group, a lower haloalkyl group, a lower alkoxy group, a group represented by —$NR^cR^d$ and a group represented by —$NR^e$—CO—$NR^fR^g$; $R^c$ is a hydrogen atom or a lower alkyl group; $R^d$ is a hydrogen atom, a lower alkyl group, a group represented by —CO—$R^h$ or —$SO_2$—$R^i$, or a heterocyclic group which may be substituted by a group selected from the group consisting of a halogen atom, a hydroxyl group, a lower alkyl group and a lower alkoxy group; each of $R^e$ and $R^f$ which are the same or different, is a hydrogen atom or a lower alkyl group; $R^g$ is a hydrogen atom, a lower alkyl group, a lower alkenyl group, or an aryl group or an aromatic heterocyclic group, which may be substituted by a group selected from the group consisting of a halogen atom, a hydroxyl group, a lower alkyl group and a lower alkoxy group; $R^h$ is a lower alkyl group, a lower alkoxy group, a lower alkoxy-lower alkyloxy group, a lower alkenyloxy group, a lower alkynyloxy group, or a group represented by —O—$(CH_2)_n$-Het; $R^i$ is a lower alkyl group, or a lower alkenyl group; Het is a heterocyclic group; n is an integer of from 1 to 3; W is an oxygen atom, a sulfur atom, or a group represented by —$CHR^j$— or —$NR^k$—; and each of $R^j$ and $R^k$ which are the same or different, is a hydrogen atom, or a lower alkyl group.

3. The compound according to claim 1, wherein the aromatic heterocyclic group for $Ar^1$ is a furyl group, a thienyl group, an imidazolyl group, a thiazolyl group, an oxazolyl group, a triazolyl group, an oxadiazolyl group, a thiadiazolyl group, a pyridyl group, a pyrimidinyl group, a pyridazinyl group or a benzothiazolyl group.

4. The compound according to claim 1, wherein the aromatic heterocyclic group for $Ar^1$ is a thienyl group, an imidazolyl group, a thiazolyl group, a triazolyl group, an oxadiazolyl group, a thiadiazolyl group, a pyridyl group, a pyrimidinyl group or a pyridazinyl group.

5. The compound according to claim 1, wherein both of $R^2$ and $R^3$ are bonded to each other to form an alkylene group which may have an oxygen atom or a sulfur atom interposed, said alkylene group being a group which may be substituted by one or two lower alkyl groups.

6. The compound according to claim 5, wherein the alkylene group which may have an oxygen atom or a sulfur atom interposed, is a group which forms a morpholino group together with the adjacent nitrogen atom.

7. The compound according to claim 1, wherein $Ar^2$ is an aryl group or an aromatic heterocyclic group, which may be substituted by a group selected from the group consisting of a halogen atom, a lower alkyl group, a lower haloalkyl group, a lower alkoxy group, a lower alkylthio group, a lower hydroxyalkyl group, a lower alkoxy-lower alkyl group, a group represented by —$NR^cR^d$ and a group represented by —$NR^e$—CO—$NR^fR^g$.

8. The compound according to claim 1, wherein $Ar^2$ is an aryl group or an aromatic heterocyclic group, which may be substituted by a group selected from the group consisting of a halogen atom, a lower alkyl group, a lower haloalkyl group, a lower alkoxy group, a group represented by —$NR^cR^d$ and a group represented by —$NR^e$—CO—$NR^fR^g$.

9. The compound according to claim 1, wherein the aryl group for $Ar^2$ is a phenyl group.

10. The compound according to claim 1, wherein $R^c$ is a hydrogen atom, and $R^d$ is a group represented by —CO—$R^h$.

11. The compound according to claim 1, wherein $R^c$ is a hydrogen atom, and the heterocyclic group for $R^d$ is an oxazolyl group or a thiazolinyl group.

12. The compound according to claim 1, wherein $R^e$ and $R^f$ are the same and hydrogen atoms, and $R^g$ is a lower alkenyl group.

13. The compound according to claim 1, wherein $R^h$ is a lower alkoxy group, a lower alkenyloxy group or a lower alkynyloxy group.

14. The compound according to claim 1, wherein W is a sulfur atom.

15. The compound according to claim 1, wherein W is a group represented by —$CHR^j$—.

16. A pharmaceutical composition for hyperphagia, obesity or diabetes, which comprises a compound represented by the formula (I) or a pharmaceutically acceptable salt thereof, as an active ingredient:

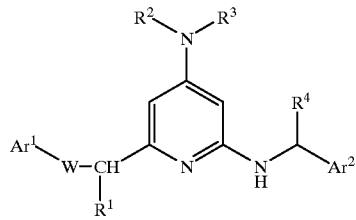

(I)

wherein $Ar^1$ is an aryl group or an aromatic heterocyclic group, which may be substituted by a group selected from the group consisting of a lower alkyl group, a lower hydroxyalkyl group, a lower alkylene group and a group represented by —$NR^aR^b$; each of $R^a$ and $R^b$ which are the same or different, is a hydrogen atom or a lower alkyl group; $R^1$ is a hydrogen atom or a lower alkyl group; each of $R^2$ and $R^3$ which are the same or different, is a lower alkyl group, or both of $R^2$ and $R^3$ are bonded to each other to form an alkylene group which may have an oxygen atom or a sulfur atom interposed, said alkylene group being a group which may be substituted by one or two lower alkyl groups; $R^4$ is a hydrogen atom, or a lower alkyl group which may be substituted by a group selected from the group consisting of a hydroxyl group, an amino group, a carbamoyl group and a lower alkoxycarbonyl group; $Ar^2$ is an aryl group or an aromatic heterocyclic group, which may be substituted by a group selected from the group consisting of a halogen atom, a hydroxyl group, a lower alkyl group, a lower haloalkyl group, a lower alkoxy group, a lower alkylthio group, a lower hydroxyalkyl group, a lower alkoxy-lower alkyl group, a group represented by —$NR^cR^d$ and a group represented by —$NR^e$—CO—$NR^fR^g$; $R^c$ is a hydrogen atom or a lower alkyl group; $R^d$ is a hydrogen atom, a lower alkyl group, a group represented by —CO—$R^h$ or —$SO_2$—$R^i$, or a heterocyclic group which may be substituted by a group selected from the group consisting of a halogen atom, a hydroxyl group, a lower alkyl group and a lower alkoxy group; each of $R^e$ and $R^f$ which are the same or different, is a hydrogen atom or a lower alkyl group; $R^g$ is a hydrogen atom, a lower alkyl group, a lower alkenyl group, or an aryl group or an aromatic heterocyclic group, which may be substituted by a group selected from the group consisting of a halogen atom, a hydroxyl group, a lower alkyl group and a lower alkoxy group; $R^h$ is a lower alkyl group, a lower alkoxy group, a lower alkoxy-lower alkyloxy group, a lower alkenyloxy group, a lower alkynyloxy group, or a group represented by —O—$(CH_2)_n$-Het; $R^i$ is a lower alkyl group, or a lower alkenyl group; Het is a heterocyclic group; n is an integer of from 1 to 3; W is an oxygen atom, a sulfur atom, or a group represented by —$CHR^j$— or —$NR^k$—; and each of $R^j$ and $R^k$ which are the same or different, is a hydrogen atom, or a lower alkyl group.

17. A process for treating hyperphagia, obesity or diabetes, which comprises administering to a patient in need thereof an effective amount of the compound according to claim 1.

* * * * *